US 6,616,819 B1

(12) United States Patent
Liamos et al.

(10) Patent No.: US 6,616,819 B1
(45) Date of Patent: *Sep. 9, 2003

(54) SMALL VOLUME IN VITRO ANALYTE SENSOR AND METHODS

(75) Inventors: Charles T. Liamos, Pleasanton, CA (US); Joseph A. Vivolo, San Francisco, CA (US); Fredric C. Colman, Oakland, CA (US)

(73) Assignee: TheraSense, Inc., Alameda, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/434,026

(22) Filed: Nov. 4, 1999

(51) Int. Cl.$^7$ ............................................. G01N 27/327
(52) U.S. Cl. ........................... 204/403.02; 204/403.03; 324/691; 324/693; 439/909
(58) Field of Search ........................... 204/401, 403.02, 204/403.03, 403.04, 406; 324/691, 692, 693; 439/630, 909

(56) References Cited

U.S. PATENT DOCUMENTS

| | | |
|---|---|---|
| 3,260,656 A | 7/1966 | Ross, Jr. |
| 3,653,841 A | 4/1972 | Klein |
| 3,719,564 A | 3/1973 | Lilly, Jr. et al. |
| 3,776,832 A | 12/1973 | Oswin et al. |
| 3,837,339 A | 9/1974 | Aisenberg et al. |
| 3,972,320 A | 8/1976 | Kalman |
| 3,979,274 A | 9/1976 | Newman |
| 4,008,717 A | 2/1977 | Kowarski |
| 4,016,866 A | 4/1977 | Lawton |
| 4,055,175 A | 10/1977 | Clemens et al. |
| 4,059,406 A | 11/1977 | Fleet |
| 4,076,596 A | 2/1978 | Connery et al. |
| 4,098,574 A | 7/1978 | Dappen |
| 4,100,048 A | 7/1978 | Pompei et al. |
| 4,151,845 A | 5/1979 | Clemens |
| 4,168,205 A | 9/1979 | Danninger et al. |

(List continued on next page.)

FOREIGN PATENT DOCUMENTS

| | | |
|---|---|---|
| DE | 29 03 216 | 8/1979 |
| DE | 227 029 A3 | 9/1985 |
| EP | 0 048 090 A2 | 3/1982 |
| EP | 0 078 636 A1 | 5/1983 |
| EP | 0 096 288 A1 | 12/1983 |

(List continued on next page.)

OTHER PUBLICATIONS

Abruña, H. D. et al., "Rectifying Interfaces Using Two–Layer Films of Electrochemically Polymerized Vinylpyridine and Vinylbipyridine Complexes of Ruthenium and Iron on Electrodes," *J. Am. Chem. Soc.*, 103(1):1–5 (Jan. 14, 1981).

Albery, W. J. et al., "Amperometric enzyme electrodes. Part II. Conducting salts as electrode materials for the oxidation of glucose oxidase," *J. Electroanal. Chem. Interfacial Electrochem.*, 194(2) (1 page—Abstract only) (1985).

(List continued on next page.)

Primary Examiner—Nam Nguyen
Assistant Examiner—Kaj K. Olsen
(74) Attorney, Agent, or Firm—Merchant & Gould P.C.

(57) ABSTRACT

A small volume sensor, and methods of making, for determining the concentration of an analyte, such as glucose or lactate, in a biological fluid, such as blood or serum, using techniques such as coulometry, amperometry, and potentiometry. The sensor includes a working electrode and a counter electrode, and can include an insertion monitoring trace to determine correct positioning of the sensor in a connector. In one embodiment, the sensor determines the concentration of the analyte by discharging an amount of charge into the sample, determining the time needed to discharge the charge, and determining the current used to electrolyze a portion of the analyte using the amount of charge and the amount of time.

8 Claims, 26 Drawing Sheets

U.S. PATENT DOCUMENTS

| | | |
|---|---|---|
| 4,172,770 A | 10/1979 | Semersky et al. |
| 4,178,916 A | 12/1979 | McNamara |
| 4,206,755 A | 6/1980 | Klein |
| 4,224,125 A | 9/1980 | Nakamura et al. |
| 4,240,438 A | 12/1980 | Updike et al. |
| 4,240,889 A | 12/1980 | Yoda et al. |
| 4,247,297 A | 1/1981 | Berti et al. |
| 4,271,119 A | 6/1981 | Columbus |
| 4,318,784 A | 3/1982 | Higgins et al. |
| 4,340,458 A | 7/1982 | Lerner et al. |
| 4,356,074 A | 10/1982 | Johnson |
| 4,365,637 A | 12/1982 | Johnson |
| 4,366,033 A | 12/1982 | Richter et al. |
| 4,375,399 A | 3/1983 | Havas et al. |
| 4,384,586 A | 5/1983 | Christiansen |
| 4,392,933 A | 7/1983 | Nakamura et al. |
| 4,401,122 A | 8/1983 | Clark, Jr. |
| 4,404,066 A | 9/1983 | Johnson |
| 4,407,959 A | 10/1983 | Tsuji et al. |
| 4,418,148 A | 11/1983 | Oberhardt |
| 4,420,564 A | 12/1983 | Tsuji et al. |
| 4,427,770 A | 1/1984 | Chen et al. |
| 4,431,004 A | 2/1984 | Bessman et al. |
| 4,436,094 A | 3/1984 | Cerami |
| 4,440,175 A | 4/1984 | Wilkins |
| 4,444,892 A | 4/1984 | Malmros |
| 4,450,842 A | 5/1984 | Zick et al. |
| 4,461,691 A | 7/1984 | Frank |
| 4,469,110 A | 9/1984 | Slama |
| 4,477,314 A | 10/1984 | Richter et al. |
| 4,483,924 A | 11/1984 | Tsuji et al. |
| 4,484,987 A | 11/1984 | Gough |
| 4,522,690 A | 6/1985 | Venkatasetty |
| 4,524,114 A | 6/1985 | Samuels et al. |
| 4,526,661 A | 7/1985 | Steckhan et al. |
| 4,534,356 A | 8/1985 | Papadakis |
| 4,538,616 A | 9/1985 | Rogoff |
| 4,543,955 A | 10/1985 | Schroeppel |
| 4,545,382 A | 10/1985 | Higgins et al. |
| 4,552,840 A | 11/1985 | Riffer |
| 4,560,534 A | 12/1985 | Kung et al. |
| 4,571,292 A | 2/1986 | Liu et al. |
| 4,573,994 A | 3/1986 | Fischell et al. |
| 4,581,336 A | 4/1986 | Malloy et al. |
| 4,595,011 A | 6/1986 | Phillips |
| 4,595,479 A | 6/1986 | Kimura et al. |
| 4,619,754 A | 10/1986 | Niki et al. |
| 4,633,878 A | 1/1987 | Bombardieri |
| 4,637,403 A | 1/1987 | Garcia et al. |
| 4,650,547 A | 3/1987 | Gough |
| 4,654,197 A | 3/1987 | Lilja et al. |
| 4,655,880 A | 4/1987 | Liu |
| 4,655,885 A | 4/1987 | Hill et al. |
| 4,671,288 A | 6/1987 | Gough |
| 4,679,562 A | 7/1987 | Luksha |
| 4,680,268 A | 7/1987 | Clark, Jr. |
| 4,682,602 A | 7/1987 | Prohaska |
| 4,684,537 A | 8/1987 | Graetzel et al. |
| 4,685,463 A | 8/1987 | Williams |
| 4,703,756 A | 11/1987 | Gough et al. |
| 4,711,245 A | 12/1987 | Higgins et al. |
| 4,714,874 A * | 12/1987 | Morris et al. ............... 324/444 |
| 4,717,673 A | 1/1988 | Wrighton et al. |
| 4,721,601 A | 1/1988 | Wrighton et al. |
| 4,726,378 A | 2/1988 | Kaplan |
| 4,750,496 A | 6/1988 | Reinhart et al. |
| 4,757,022 A | 7/1988 | Shults et al. |
| 4,758,323 A | 7/1988 | Davis et al. |
| 4,759,371 A | 7/1988 | Franetski |
| 4,759,828 A | 7/1988 | Young et al. |
| 4,764,416 A | 8/1988 | Ueyama et al. |
| 4,776,944 A | 10/1988 | Janata et al. |
| 4,781,798 A | 11/1988 | Gough |
| 4,784,736 A | 11/1988 | Lonsdale et al. |
| 4,795,707 A | 1/1989 | Niiyama et al. |
| 4,805,624 A | 2/1989 | Yao et al. |
| 4,813,424 A | 3/1989 | Wilkins |
| 4,815,469 A | 3/1989 | Cohen et al. |
| 4,820,399 A | 4/1989 | Senda et al. |
| 4,822,337 A | 4/1989 | Newhouse et al. |
| 4,830,959 A | 5/1989 | McNeil et al. |
| 4,832,797 A | 5/1989 | Vadgama et al. |
| 4,840,893 A | 6/1989 | Hill et al. |
| 4,848,351 A | 7/1989 | Finch |
| 4,854,153 A | 8/1989 | Miyagawa et al. |
| 4,871,351 A | 10/1989 | Feingold |
| 4,871,440 A | 10/1989 | Nagata et al. |
| 4,890,620 A | 1/1990 | Gough |
| 4,894,137 A | 1/1990 | Takizawa et al. |
| 4,897,162 A | 1/1990 | Lewandowski et al. |
| 4,897,173 A | 1/1990 | Nankai et al. |
| 4,909,908 A | 3/1990 | Ross et al. |
| 4,911,794 A | 3/1990 | Parce et al. |
| 4,919,141 A | 4/1990 | Zier et al. |
| 4,919,767 A | 4/1990 | Vadgama et al. |
| 4,923,586 A | 5/1990 | Katayama et al. |
| 4,927,516 A | 5/1990 | Yamaguchi et al. |
| 4,935,105 A | 6/1990 | Churchouse |
| 4,935,345 A | 6/1990 | Guilbeau et al. |
| 4,936,956 A | 6/1990 | Wrighton |
| 4,938,860 A | 7/1990 | Wogoman |
| 4,942,127 A | 7/1990 | Wada et al. |
| 4,945,045 A | 7/1990 | Forrest et al. |
| 4,950,378 A | 8/1990 | Nagata |
| 4,953,552 A | 9/1990 | DeMarzo |
| 4,954,087 A | 9/1990 | Lauks et al. |
| 4,968,400 A | 11/1990 | Shimomura et al. |
| 4,970,145 A | 11/1990 | Bennetto et al. |
| 4,974,929 A | 12/1990 | Curry |
| 4,986,271 A | 1/1991 | Wilkins |
| 4,994,167 A | 2/1991 | Shults et al. |
| 4,999,582 A | 3/1991 | Parks et al. |
| 5,034,192 A | 7/1991 | Wrighton et al. |
| 5,037,527 A | 8/1991 | Hayashi et al. |
| 5,070,535 A | 12/1991 | Hochmair et al. |
| 5,078,854 A | 1/1992 | Burgess et al. |
| 5,082,550 A | 1/1992 | Rishpon et al. |
| 5,082,786 A | 1/1992 | Nakamoto |
| 5,089,112 A | 2/1992 | Skotheim et al. |
| 5,094,951 A | 3/1992 | Rosenberg |
| 5,096,560 A | 3/1992 | Takai et al. |
| 5,096,836 A | 3/1992 | Macho et al. |
| 5,101,814 A | 4/1992 | Palti |
| 5,108,564 A | 4/1992 | Szuminsky et al. |
| 5,109,850 A | 5/1992 | Blanco et al. |
| 5,120,420 A | 6/1992 | Nankai et al. |
| 5,120,421 A | 6/1992 | Glass et al. |
| 5,126,034 A | 6/1992 | Carter et al. |
| 5,126,247 A | 6/1992 | Palmer et al. |
| 5,128,015 A | 7/1992 | Szuminsky et al. |
| 5,130,009 A | 7/1992 | Marsoner et al. |
| 5,133,856 A | 7/1992 | Yamaguchi et al. |
| 5,140,393 A | 8/1992 | Hijikihigawa et al. |
| 5,141,868 A | 8/1992 | Shanks et al. |
| 5,161,532 A | 11/1992 | Joseph |
| 5,165,407 A | 11/1992 | Wilson et al. |
| 5,168,046 A | 12/1992 | Hamamoto et al. |
| 5,174,291 A | 12/1992 | Schoonen et al. |
| 5,185,256 A | 2/1993 | Nankai et al. |
| 5,192,415 A | 3/1993 | Yoshioka et al. |
| 5,192,416 A | 3/1993 | Wang et al. |

| | | |
|---|---|---|
| 5,198,367 A | 3/1993 | Aizawa et al. |
| 5,200,051 A | 4/1993 | Cozzette et al. |
| 5,202,261 A | 4/1993 | Musho et al. |
| 5,205,920 A | 4/1993 | Oyama et al. |
| 5,206,145 A | 4/1993 | Cattell |
| 5,208,154 A | 5/1993 | Weaver et al. |
| 5,217,595 A | 6/1993 | Smith et al. |
| 5,227,042 A | 7/1993 | Zawodzinski et al. |
| 5,229,282 A | 7/1993 | Yoshioka et al. |
| 5,250,439 A | 10/1993 | Musho et al. |
| 5,262,035 A | 11/1993 | Gregg et al. |
| 5,262,305 A | 11/1993 | Heller et al. |
| 5,264,103 A | 11/1993 | Yoshioka et al. |
| 5,264,106 A | 11/1993 | McAleer et al. |
| 5,266,179 A | 11/1993 | Nankai et al. |
| 5,271,815 A | 12/1993 | Wong |
| 5,272,060 A | 12/1993 | Hamamoto et al. |
| 5,278,079 A | 1/1994 | Gubinski et al. |
| 5,282,950 A | 2/1994 | Dietze et al. |
| 5,286,362 A | 2/1994 | Hoenes et al. |
| 5,286,364 A | 2/1994 | Yacynych et al. |
| 5,288,636 A | 2/1994 | Pollmann et al. |
| 5,293,546 A | 3/1994 | Tadros et al. |
| 5,310,885 A | 5/1994 | Maier et al. |
| 5,320,725 A | 6/1994 | Gregg et al. |
| 5,326,449 A | 7/1994 | Cunningham |
| 5,337,747 A | 8/1994 | Neftel |
| 5,352,348 A | 10/1994 | Young et al. |
| 5,352,351 A | 10/1994 | White et al. |
| 5,356,786 A | 10/1994 | Heller et al. |
| 5,364,797 A | 11/1994 | Olson et al. |
| 5,368,028 A | 11/1994 | Palti |
| 5,372,133 A | 12/1994 | Hogen Esch |
| 5,378,628 A | 1/1995 | Grätzel et al. |
| 5,380,422 A | 1/1995 | Negishi et al. |
| 5,382,346 A | 1/1995 | Uenoyama et al. |
| 5,384,028 A | 1/1995 | Ito |
| 5,387,327 A | 2/1995 | Khan |
| 5,390,671 A | 2/1995 | Lord et al. |
| 5,391,250 A | 2/1995 | Cheney, II et al. |
| 5,393,903 A | 2/1995 | Gratzel et al. |
| 5,395,504 A | 3/1995 | Saurer et al. |
| 5,410,474 A | 4/1995 | Fox |
| 5,411,647 A | 5/1995 | Johnson et al. |
| 5,413,690 A | 5/1995 | Kost et al. |
| 5,422,246 A | 6/1995 | Koopal et al. |
| 5,437,973 A | 8/1995 | Vadgama et al. |
| 5,437,999 A | 8/1995 | Diebold et al. |
| 5,438,271 A | 8/1995 | White et al. |
| 5,478,751 A | 12/1995 | Oosta et al. |
| 5,494,562 A | 2/1996 | Maley et al. |
| 5,496,453 A | 3/1996 | Uenoyama et al. |
| 5,497,772 A | 3/1996 | Schulman et al. |
| 5,501,956 A | 3/1996 | Wada et al. |
| 5,502,396 A | 3/1996 | Desarzens et al. |
| 5,507,288 A | 4/1996 | Böcker et al. |
| 5,508,171 A | 4/1996 | Walling et al. |
| 5,514,253 A | 5/1996 | Davis et al. |
| 5,520,787 A | 5/1996 | Hanagan et al. |
| 5,525,511 A | 6/1996 | D'Costa |
| 5,526,120 A | 6/1996 | Jina et al. |
| 5,531,878 A | 7/1996 | Vadgama et al. |
| 5,552,027 A | 9/1996 | Birkle et al. |
| 5,556,524 A | 9/1996 | Albers |
| 5,565,085 A | 10/1996 | Ikeda et al. |
| 5,567,302 A | 10/1996 | Song et al. |
| 5,568,806 A | 10/1996 | Cheney, II et al. |
| 5,569,186 A | 10/1996 | Lord et al. |
| 5,575,895 A | 11/1996 | Ikeda et al. |
| 5,580,527 A | 12/1996 | Bell et al. |
| 5,582,184 A | 12/1996 | Erickson et al. |
| 5,582,697 A | 12/1996 | Ikeda et al. |
| 5,582,698 A | 12/1996 | Flaherty et al. |
| 5,586,553 A | 12/1996 | Halili et al. |
| 5,589,045 A | 12/1996 | Hyodo |
| 5,589,326 A | 12/1996 | Deng et al. |
| 5,593,852 A | 1/1997 | Heller et al. |
| 5,596,150 A | 1/1997 | Arndt et al. |
| 5,617,851 A | 4/1997 | Lipkovker |
| 5,628,890 A | 5/1997 | Carter et al. |
| 5,650,062 A | 7/1997 | Ikeda et al. |
| 5,651,869 A | 7/1997 | Yoshioka et al. |
| 5,660,163 A | 8/1997 | Schulman et al. |
| 5,670,031 A | 9/1997 | Hintsche et al. |
| 5,680,858 A | 10/1997 | Hansen et al. |
| 5,682,233 A | 10/1997 | Brinda |
| 5,694,932 A | 12/1997 | Michel |
| 5,695,623 A | 12/1997 | Michel et al. |
| 5,708,247 A | 1/1998 | McAleer et al. |
| 5,711,861 A | 1/1998 | Ward et al. |
| 5,711,862 A | 1/1998 | Sakoda et al. |
| 5,720,862 A | 2/1998 | Hamamoto et al. |
| 5,727,548 A | 3/1998 | Hill et al. |
| 5,741,211 A | 4/1998 | Renirie et al. |
| 5,741,688 A | 4/1998 | Oxenboll et al. |
| 5,746,217 A | 5/1998 | Erickson et al. |
| 5,770,028 A | 6/1998 | Maley et al. |
| 5,781,455 A | 7/1998 | Hyodo |
| 5,791,344 A | 8/1998 | Schulman et al. |
| 5,804,048 A | 9/1998 | Wong et al. |
| 5,820,570 A | 10/1998 | Erickson et al. |
| 5,830,341 A | 11/1998 | Gilmartin |
| 5,834,224 A | 11/1998 | Ruger et al. |
| 5,837,454 A | 11/1998 | Cozzette et al. |
| 5,842,983 A | 12/1998 | Abel et al. |
| 5,846,702 A | 12/1998 | Deng et al. |
| 5,846,744 A | 12/1998 | Athey et al. |
| 5,857,983 A | 1/1999 | Douglas et al. |
| 5,879,311 A | 3/1999 | Duchon et al. |
| 5,951,836 A | 9/1999 | McAleer et al. |
| 6,004,441 A | 12/1999 | Fujiwara et al. |
| 6,033,866 A | 3/2000 | Guo et al. |
| 6,071,391 A | 6/2000 | Gotoh et al. |
| 6,120,676 A | 9/2000 | Heller et al. |
| 6,143,164 A * | 11/2000 | Heller et al. .............. 177/25.15 |
| 6,153,069 A | 11/2000 | Pottgen et al. |
| 6,200,442 B1 | 3/2001 | Markart |
| 6,461,496 B1 * | 10/2002 | Feldman et al. ......... 205/777.5 |

FOREIGN PATENT DOCUMENTS

| | | |
|---|---|---|
| EP | 0 125 139 A2 | 11/1984 |
| EP | 0 136 362 A1 | 4/1985 |
| EP | 0 170 375 A2 | 2/1986 |
| EP | 0 080 304 B1 | 5/1986 |
| EP | 0 184 909 A2 | 6/1986 |
| EP | 0 206 218 A2 | 12/1986 |
| EP | 0 230 472 A1 | 8/1987 |
| EP | 0 241 309 A3 | 10/1987 |
| EP | 0 245 073 A2 | 11/1987 |
| EP | 0 278 647 A2 | 8/1988 |
| EP | 0 286 084 A2 | 10/1988 |
| EP | 0 359 831 A1 | 3/1990 |
| EP | 0 368 209 A1 | 5/1990 |
| EP | 0 390 390 A1 | 10/1990 |
| EP | 0 400 918 A1 | 12/1990 |
| EP | 0 453 283 A1 | 10/1991 |
| EP | 0 470 290 A1 | 2/1992 |
| EP | 0 255 291 B1 | 6/1992 |
| EP | 0 537 761 A2 | 4/1993 |
| EP | 0 127 958 B2 | 4/1996 |
| EP | 0 781 406 B1 | 5/1998 |
| GB | 1394 171 | 5/1975 |

| | | |
|---|---|---|
| GB | 2 073 891 A | 10/1981 |
| GB | 2 154 003 B | 8/1985 |
| GB | 2 204 408 A | 11/1988 |
| JP | 54-41191 | 4/1979 |
| JP | 55-10581 | 1/1980 |
| JP | 55-10583 | 1/1980 |
| JP | 55-10584 | 1/1980 |
| JP | 55-12406 | 1/1980 |
| JP | 56-163447 | 12/1981 |
| JP | 57-70448 | 4/1982 |
| JP | 60-173457 | 9/1985 |
| JP | 60-173458 | 9/1985 |
| JP | 60-173459 | 9/1985 |
| JP | 61-90050 | 5/1986 |
| JP | 62-85855 | 4/1987 |
| JP | 62 114747 | 5/1987 |
| JP | 63-58149 | 3/1988 |
| JP | 63-128252 | 5/1988 |
| JP | 63-139246 | 6/1988 |
| JP | 63-294799 | 12/1988 |
| JP | 63-317758 | 12/1988 |
| JP | 1-114746 | 5/1989 |
| JP | 1-114747 | 5/1989 |
| JP | 1-134244 | 5/1989 |
| JP | 1-156658 | 6/1989 |
| JP | 2-62958 | 3/1990 |
| JP | 2-120655 | 5/1990 |
| JP | 2-287145 | 11/1990 |
| JP | 2-310457 | 12/1990 |
| JP | 3-26956 | 2/1991 |
| JP | 3-28752 | 2/1991 |
| JP | 3-202764 | 9/1991 |
| JP | 5-72171 | 3/1993 |
| JP | 5-196595 | 8/1993 |
| JP | 11-108879 * | 4/1999 |
| SU | 1281988 A1 | 1/1987 |
| WO | WO 85/05119 | 11/1985 |
| WO | WO 89/08713 | 9/1989 |
| WO | WO 90/05300 | 5/1990 |
| WO | WO 91/04704 | 4/1991 |
| WO | WO 92/13271 | 8/1992 |
| WO | WO 94/20602 | 9/1994 |
| WO | WO 94/27140 | 11/1994 |
| WO | WO 95/02817 | 1/1995 |
| WO | WO 97/00441 | 1/1997 |
| WO | WO 97/18464 | 5/1997 |
| WO | WO 97/19344 | 5/1997 |
| WO | WO 97/42882 | 11/1997 |
| WO | WO 97/42883 | 11/1997 |
| WO | WO 97/42886 | 11/1997 |
| WO | WO 97/42888 | 11/1997 |
| WO | WO 97/43962 | 11/1997 |
| WO | WO 98/35225 | 8/1998 |
| WO | WO 98/43073 | 10/1998 |
| WO | WO 98/58250 | 12/1998 |
| WO | WO 99/08106 | 2/1999 |
| WO | WO 99/30152 | 6/1999 |

OTHER PUBLICATIONS

Albery, W. J. et al., "Amperometric Enzyme Electrodes," *Phil. Trans. R. Soc. Lond.* B316:107–119 (1987).

Alcock, S. J. et al., "Continuous Analyte Monitoring to Aid Clinical Practice," *IEEE Engineering in Medicine and Biology*, 319–325 (1994).

Anderson, L. B. et al., "Thin–Layer Electrochemistry: Steady–State Methods of Studying Rate Processes," *J. Electroanal. Chem.*, 10:295–305 (1965).

Bartlett, P. N. et al., "Covalent Binding of Electron Relays to Glucose Oxidation," *J. Chem. Soc. Chem. Commun.*, 1603–1604 (1987).

Bartlett, P. N. et al., "Modification of glucose oxidase by tetrathiafulvalene," *J. Chem. Soc., Chem. Commun.*, 16 (1 page—Abstract only) (1990).

Bartlett, P. N. et al., "Strategies for the Development of Amperometric Enzyme Electrodes," *Biosensors*, 3:359–379 (1987/88).

Bobbioni–Harsch, E. et al., "Lifespan of subcutaneous glucose sensors and their performances during dynamic glycaemia changes in rats," *J. Biomed. Eng.* 15:457–463 (1993).

Brandt, J. et al., "Covalent attachment of proteins to polysaccharide carriers by means of benzoquinone," *Biochim. Biophys. Acta*, 386(1) (1 page Abstract only) (1975).

Brownlee, M. et al., "A Glucose–Controlled Insulin–Delivery System: Semisynthetic Insulin Bound to Tectin", *Science*, 206(4423):1190–1191 (Dec. 7, 1979).

Cass, A.E.G. et al., "Ferricinum Ion As An Electron Acceptor for Oxido–Reductases," *J. Electroanal. Chem.*, 190:117–127 (1985).

Cass, A.E.G. et al., "Ferrocene–Mediated Enzyme Electrode for Amperometric Determination of Glucose", *Anal. Chem.*, 56(4):667–671 (Apr. 1984).

Castner, J. F. et al., "Mass Transport and Reaction Kinetic Parameters Determined Electrochemically for Immobilized Glucose Oxidase," *Biochemistry*, 23(10):2203–2210 (1984).

Claremont, D.J. et al., "Biosensors for Continuous In Vivo Glucose Monitoring", *IEEE Engineering in Medicine and Biology Society 10th Annual International Conference*, New Orleans, Louisiana, 3 pgs. (Nov. 4–7, 1988).

Chen, C.Y. et al., "A Biocompatible Needle–Type Glucose Sensor Based on Platinum–Electroplated Carbon Electrode", *Applied Biochemistry and Biotechnology*, 36:211–226 (1992).

Chen, C.Y. et al., "Amperometric Needle–Type Glucose Sensor based on a Modified Platinum Electrode with Diminished Response to Interering Materials", *Analytica Chimica Acta*, 265:5–14 (1992).

Clark, L. C. et al., "Differential Anodic Enzyme Polarography for the Measurement of Glucose", *Oxygen Transport to Tissue: Instrumentation, Methods, and Physiology*, 127–133 (1973).

Clark, L.C., Jr. et al., "Electrode Systems for Continuous Monitoring in Cardiovascular Surgery," *Annals New York Academy of Sciences*, pp. 29–45 (1962).

Clarke, W. L., et al., "Evaluating Clinical Accuracy of Systems for Self–Monitoring of Blood Glucose," *Diabetes Care*, 10(5):622–628 (Sep.–Oct. 1987).

Csöregi, E. et al., "Design, Characterization, and One–Point in Vivo Calibration of a Subcutaneously Implanted Glucose Electrode," *Anal. Chem.* 66(19):3131–3138 (Oct. 1, 1994).

Csöregi, E. et al., "On–Line Glucose Monitoring by Using Microdialysis Sampling and Amperometric Detection Based on "Wired" Glucose Oxidase in Carbon Paste," *Mikrochim. Acta*. 121:31–40 (1995).

Davis, G., "Elecrochemical Techniques for the Development of Amperometric Biosensors", *Biosensors*, 1, 161–178 (1985).

Degani, Y. et al., "Direct Electrical Communication between Chemically Modified Enzymes and Metal Electrodes. 1. Electron Transfer from Glucose Oxidase to Metal Electrodes via Electron Relays, Bound Covalently to the Enzyme,"*J. Phys. Chem.*, 91(6):1285–1289 (1987).

Degani, Y. et al., "Direct Electrical Communication between Chemically Modified Enzymes and Metal Electrodes. 2. Methods for Bonding Electron–Transfer Relays to Glucose Oxidase and D–Amino–Acid Oxidase," *J. Am. Chem. Soc.*, 110(8):2615–2620 (1988).

Degani, Y. et al., "Electrical Communication between Redox Centers of Glucose Oxidase and Electrodes via Electrostatically and Covalently Bound Redox Polymers," *J. Am. Chem. Soc.*, 111:2357–2358 (1989).

Denisevich, P. et al., "Unidirectional Current Flow and Charge State Trapping at Redox Polymer Interfaces on Bilayer Electrodes: Principles, Experimental Demonstration, and Theory," *J. Am. Chem. Soc.*, 103(16):4727–4737 (1981).

Dicks, J. M., "Ferrocene modified polypyrrole with immobilised glucose oxidase and its application in amperometric glucose microbiosensors," *Ann. Biol. clin.*, 47:607–619 (1989).

Engstrom, R.C., "Electrochemical Pretreatment of Glassy Carbon Elecrodes", *Anal. Chem.*, 54(13):2310–2314 (Nov. 1982).

Engstrom, R.C. et al., "Characterization of Electrochemically Pretreated Glassy Carbon Electrodes", *Anal. Chem.*, 56(2):136–141 (Feb. 1984).

Ellis, C. D., "Selectivity and Directed Charge Transfer through an Electroactive Metallopolymer Film," *J. Am. Chem. Soc.*, 103(25):7480–7483 (1981).

Fischer, H. et al., "Intramolecular Electron Transfer Mediated by 4,4'–Bipyridine and Related Bridging Groups", *J. Am. Chem. Soc.*, 98(18):5512–5517 (Sep. 1, 1976).

Foulds, N.C. et al., "Enzyme Entrapment in Electrically Conducting Polymers," *J. Chem. Soc., Faraday Trans 1.*, 82:1259–1264 (1986).

Foulds, N.C. et al., "Immobilization of Glucose Oxidase in Ferrocene–Modified Pyrrole Polymers," *Anal. Chem.*, 60(22):2473–2478 (Nov. 15, 1988).

Frew, J.E. et al., "Electron–Transfer Biosensors", *Phil. Trans. R. Soc. Lond.*, B316:95–106 (1987).

Gernet, S. et al., "Fabrication and Characterization of a Planar Electrochemical Cell and Its Application as a Glucose Sensor", *Biosensors & Actuators*, 18:59–70 (1989).

Gorton, L. et al., "Selective detection in flow analysis based on the combination of immobilized enzymes and chemically modified electrodes," *Analytica Chimica Acta.*, 250:203–248 (1991).

Gregg, B. A. et al., "Cross–Linked Redox Gels Containing Glucose Oxidase for Amperometric Biosensor Applications," *Analytical Chemistry*, 62(3):258–263 (Feb. 1, 1990).

Gregg, B. A. et al., "Redox Polymer Films Containing Enzymes. 1. A Redox–Conducting Epoxy Cement: Synthesis, Characterization, and Electrocatalytic Oxidation of Hydroquinone," *J. Phys. Chem.*, 95(15):5970–5975 (1991).

Hale, P.D. et al., "A New Class of Amperometric Biosensor Incorporating a Polymeric Electron–Transfer Mediator," *J. Am. Chem. Soc.*, 111(9):3482–3484 (1989).

Harrison, D.J. et al., "Characterization of Perfluorosulfonic Acid Polymer Coated Enzyme Electrodes and a Miniaturized Integrated Potentiostat for Glucose Analysis in Whole Blood", *Anal. Chem.*, 60(19):2002–2007 (Oct. 1, 1988).

Hawkridge, F. M. et al., "Indirect Coulometric Titration of Biological Electron Transport Components," *Analytical Chemistry*, 45(7):1021–1027 (Jun. 1973).

Heineman, W.R. et al., "Measurement of Enzyme E° ' Values by Optically Transparent Thin Layer Electrochemical Cells", *Analytical Chemistry*, 47(1):79, 82–84 (Jan. 1975).

Heineman, W.R. "Spectro–electro–chemistry", *Analytical Chemistry*, 50(3):390–392, 394, 396, 398, 400, 402 (Mar. 1978).

Heller, A., "Amperometric biosensors based on three–dimensional hydrogel–forming epoxy networks," *Sensors and Actuators B*, 13–14:180–183 (1993).

Heller, A., "Electrical Connection of Enzyme Redox Centers to Electrodes," *J. Phys. Chem,*, 96(9):3579–3587 (1992).

Heller, A., "Electrical Wiring of Redox Enzymes," *Acc. Chem. Res.*, 23(5):129–134 (1990).

Ianniello, R.M. et al. "Immobilized Enzyme Chemically Modified Electrode as an Amperometric Sensor", *Anal. Chem.*, 53(13):2090–2095 (Nov. 1981).

Ianniello, R.M. et al., "Differential Pulse Voltammetric Study of Direct Electron Transfer in Glucose Oxidase Chemically Modified Graphite Electrodes", *Anal. Chem.*, 54:(7):1098–1101 (Jun. 1981).

Ikeda, T. et al., "Glucose oxidase–immobilized benzoquinone–carbon paste electrode as a glucose sensor," *Agric. Biol. Chem.*, 49(2) (1 page—Abstract only) (1985).

Johnson, J. M. et al., "Potential–Dependent Enzymatic Activity in an Enzyme Thin–Layer Cell," *Anal. Chem.* 54:1377–1383 (1982).

Johnson K. W. et al., "In Vivo Evaluation of an Electroenzymatic Glucose Sensor Implanted in Subcutaneous Tissue", *Biosensors & bioelectronics* 7:709–714 (1992).

Johnson, K.W., "Reproducible Electrodeposition of Biomolecules for the Fabrication of Miniature Electroenzymatic Biosensors", *Sensors and Actuators B Chemical*, B5:85–89 (1991).

Jönsson, G. et al., "An Amperometric Glucose Sensor Made by Modification of a Graphite Electrode Surface With Immobilized Glucose Oxidase and Adsorbed Mediator", *Biosensors*, 1:355–368 (1985).

Josowicz, M. et al., "Electrochemical Pretreatment of Thin Film Platinum Electrodes", *J. Electrochem. Soc.*, 135(1):112–115 (Jan. 1988).

Katakis, I. et al., "Electrostatic Control of the Electron Transfer Enabling Binding of Recombinant Glucose Oxidase and Redox Polyelectrolytes," *J. Am. Chem. Soc.*, 116(8):3617–3618 (1994).

Katakis, I. et al., "L–α–Glycerophosphate and L–Lactate Electrodes Based on the Electrochemical "Wiring" of Oxidases," *Analytical Chemistry*, 64(9):1008–1013 (May 1, 1992).

Kenausis, G. et al., "'Wiring' of glucose oxidase and lactate oxidase within a hydrogel made with poly(vinyl pyridine) complexed with $[Os(4,4'-dimethoxy-2,2'-bipyridine)_2 Cl]^{+/2+}$," *J. Chem. Soc., Faraday Trans.*, 92(20):4131–4136 (1996).

Kondo, T. et al., "A Miniature Glucose Sensor, Implantable in the Blood Stream", *Diabetes Care*, 5(3):218–221 (May–Jun. 1982).

Kulys, J. et al., "Mediatorless peroxidase electrode and preparation of bienzyme sensors," *Bioelectrochemistry and Bioenergetics*, 24:305–311 (1990).

Lager, W. et al., "Implantable Electrocatalytic Glucose Sensor," *Horm. Metab. Res.*, 26:526–530 (Nov. 1994).

Lee, J. et al., "A New Glucose Sensor using Microporous Enzyme Membrane", *Sensors and Actuators*, B3:215–219 (1991).

Lewandowski, J.J. et al., "Evaluation of a Miniature Blood Glucose Sensor", *Trans Am Soc Artif Intern Organs*, XXXIV: 255–258 (1988).

Linder, E. et al. "Flexible (Kapton–Based) Microsensor Arrays of High Stability for Cardiovascular Applications", *J. Chem. Soc.Faraday Trans.*, 89(2):361–367 (Jan. 21, 1993).

Maidan, R. et al., "Elimination of Electrooxidizable Interferant–Produced Currents in Amperometric Biosensors," *Analytical Chemistry*, 64(23):2889–2896 (Dec. 1, 1992).

Mann–Buxbaum, E. et al, "New Microminiaturized Glucose Sensors Using Covalent Immobilization Techniques", *Sensors and Actuators*, B1:518–522 (1990).

Mastrototaro, J.J. et al., "An Electroenzymatic Glucose Sensor Fabricated on a Flexible Substrate", *Sensors and Biosensors B Chemical*, B5:139–144 (1991).

Matthews, D.R., et al., "An Amperometric Needle–Type Glucose Sensor Tested in Rats and Man", *Original Articles*, pp. 248–252 (1988).

McKean et al., "A telemetry–Instrumentation System for Chronically Implanted Glucose and Oxygen Sensors", *IEEE Transactions of Biomedical Engineering*, 35(7):526–532 (Jul. 1988).

McNeil, C. J. et al., "Thermostable Reduced Nicotinamide Adenine Dinucleotide Oxidase: Application to Amperometric Enzyme Assay," *Anal. Chem.*, 61(1):25–29 (Jan. 1, 1989).

Miyawaki, O. et al., "Electrochemical and Glucose Oxidase Coenzyme Activity of Flavin Adenine Dinucleotide Covalently Attached to Glassy Carbon at the Adenine Amino Group", *Biochimica et Biophysica Acta*, 838:60–68 (1985).

Moatti–Sirat, D. et al., "Evaluating in vitro and in vivo the inteference of ascorbate and acetaminophen on glucose detection by a needle–type glucose sensor," *Biosensors & Bioelectronics*, 7(5):345–352 (1992).

Moatti–Sirat, D. et al., "Reduction of acetaminophen interference in glucose sensors by a composite Nafion membrane: demonstration in rats and man," *Diabetologia*, 37(6) (1 page—Abstract only) (Jun. 1994).

Moatti–Sirat, D. et al., "Towards continuous glucose monitoring: in vivo evaluation of a miniaturized glucose sensor implanted for several days in rat subcutaneous tissue," *Diabetologia*, 35(3) (1 page—Abstract only) (Mar. 1992).

Moser, I. et al., "Advanced Immobilization and Protein Techniques on thin Film Biosensors", *Sensors and Actuators*, B7:356–362 (1992).

Moussy, F. et al., "Performance of Subcutaneously Implanted Needle–Type Glucose Sensors Employing a Novel Trilayer Coating", *Anal. Chem.*, 65:2072–2077 (1993).

Nagy, G. et al., "A New Type of Enzyme Electrode: The Ascorbic Acid Eliminator Electrode," *Life Sciences*, 31(23):2611–2616 (1982).

Nakamura, S. et al., "Effect of Periodate Oxidation on the Structure and Properties of Glucose Oxidase," *Biochimica et Biophysica Acta*, 445:294–308 (1976).

Narazimhan, K. et al., "p–Benzoquinone activation of metal oxide electrodes for attachment of enzymes," *Enzyme Microb. Technol.*, 7(6) (1 page—Abstract only) (1985).

Ohara, T. J. et al., "Glucose Electrodes Based on Cross–Linked $[Os(bpy)_2Cl]^{+/2+}$ Complexed Poly(1–vinylimidazole) Films," *Analytical Chemistry*, 65(23):3512–3516 (Dec. 1, 1993).

Ohara, T. J., "Osmium Bipyridyl Redox Polymers Used in Enzyme Electrodes," *Platinum Metals Rev.*, 39(2):54–62 (Apr. 1995).

Ohara, T. J. et al., ""Wired" Enzyme Electrodes for Amperometric Determination of Glucose or Lactate in the Presence of Interfering Substances," *Analytical Chemistry*, 66(15):2451–2457 (Aug. 1, 1994).

Olievier, C. N. et al., "In vivo Measurement of Carbon Dioxide Tension with a Miniature Electrode," *Pflugers Arch.* 373:269–272 (1978).

Paddock, R. et al., "Electrocatalytic reduction of hydrogen peroxide via direct electron transfer from pyrolytic graphite electrodes to irreversibly adsorbed cytochrome c peroxidase," *J. Electroanal. Chem.*, 260:487–494 (1989).

Palleschi, G. et al., "A Study of Interferences in Glucose Measurements in Blood by Hydrogen Peroxide Based Glucose Probes", *Anal. Biochem.*, 159:114–121 (1986).

Palleschi, G. et al., "Ideal Hydrogen Peroxide–Based Glucose Sensor", *Applied Biochemisry and Biotechnology*, 31:21–35 (1991).

Pankratov, I. et al., "Sol–gel derived renewable–surface biosensors," *Journal of Electroanalytical Chemistry*, 393:35–41 (1995).

Pathak, C. P. et al., "Rapid Photopolymerization of Immunoprotective Gels in Contact with Cells and Tissue," *J. Am. Chem. Soc.*, 114(21):8311–8312 (1992).

Pickup, J. et al., "Potentially–implantable, amperometric glucose sensors with mediated electron transfer: improving the operating stability," *Biosensors*, 4(2) (1 page—Abstract only) (1989).

Pishko, M.V. et al., "Amperometric Glucose Microelectrodes Prepared Through Immobilization of Glucose Oxidase in Redox Hydrogels", *Anal. Chem.*, 63(20):2268–2272 (Oct. 15, 1991).

Poitout, V. et al., "A glucose monitoring system for on line estimation in man of blood glucose concentration using a miniaturized glucose sensor implanted in the subcutaneous tissue and a wearable control unit," *Diabetolgia*, 36(7) (1 page—Abstract only) (Jul. 1993).

Poitout, V. et al., "Calibration in dogs of a subcutaneous miniaturized glucose sensor using a glucose meter for blood glucose determination," *Biosensors & Bioelectronics*, 7:587–592 (1992).

Poitout, V. et al., "In vitro and in vivo evaluation in dogs of a miniaturized glucose sensor," *ASAIO Transactions*, 37(3) (1 page—Abstract only) (Jul.–Sep. 1991).

Pollack, A. et al., "Enzyme Immobilization by Condensation Copolymerization into Cross–Linked Polyacrylamide Gels," *J. Am. Chem. Soc.*, 102(20):6324–6336 (1980).

Pons, B. S. et al., "Application of Deposited Thin Metal Films as Optically Transparent Electrodes for Internal Reflection Spectrometric Observation of Electrode Solution Interfaces", *Analytical Chemistry*, 39(6):685–688, (May 1967).

Reach, G. et al., "A Method for Evaluating in vivo the Functional Characteristics of Glucose Sensors", *Biosensors* 2:211–220 (1986).

Reach, G. et al., "Can Continuous Glucose Monitoring Be Used for the Treatment of Diabetes?" *Analytical Chemistry*, 64(6):381–386 (Mar. 15, 1992).

Rebrin, K. et al., "Automated Feedback Control of Subcutaneous Glucose Concentration in Diabetic Dogs", *Diabetologia*, 32(8):573–576 (Aug. 1989).

Sasso, S.V. et al., "Electropolymerized 1,2–Diaminobenzene as a Means to Prevent Interferences and Fouling and to Stabilize Immobilzed Enzyme in Electrochemical Biosensors", *Anal. Chem.*, 62(11):1111–1117 (Jun. 1, 1990).

Schalkhammer, T. et al, "Electrochemical Glucose Sensors on Permselective Non–conducting Substituted Pyrrole Polymers", *Sensors and Actuators*, B4:273–281 (1991).

Scheller, F. et al., "Enzyme electrodes and their application," *Phil. Trans. R. Soc. Lond.*, B 316:85–94 (1987).

Shichiri, M. et al., "Glycaemic Control in Pancreatetomized Dogs with a Wearable Artificial Endocrine Pancreas", *Diabetologia*, 24(3):179–184 (Mar. 1983).

Shigeru, T. et al, "Simultaneous Determination of Glucse and 1,5–= Anydroglucitol", *Chemical Abstracts*, 111:394 (1989).

Sittampalam, G. et al., "Surface–Modified Electrochemical Detector for Liquid Chromatography", *Anal. Chem.*, 55(9):108–1610 (Aug. 1983).

Soegijoko, S. et al., *Horm. Metabl. Res., Suppl. Ser*, 12 (1 page—Abstract only) (1982).

Sprules, S. D. et al., "Evaluation of a New Disposable Screen–Printed Sensor Strip for the Measurement of NADH and Its Modification to Produce a Lactate Biosensor Employing Microliter Volumes," *Electroanalysis*, 8(6):539–543 (1996).

Sternberg, F. et al., "Calibration Problems of Subcutaneous Glucosensors when Applied "In–Situ" in Man," *Horm. metabl. Res*, 26:523–525 (1994).

Sternberg, R. et al., "Covalent Enzyme Coupling on Cellulose Acetate Membranes for Glucose Sensor Development," *Analytical Chemistry*, 60(24):2781–2786 (Dec. 15, 1988).

Suekane, M., "Immobilization of glucose isomerase," *Zeitschrift für Allgemeine Mikrobiologie*, 22(8):565–576 (1982).

Tarasevich, M.R. "Bioelectrocatalysis", *Comprehensive Treatise of Electrochemistry*, 10 (Ch. 4):231–295 (1985).

Taylor, C. et al., "'Wiring' of glucose oxidase within a hydrogel made with polyvinyl imidazole complexed with [(Os–4,4'–dimethoxy–2,2'–bipyridine)C1]$^{+/2+}$," *Journal of Electroanalytical Chemistry*, 396:511–515 (1995).

Trojanowicz, M. et al., "Enzyme Entrapped Polypyrrole Modified Electrode for Flow–Injection Determination of Glucose," *Biosensors & Bioelectronics*, 5:149–156 (1990).

Turner, A.P.E. et al., "Diabetes Mellitus: Biosensors for Research and Management", *Bioensors*, 1:85–115 (1985).

Turner, R. F. B. et al., "A Biocompatible Enzyme Electrode for Continuous in vivo Glucose Monitoring in Whole Blood," *Sensors and Actuators*, B1(1–6):561–564 (Jan. 1990).

Umaha, M., "Protein–Modified Electrochemically Active Biomaterial Surface," *U.S. Army Research Office Report*, (12 pages) (Dec. 1988).

Urban, G. et al., "Miniaturized Thin–Film Biosensors Using Covalently Immobilized Glucose Oxidase", *Biosensors & Bioelectronics*, 6(7):555–562 (1991).

Velho, G. et al., "Strategies for calibrating a subcutaneous glucose sensor," *Biomed. Biochin. Acta*, 48(11/12):957–964 (1989).

Von Woedtke, T. et al., "In Situ Calibration of Implanted Electrochemical Glucose Sensors," *Biomed. Biochim. Acta*, 48(11/12):943–952 (1989).

Vreeke, M. S. et al., "Chapter 15: Hydrogen Peroxide Electrodes Based on Electrical Connection of Redox Centers of Varions Peroxidases to Electrodes through a Three–Dimensional Electron–Relaying Polymer Network" *Diagnostic Biosensor Polymers*, 7 pgs. (Jul. 26, 1993).

Vreeke, M. et al., "Hydrogen Peroxide and β–Nicotinamide Adenine Dinucleotide Sensing Amperometric Electrodes Based on Electrical Connection of Horseradish Peroxidase Redox Centers to Electrodes through a Three–Dimensional Electron Relaying Polymer Network," *Analytical Chemistry*, 64(24):3084–3090 (Dec. 15, 1992).

Wang, J. et al., "Activation of Glassy Carbon Electrodes by Alternating Current Electrochemical Treatment", *Analytica Chimica Acta*, 167:325–334 (Jan. 1985).

Wang, J. et al., "Amperometric biosensing of organic peroxides with peroxidase–modified electrodes," *Analytica Chimica Acta*. 254:81–88 (1991).

Wang, J. et al., "Screen–Printable Sol–Gel Enzyme–Containing Carbon Inks," *Analytical Chemistry*, 68(15):2705–2708 (Aug. 1, 1996).

Wang, J. et al., "Sol–Gel–Derived Metal–Dispersed Carbon Composite Amperometric Biosensors," *Electroanalysis*, 9(1):52–55 (1997).

Williams, D.L. et al., "Electrochemical–Enzymatic Analysis of Blood Glucose and Lactate", *Anal. Chem.*, 42(1):118–121 (Jan. 1970).

Yabuki, S. et al., "Electro–conductive Enzyme Membrane," *J. Chem. Soc. Chem. Commun*, 945–946 (1989).

Yamasaki, Y., "The Development of a Needle–Type Glucose Sensor for Wearable Artificial Endocrine Pancreas", *Medical Journal of Osaka University*, vol. 35, No. 1–2, pp. 24–34 (Sep. 1994).

Yang, L. et al., "Determination of Oxidase Enzyme Substrates Using Cross–Flow Thin–Layer Amperometry," *Electroanalysis*, 8(8–9):716–721 (1996).

Yao, S.J. et al., "The Interference of Ascorbate and Urea in Low–Potential Electrochemical Glucose Sensing", *Proceedings of the Twelfth Annual International Conference of the IEEE Engineering in Medicine and Biology Society*, 12(2):487–489 (Nov. 1–4, 1990).

Yao, T. et al., "A Chemically–Modified Enzyme Membrane Electrode As An Amperometric Glucose Sensor," *Analytica Chimica Acta.*, 148:27–33 (1983).

Ye, L. et al., "High Current Density "Wired" Quinoprotein Glucose Dehydrogenase Electrode," *Anal. Chem.*, 65(3):238–241 (Feb. 1, 1993).

Yildiz, A., "Evaluation of an Improved Thin–Layer Electrode", *Analytical Chemistry*, 40(7):1018–1024 (Jun. 1968).

Zamzow, K. et al., New Wearable Continuous Blood Glucose Monitor (BGM) and Artificial Pancreas (AP), *Diabetes*, 39:5A(20) (May 1990).

\* cited by examiner

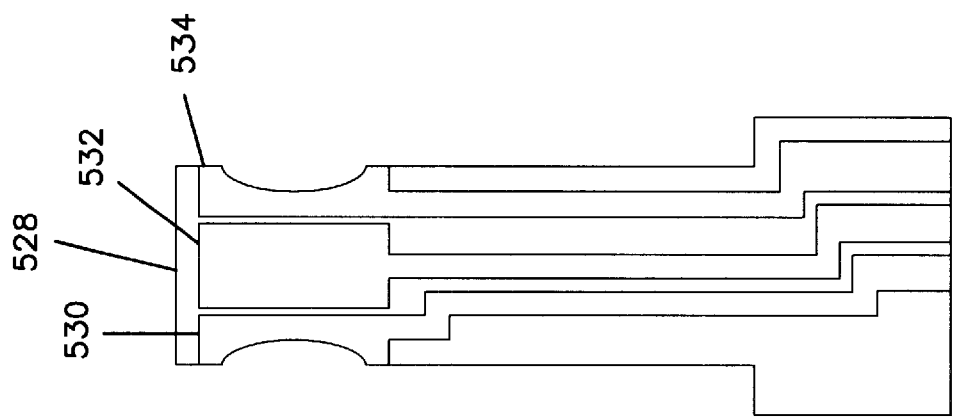
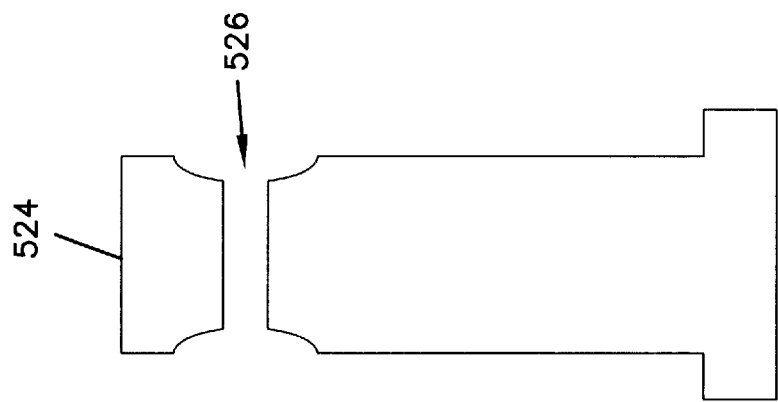
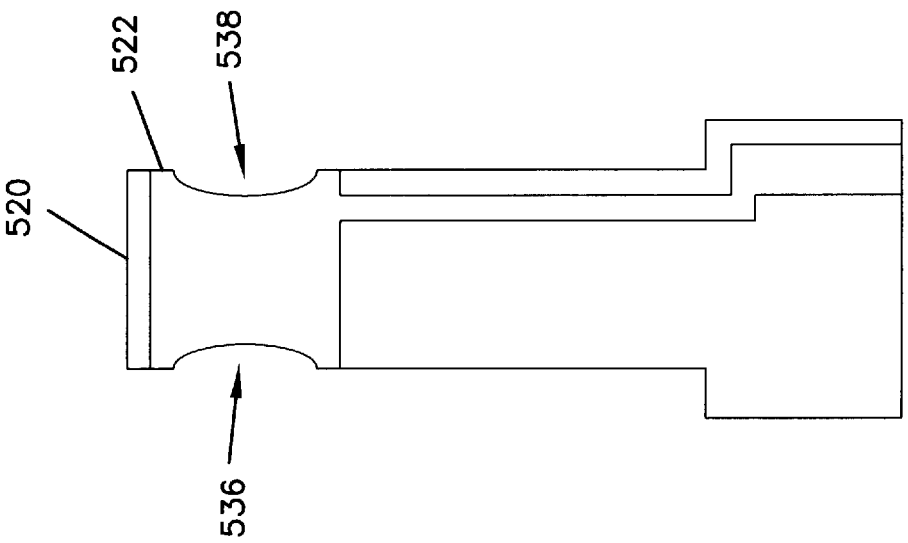

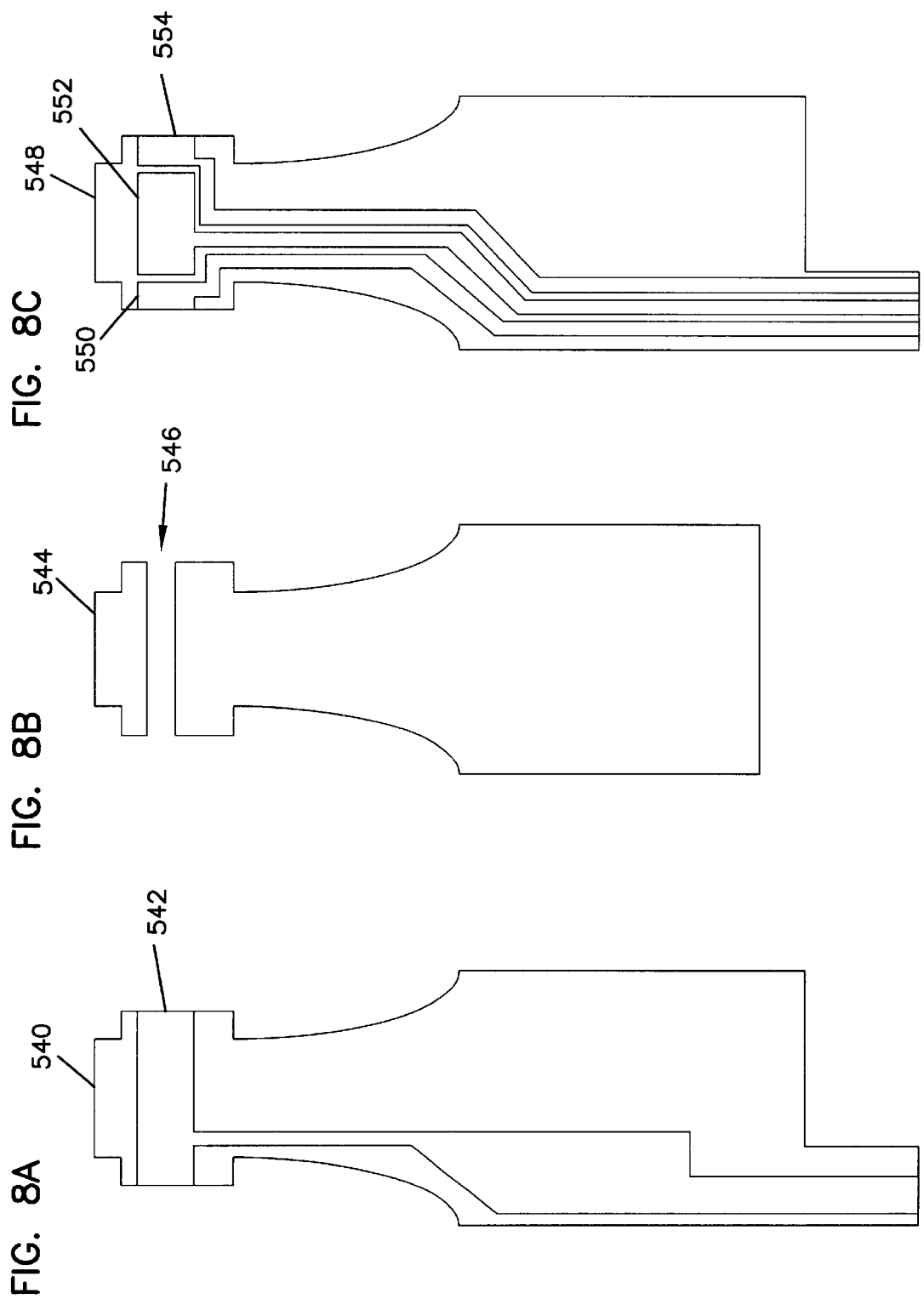

FIG. 10A
FIG. 10B
FIG. 10C
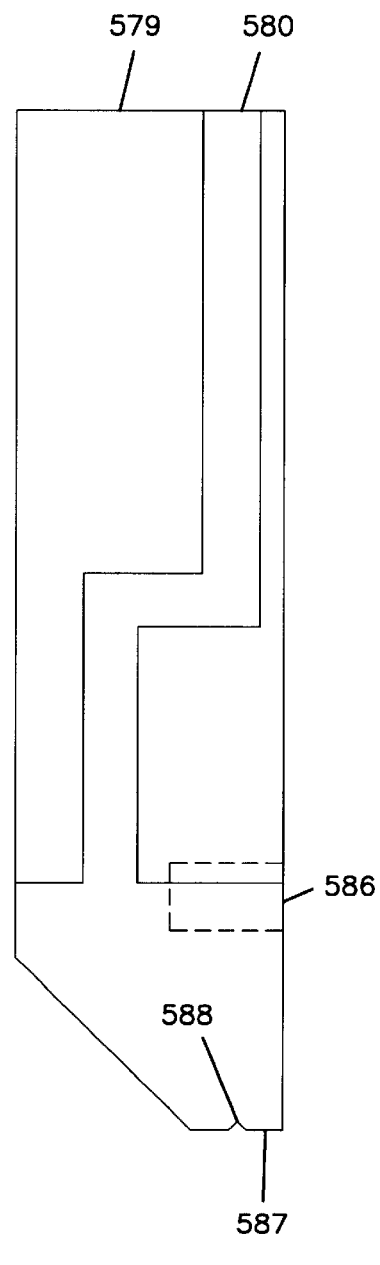
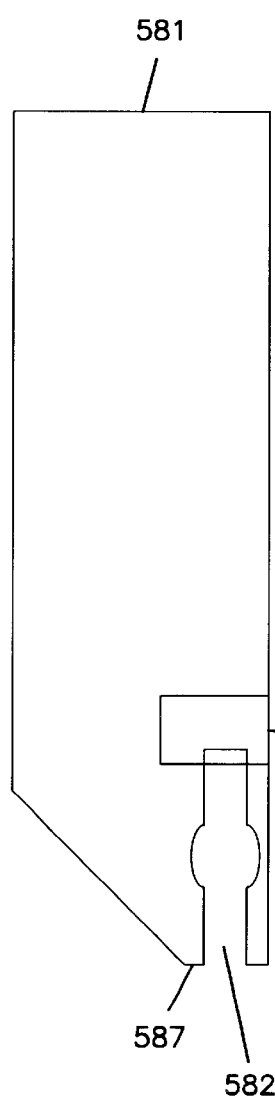
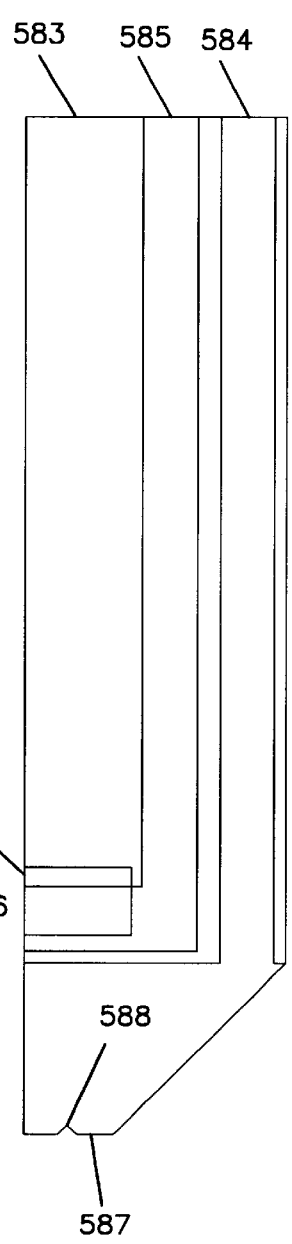

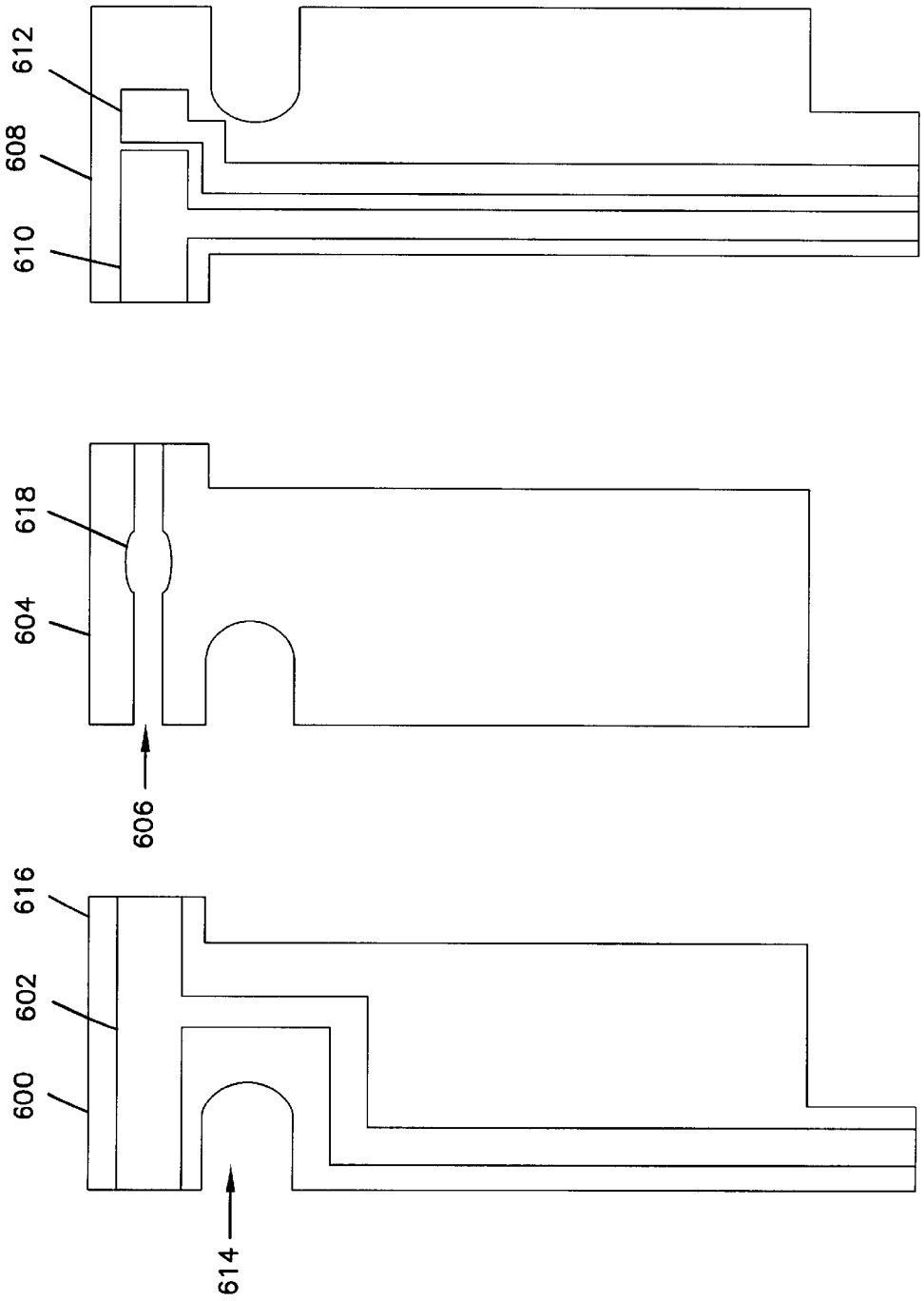

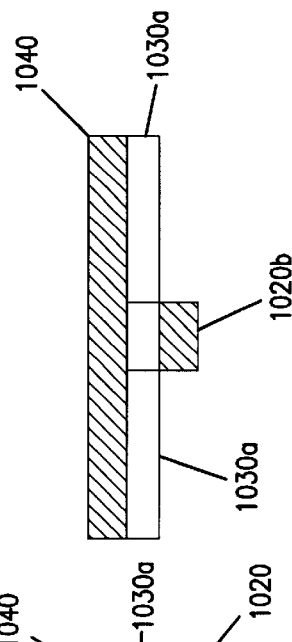
FIG. 14C
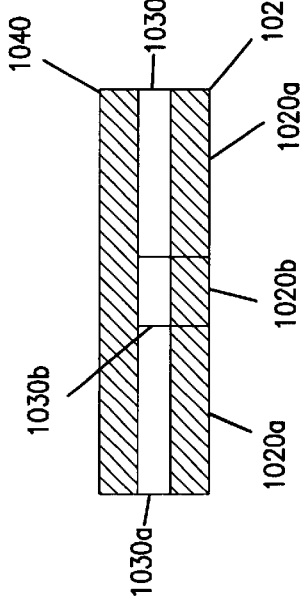
FIG. 14B
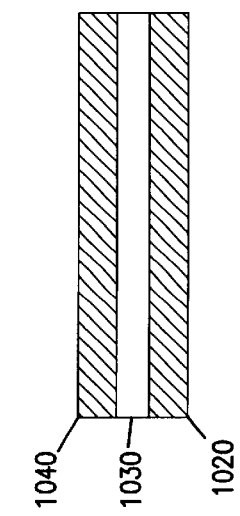
FIG. 14A
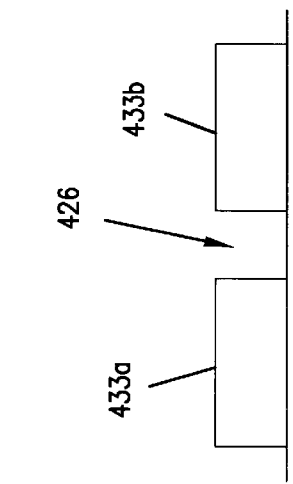
FIG. 14F
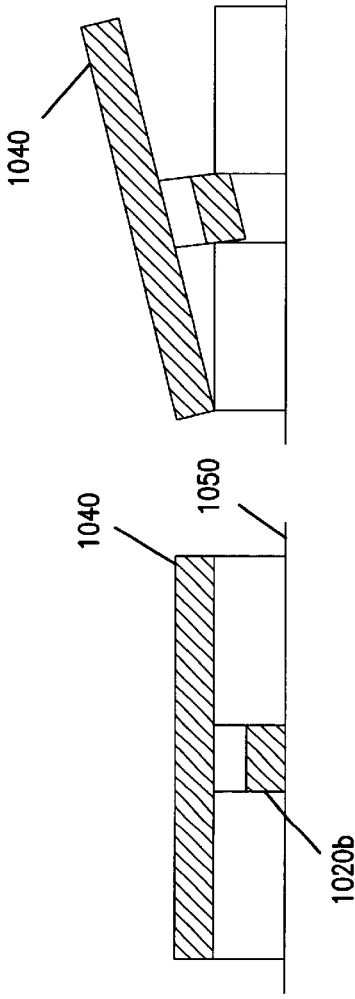
FIG. 14E
FIG. 14D

SMALL VOLUME IN VITRO ANALYTE SENSOR AND METHODS

FIELD OF THE INVENTION

This invention relates to analytical sensors for the detection of bioanalytes in a small volume sample, and methods of making and using the sensors.

BACKGROUND

Analytical sensors are useful in chemistry and medicine to determine the presence and concentration of a biological analyte. Such sensors are needed, for example, to monitor glucose in diabetic patients and lactate during critical care events.

Currently available technology measures bioanalytes in relatively large sample volumes, e.g., generally requiring 3 microliters or more of blood or other biological fluid. These fluid samples are obtained from a patient, for example, using a needle and syringe, or by lancing a portion of the skin such as the fingertip and "milking" the area to obtain a useful sample volume. These procedures are inconvenient for the patient, and often painful, particularly when frequent samples are required. Less painful methods for obtaining a sample are known such as lancing the arm or thigh, which have a lower nerve ending density. However, lancing the body in the preferred regions typically produces submicroliter samples of blood, because these regions are not heavily supplied with near-surface capillary vessels.

It would therefore be desirable and very useful to develop a relatively painless, easy to use blood analyte sensor, capable of performing an accurate and sensitive analysis of the concentration of analytes in a small volume of sample.

It would also be desirable to develop methods for manufacturing small volume electrochemical sensors capable of decreasing the errors that arise from the size of the sensor and the sample.

SUMMARY OF THE INVENTION

The sensors of the present invention provide a method for the detection and quantification of an analyte in submicroliter samples. In general, the invention includes a method and sensor for analysis of an analyte in a small volume of sample by, for example, coulometry, amperometry and/or potentiometry. A sensor of the invention preferably utilizes a non-leachable or diffusible redox mediator. The sensor also includes a sample chamber to hold the sample in electrolytic contact with the working electrode. In many instances, the sensor also contains a non-leachable or diffusible second electron transfer agent.

In a preferred embodiment, the working electrode faces a counter electrode, forming a measurement zone within the sample chamber, between the two electrodes, that is sized to contain no more than about 1 µL of sample, preferably no more than about 0.5 µL, more preferably no more than about 0.32 µL, still more preferably no more than about 0.25 µL, and most preferably no more than about 0.1 µL of sample.

In one embodiment of the invention, a sensor, configured for insertion into an electronic meter, is provided with a working electrode and a counter electrode, and a conductive insertion monitor which provides electrical contact with the electronic meter if the sensor is properly inserted into the meter. The conductive insertion monitor is configured and arranged to close an electrical circuit when the sensor is properly inserted into the electronic connector.

In another embodiment of the invention, a sensor is provided with a plurality of contacts, each contact having a contact pad, which is a region for connection with an electronic meter. The plurality of contacts and contact pads are disposed on a substrate having a length and a width, and each contact pad has a contact pad width taken parallel to the width of the substrate. The sum of the contact pad widths is greater than the width of the substrate. In a preferred embodiment, six electrical connections are made with six contact pads on the sensor but in a width that is approximately the width of four contact pads. For example, a working electrode, three counter electrodes (e.g., one counter electrode and two indicator electrodes), and two insertion trace connections each have a contact pad; connection can be made to each of these six contact pads in the same width of the contact pads of the working electrode and three counter electrodes.

The present invention also includes an electrical connector, for providing electrical contact between a sensor and an electrical meter or other device. The electrical connector has a plurality of contact structures, each which has a proximal contact end for electrical connection to a sensor contact, and a distal end for electrical connection to the electrical device. In one embodiment, a plurality of first contact structures extend longitudinally parallel from the distal to the proximal end. Additionally, one or more second contract structures extend longitudinally next to the first contact structures, from the distal end past the proximal end of the first contact structures, and angle toward a longitudinal center line of the connector. Contact to the sensor is then made via the proximal contact ends.

Preferably, the electrical connector has at least two second contact structures extending longitudinally past the proximal end of the first contact structures and angling toward the longitudinal center line of the connector. After the angled or bent portion, the proximal contact ends of the second contact structures of one embodiment make electrical contact with a single conductive surface of a sensor, such as a conductive insertion monitor. In another aspect, the first contact structures can be configured and arranged to contact one or more working and/or counter electrodes of a sensor, and the second contact structures are configured and arranged to contact one or more conductive insertion monitors.

The sensors of the present invention can be configured for side-filling or tip-filling. In addition, in some embodiments, the sensor may be part of an integrated sample acquisition and analyte measurement device. The integrated sample acquisition and analyte measurement device can include the sensor and a skin piercing member, so that the device can be used to pierce the skin of a user to cause flow of a fluid sample, such as blood, that can then be collected by the sensor. In at least some embodiments, the fluid sample can be collected without moving the integrated sample acquisition and analyte measurement device.

In one embodiment, the sensor is connected with an electrical device, to provide a processor coupled to the sensor. The processor is configured and arranged to determine, during electrolysis of a sample in the sample chamber, a series of current values. The processor determines a peak current value from the series of current values. After the current values decrease below a threshold fraction of the peak current values, slope values are determined from the current values and represent a linear function of the logarithm of current values over time. The processor determines, from the slope values, an extrapolation slope. From the extrapolated slope and the measured current values, the processor determines an amount of charge needed to electrolyze the sample and, from that amount of charge, the concentration of the analyte in the sample.

One method of forming a sensor, as described above, includes forming at least one working electrode on a first substrate and forming at least one counter or counter/reference electrode on a second substrate. A spacer layer is disposed on either the first or second substrates. The spacer layer defines a chamber into which a sample can be drawn and held when the sensor is completed. A redox mediator and/or second electron transfer agent can be disposed on the first or second substrate in a region that will be exposed within the sample chamber when the sensor is completed. The first and second substrates are then brought together and spaced apart by the spacer layer with the sample chamber providing access to the at least one working electrode and the at least one counter or counter/reference electrode. In some embodiments, the first and second substrates are portions of a single sheet or continuous web of material. The invention includes particularly efficient and reliable methods for the manufacture of these sensors.

One such efficient and reliable method includes providing an adhesive having first and second surfaces covered with first and second release liners and then making detailed cuts through the first release liner and the adhesive but not through the second release liner. These cuts define one or more sample chamber regions. A portion of the first release liner is removed to expose a portion of the first adhesive surface, which leaves a remaining portion of the first release liner over the sample chamber regions. This exposed first adhesive surface is applied to a first substrate having one or more conductive traces disposed thereon. The second release liner is removed together with the adhesive and the first release liner of the sample chamber regions in order to expose the second adhesive surface. The second adhesive surface is then applied to a second substrate having one or more conductive traces disposed thereon. This method forms a sensor having a sample chamber corresponding to one of the sample chamber regions.

These and various other features which characterize the invention are pointed out with particularity in the attached claims. For a better understanding of the invention, its advantages, and objectives obtained by its use, reference should be made to the drawings and to the accompanying description, in which there is illustrated and described preferred embodiments of the invention.

BRIEF DESCRIPTION OF THE DRAWINGS

Referring now to the drawings, wherein like reference numerals and letters indicate corresponding structure throughout the several views:

FIG. 7A illustrates a top view of a first film with a working electrode for use in a sixth embodiment of a sensor according to the invention;

FIG. 7B illustrates a top view of a spacer for placement on the first film of FIG. 7A;

FIG. 7C illustrates a bottom view of a second film (inverted with respect to FIGS. 7A and 7B) with counter electrodes placement over the spacer of FIG. 7B and first film of FIG. 7A;

FIG. 8A illustrates a top view of a first film with a working electrode for use in a seventh embodiment of a sensor according to the invention;

FIG. 8B illustrates a top view of a spacer for placement on the first film of FIG. 8A;

FIG. 8C illustrates a bottom view of a second film (inverted with respect to FIGS. 8A and 8B) with counter electrodes placement over the spacer of FIG. 8B and first film of FIG. 8A;

FIG. 10A illustrates a top view of a first film with a working electrode for use in a ninth embodiment of a sensor according to the invention;

FIG. 10B illustrates a top view of a spacer for placement on the first film of FIG. 10A;

FIG. 10C illustrates a bottom view of a second film (inverted with respect to FIGS. 10A and 10B) with counter electrodes placement over the spacer of FIG. 10B and first film of FIG. 10A;

FIG. 12A illustrates a top view of a first film with a working electrode for use in a eleventh embodiment of a sensor according to the invention;

FIG. 12B illustrates a top view of a spacer for placement on the first film of FIG. 12A;

FIG. 12C illustrates a bottom view of a second film (inverted with respect to FIGS. 12A and 12B) with counter electrodes placement over the spacer of FIG. 12B and first film of FIG. 12A;

FIGS. 14A through 14F illustrate cross sectional views of a sequential process of providing a sample chamber in a spacer layer;

DETAILED DESCRIPTION OF THE PREFERRED EMBODIMENT

Figure 1:
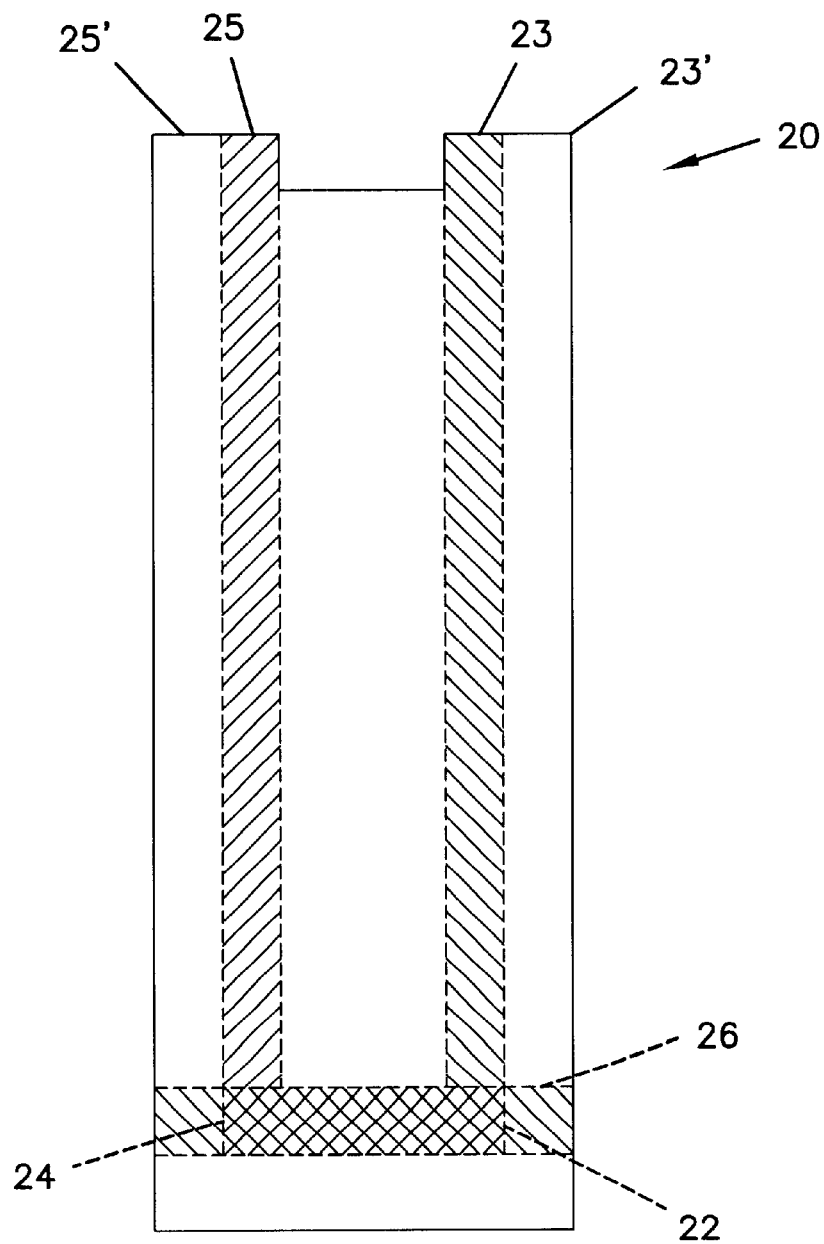
FIG. 1 is a schematic view of a first embodiment of an electrochemical sensor in accordance with the present invention having a working electrode and a counter electrode facing each other and having a sample chamber.

As used herein, the following definitions define the stated term:

An "air-oxidizable mediator" is a redox mediator that is oxidized by air, preferably so that at least 90% of the mediator is in an oxidized state upon storage in air either as a solid or as a liquid during a period of time, for example, one month or less, and, preferably, one week or less, and, more preferably, one day or less.

"Amperometry" includes steady-state amperometry, chronoamperometry, and Cottrell-type measurements.

A "biological fluid" is any body fluid in which the analyte can be measured, for example, blood (which includes whole blood and its cell-free components, such as, plasma and serum), interstitial fluid, dermal fluid, sweat, tears, urine and saliva.

"Coulometry" is the determination of charge passed or projected to pass during complete or nearly complete electrolysis of the analyte, either directly on the electrode or through one or more electron transfer agents. The charge is determined by measurement of charge passed during partial or nearly complete electrolysis of the analyte or, more often, by multiple measurements during the electrolysis of a decaying current and elapsed time. The decaying current results from the decline in the concentration of the electrolyzed species caused by the electrolysis.

A "counter electrode" refers to one or more electrodes paired with the working electrode, through which passes an electrochemical current equal in magnitude and opposite in sign to the current passed through the working electrode. The term "counter electrode" is meant to include counter electrodes which also function as reference electrodes (i.e. a counter/reference electrode) unless the description provides that a "counter electrode" excludes a reference or counter/reference electrode.

An "effective diffusion coefficient" is the diffusion coefficient characterizing transport of a substance, for example, an analyte, an enzyme, or a redox mediator, in the volume between the electrodes of the electrochemical cell. In at least some instances, the cell volume may be occupied by more than one medium (e.g., the sample fluid and a polymer film). Diffusion of a substance through each medium may occur at a different rate. The effective diffusion coefficient corresponds to a diffusion rate through this multiple-media volume and is typically different than the diffusion coefficient for the substance in a cell filled solely with sample fluid.

An "electrochemical sensor" is a device configured to detect the presence of and/or measure the concentration of an analyte via electrochemical oxidation and reduction reactions. These reactions are transduced to an electrical signal that can be correlated to an amount or concentration of analyte.

"Electrolysis" is the electrooxidation or electroreduction of a compound either directly at an electrode or via one or more electron transfer agents (e.g., redox mediators and/or enzymes).

The term "facing electrodes" refers to a configuration of the working and counter electrodes in which the working surface of the working electrode is disposed in approximate opposition to a surface of the counter electrode. In at least some instances, the distance between the working and counter electrodes is less than the width of the working surface of the working electrode.

A compound is "immobilized" on a surface when it is entrapped on or chemically bound to the surface.

An "indicator electrode" is an electrode that detects partial or complete filling of a sample chamber and/or measurement zone.

A "layer" is one or more layers.

The "measurement zone" is defined herein as a region of the sample chamber sized to contain only that portion of the sample that is to be interrogated during an analyte assay.

A "non-diffusible," "non-leachable," or "non-releasable" compound is a compound which does not substantially diffuse away from the working surface of the working electrode for the duration of the analyte assay.

The "potential of the counter/reference electrode" is the half cell potential of the reference electrode or counter/reference electrode of the cell when the solution in the cell is 0.1 M NaCl solution at pH7.

A "redox mediator" is an electron transfer agent for carrying electrons between the analyte and the working electrode, either directly, or via a second electron transfer agent.

A "reference electrode" includes a reference electrode that also functions as a counter electrode (i.e., a counter/ reference electrode) unless the description provides that a "reference electrode" excludes a counter/reference electrode.

A "second electron transfer agent" is a molecule that carries electrons between a redox mediator and the analyte.

A "surface in the sample chamber" is a surface of a working electrode, counter electrode, counter/reference electrode, reference electrode, indicator electrode, a spacer, or any other surface bounding the sample chamber.

A "working electrode" is an electrode at which analyte is electrooxidized or electroreduced with or without the agency of a redox mediator.

A "working surface" is the portion of a working electrode that is covered with non-leachable redox mediator and exposed to the sample, or, if the redox mediator is diffusible, a "working surface" is the portion of the working electrode that is exposed to the sample.

The small volume, in vitro analyte sensors of the present invention are designed to measure the concentration of an analyte in a portion of a sample having a volume no more than about 1 $\mu$L, preferably no more than about 0.5 $\mu$L, more preferably no more than about 0.32 $\mu$L, still more preferably no more than about 0.25 $\mu$L, and most preferably no more than about 0.1 $\mu$L of sample.

The analyte of interest is typically provided in a solution or biological fluid, such as blood or serum.

Figure 2:
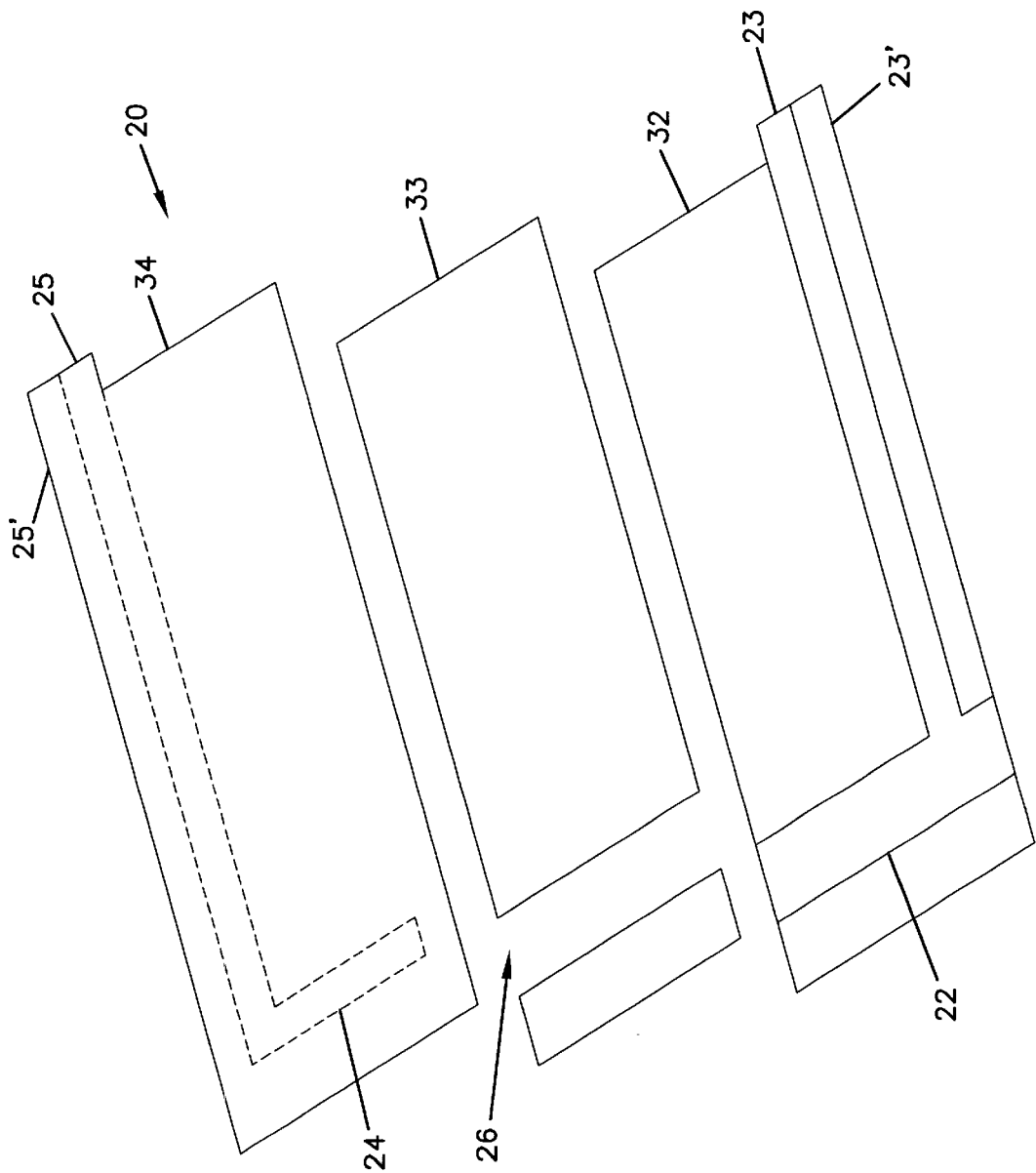
FIG. 2 is an exploded view of the sensor shown in FIG. 1, the layers illustrated individually.

Referring to the Drawings in general, and in particular FIGS. 1 and 2, a small volume in vitro electrochemical sensor 20 of the invention generally includes a working electrode 22 on a first substrate 32, a counter (or counter/reference) electrode 24 on a second substrate 34, and a sample chamber 26. The sample chamber 26 is configured so that when a sample is provided in the chamber, the sample is in electrolytic contact with both the working electrode 22, the counter electrode 24 and any reference electrodes or indicator electrodes that may be present. This allows electrical current to flow between the electrodes to effect the electrolysis (electrooxidation or electroreduction) of the analyte. A spacer 33 is positioned between first substrate 32 and second substrate 34 to provide a spacing between electrodes 22, 24 and to provide sample chamber 26 in which the sample to be evaluated is housed.

Working Electrode

The working electrode 22 may be formed from a molded carbon fiber composite or it may include an inert non-conducting base material, such as polyester, upon which a suitable conducting layer is deposited. The conducting layer typically has relatively low electrical resistance and is typically electrochemically inert over the potential range of the sensor during operation. Suitable conducting layers include gold, carbon, platinum, ruthenium dioxide, palladium, and conductive epoxies, such as, for example, ECCOCOAT CT5079-3 Carbon-Filled Conductive Epoxy Coating (available from W.R. Grace Company, Woburn, Mass.), as well as other non-corroding materials known to those skilled in the art. The electrode (e.g., the conducting layer) is deposited on the surface of the inert material by methods such as vapor deposition or printing. Preferably, the electrode is printed onto the base material.

The inert non-conducting base material, is also referred to as a substrate, base, or the like. This base material is typically an electrically non-conducting material, e.g., any insulating material, that is not capable of carrying electric charge or current. Examples of materials usable as the base material for sensors of the present invention include polyesters, polyethylene (both high density and low density), polyethylene terephthalate, polycarbonate, vinyls, and the like. The base material can be treated with a primer or other such coating to improve the adhesion of the electrodes thereon.

A tab 23' can be provided on the end of the working electrode 22 for easy connection of the electrode to external electronics (not shown) such as a voltage source or current measuring equipment. Contact pad 23, which is connected to working electrode 22, such as an extension from the working electrode, can be positioned on tab 23'.

To prevent electrochemical reactions from occurring on portions of the working electrode not coated by the mediator, when a non-leachable mediator is used, a dielectric or other insulating material can be deposited on the electrode over, under, or surrounding the region with the redox mediator. Suitable dielectric materials include waxes and non-conducting organic polymers, such as polyethylene. The dielectric material can also cover a portion of the redox mediator on the electrode. The covered portion of the redox mediator will not contact the sample, and, therefore, will not be a part of the electrode's working surface.

Sensing Chemistry

In addition to the working electrode 22, sensing chemistry materials are provided in the sample chamber 26 for the analysis of the analyte. This sensing chemistry preferably includes a redox mediator and a second electron transfer mediator, although in some instances, one or the other may be used alone. The redox mediator and second electron transfer agent can be independently diffusible or non-leachable (i.e., non-diffusible) such that either or both may be diffusible or non-leachable. Placement of sensor chemistry components can depend on whether they are diffusible or non-leachable. For example, non-leachable and/or diffusible component(s) typically form a sensing layer on the working electrode. Alternatively, one or more diffusible components can be disposed on any surface in the sample chamber prior to the introduction of the sample. As another example, one or more diffusible component(s) are placed in the sample prior to introduction of the sample into the sensor.

If the redox mediator is non-leachable, then the non-leachable redox mediator is typically disposed on the working electrode 22 as a sensing layer. In an embodiment having a redox mediator and a second electron transfer agent, if the redox mediator and second electron transfer agent are both non-leachable, then both of the non-leachable components are disposed on the working electrode 22 as a sensing layer.

If, for example, the second electron transfer agent is diffusible and the redox mediator is non-leachable, then at least the redox mediator is disposed on the working electrode 22 as a sensing layer. The diffusible second electron transfer agent need not be disposed on a sensing layer of the working electrode, but can be disposed on any surface of the sample chamber, including within the redox mediator sensing layer, or can be placed in the sample. If the redox mediator is diffusible, then the redox mediator can be disposed on any surface of the sample chamber or can be placed in the sample. If both the redox mediator and second electron transfer agent are diffusible, then the diffusible components can be independently or jointly disposed on any surface of the sample chamber and/or placed in the sample (i.e., each diffusible component need not be disposed on the same surface of the sample chamber or placed in the sample).

The redox mediator, whether it is diffusible or non-leachable, mediates a current between the working electrode 22 and the analyte and enables the electrochemical analysis of molecules which may not be suited for direct electrochemical reaction on an electrode. The mediator functions as an electron transfer agent between the electrode and the analyte.

Analytes that can be interrogated include, for example, glucose, acetyl choline, amylase, bilirubin, cholesterol, chorionic gonadotropin, creatine kinase (e.g., CK-MB), creatine, DNA, fructosamine, glucose, glutamine, growth hormones, hormones, ketones, lactate, peroxide, prostate-specific antigen, prothrombin, RNA, thyroid stimulating hormone, and troponin. The concentration of analytes such as drugs or medication, such as, for example, antibiotics (e.g., gentamicin, vancomycin, and the like), digitoxin, digoxin, drugs of abuse, theophylline, and warfarin, can also be determined. Assays suitable for determining the concentration of DNA and/or RNA are disclosed in U.S. patent applications Ser. No. 09/138,888, now issued as U.S. Pat. Nos. 6,281,006, and 09/145,776 allowed and described in PCT Application PCT/US99/14460, all which are incorporated herein by reference.

Redox Mediators

Although any organic or organometallic redox species can be used as a redox mediator, one type of suitable redox mediator is a transition metal compound or complex. Examples of suitable transition metal compounds or complexes include osmium, ruthenium, iron, and cobalt compounds or complexes. In these complexes, the transition metal is coordinatively bound to one or more ligands. The ligands are typically mono-, di-, tri-, or tetradentate. The most preferred ligands are heterocyclic nitrogen compounds, such as, for example, pyridine and/or imidazole derivatives. Multidentate ligands may include multiple pyridine and/or imidazole rings. Alternatively, metallocene derivatives, such as, for example, ferrocene, can be used. An example of one mediator is [Os(4-(N-(6-aminohexyl)aminobipyridine) (1,1'-dimethyl-2,2'-biimidazole)$_2$]Cl$_3$.

The redox mediators can be diffusible redox mediators or non-leachable redox mediators, such as non-leachable redox polymers. For additional information on redox mediators, see, for example, U.S. patent application Ser. No. 09/295,962, filed Apr. 21, 1999, now issued as U.S. Pat. No. 6,338,790, and its continuations U.S. Pat. Nos. 6,299,757 and 6,461,496, and PCT published application WO 98/35225, all which are incorporated herein by reference.

Second Electron Transfer Agent

In a preferred embodiment of the invention, the sensor includes a redox mediator and a second electron transfer agent which is capable of transferring electrons to or from the redox mediator and the analyte. The second electron transfer agent can be diffusible or can be non-leachable (e.g., entrapped in or coordinatively, covalently, or ionically bound to a redox polymer). One example of a suitable second electron transfer agent is an enzyme which catalyzes a reaction of the analyte. For example, a glucose oxidase or glucose dehydrogenase, such as pyrroloquinoline quinone glucose dehydrogenase (PQQ), is used when the analyte is glucose. A lactate oxidase fills this role when the analyte is lactate. Other enzymes can be used for other analytes.

Counter Electrode

Counter electrode 24, as illustrated in FIGS. 1 and 2, can be constructed in a manner similar to working electrode 22. Counter electrode 24 may also be a counter/reference electrode. Alternatively, a separate reference electrode may be provided in contact with the sample chamber. Suitable materials for the counter/reference or reference electrode include, for example, Ag/AgCl or Ag/AgBr printed on a non-conducting base material or silver chloride on a silver metal base. The same materials and methods may be used to make the counter electrode as are available for constructing the working electrode 22, although different materials and methods may also be used. Preferably, the counter or counter/reference electrode is printed on an insulating base material. A tab 25', on which contact pad 25 is disposed, can be provided for making convenient connection to the external electronics (not shown), such as a coulometer, potentiostat, or other measuring device.

Optionally, a non-conductive filler material, such as a non-conductive ink, can be formed adjacent a counter electrode, or between multiple counter electrodes to provide a planar surface along the path of travel of the sample fluid in the sample chamber. The non-conductive filler material preferably creates a smooth surface to facilitate filling of the sample chamber by capillary action and/or for reducing the likelihood that air bubbles will become entrapped near the counter electrodes. This non-conductive material can be colored or colorless and may be formed on the substrate by printing or other techniques. The non-conductive material may be deposited prior to or subsequent to the formation of the counter electrode. In one embodiment, a non-conductive ink is used to fill in the area between multiple 12.3 micrometer (0.5 mil) thick counter electrodes. In another embodiment, a non-conductive ink is used to fill the area between multiple 6.4 micrometer (0.25 mil) thick counter electrodes. Generally, no filler ink is needed for thickness less about 6.4 micrometers, and in some sensor designs, no filler ink is needed for 6.4 micrometer thick counter electrodes.

Electrode Configuration

In one embodiment of the invention, working electrode 22 and counter electrode 24 are disposed opposite to and facing each other to form a facing electrode pair as depicted in FIGS. 1 and 2. In this preferred configuration, the sample chamber 26 is typically disposed between the two electrodes. For this facing electrode configuration, it is preferred that the electrodes are separated by a distance of no more than about 0.2 mm (e.g., at least one portion of the working electrode is separated from one portion of the counter electrode by no more than 200 $\mu$m), preferably no more than 100 $\mu$m, and most preferably no more than 50 $\mu$m.

Figure 4:
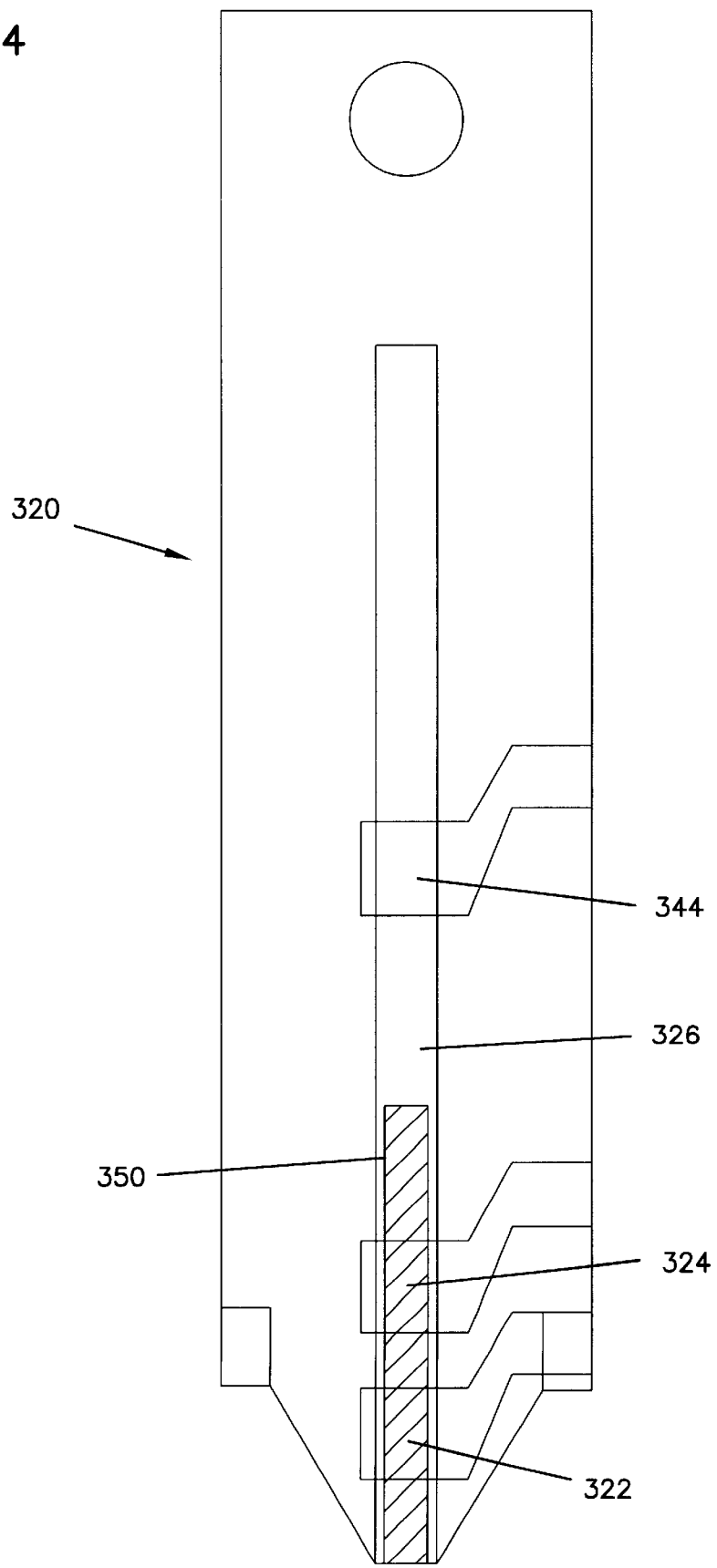
FIG. 4 is a top view of a third embodiment of an electrochemical sensor in accordance with the principles of the present invention, this sensor includes multiple working electrodes.

The electrodes need not be directly opposing each other; they may be slightly offset. Furthermore, the two electrodes need not be the same size. Preferably, the working electrode 22 extends the width of sensor 20 and counter electrode 24 is a portion or all of that width. Either of working electrode 22 or counter electrode 24 may include more than one electrode, such as shown in FIG. 4 (as counter electrodes 324, 344) and in FIG. 5B (as counter electrodes 424, 441, 442). Counter electrode 24 can also be formed with tines in a comb shape. Other configurations of both the counter electrode and working electrode are within the scope of the invention. However, for this particular embodiment, the separation distance between at least one portion of the working electrode and some portion of the counter electrode preferably does not exceed the limits specified hereinabove.

In another embodiment of the invention, the working and counter electrodes are coplanar. In this case, the sample chamber is in contact with both electrodes and is bounded on the side opposite the electrodes by a non-conducting inert base or substrate. Suitable materials for the inert base include non-conducting materials such as polyester.

Other configurations of the inventive sensors are also possible. For example, the two electrodes can be formed on surfaces that make an angle to each other. One such configuration would have the electrodes on surfaces that form a right angle. Another possible configuration has the electrodes on a curved surface such as the interior of a tube. For example, the working and counter electrodes can be arranged so that they face each other from opposite sides of the tube. This is another example of a facing electrode pair. Alternatively, the electrodes can be placed near each other on the tube wall (e.g., one on top of the other or side-by-side). In any configuration, the two electrodes must be configured so that they do not make direct electrical contact with each other, to prevent shorting of the electrochemical sensor.

Referring again to FIGS. 1 and 2, the electrodes 22, 24 extend from the sample chamber 26 to the other end of the sensor 20 as electrode extensions called "traces". Each trace provides a contact pad 23, 25 for providing electrical connection to a meter or other device to allow for data and measurement collection, as will be described later. Preferably, each contact pad 23, 25 is positioned on a tab 23', 25' that extends from each non-conducting base substrate 32, 34. In one embodiment, a tab has more than one contact pad positioned thereon. In a second embodiment, a single contact pad is used to provide a connection to one or more electrodes; that is, multiple electrodes are coupled together and are connected via one contact pad.

A spacer 33 can be used to keep the electrodes apart when the electrodes face each other as depicted in FIGS. 1 and 2; spacer 33 is clearly seen in FIG. 2. The spacer is typically constructed from an inert non-conducting material such as pressure-sensitive adhesive, polyester, Mylar™, Kevlar™ or any other strong, thin polymer film, or, alternatively, a thin polymer film such as a Teflon™ film, chosen for its chemical inertness. In addition to preventing contact between the electrodes, the spacer 33 can function as a portion of the boundary for the sample chamber 26. Other spacers include layers of adhesive and double-sided adhesive tape (e.g., a carrier film with adhesive on opposing sides of the film). Adhesive may be applied, for example by coating, onto a polymeric material to provide spacer 33.

Sample Chamber

The sample chamber 26 is typically defined by a combination of the electrodes 22, 24, the substrates 32, 34, and a spacer 33 as shown in FIGS. 1 and 2. A measurement zone is contained within this sample chamber and is the region of the sample chamber that contains only that portion of the sample that is interrogated during the analyte assay. In the embodiment of the invention illustrated in FIGS. 1 and 2, sample chamber 26 is the space between the two electrodes 22, 24 and their non-conductive base substrates 32, 34, bounded by spacer 33. In this embodiment, the sample chamber has a volume that is preferably no more than about 1 $\mu$L, more preferably no more than about 0.32 $\mu$L, and still more preferably no more than about 0.25 $\mu$L.

In the embodiment of the invention depicted in FIGS. 1 and 2, the measurement zone has a volume that is approximately equal to the volume of the sample chamber. In a preferred embodiment the measurement zone includes 80% of the sample chamber, 90% in a more preferred embodiment, and about 100% in a most preferred embodiment.

Figure 3:
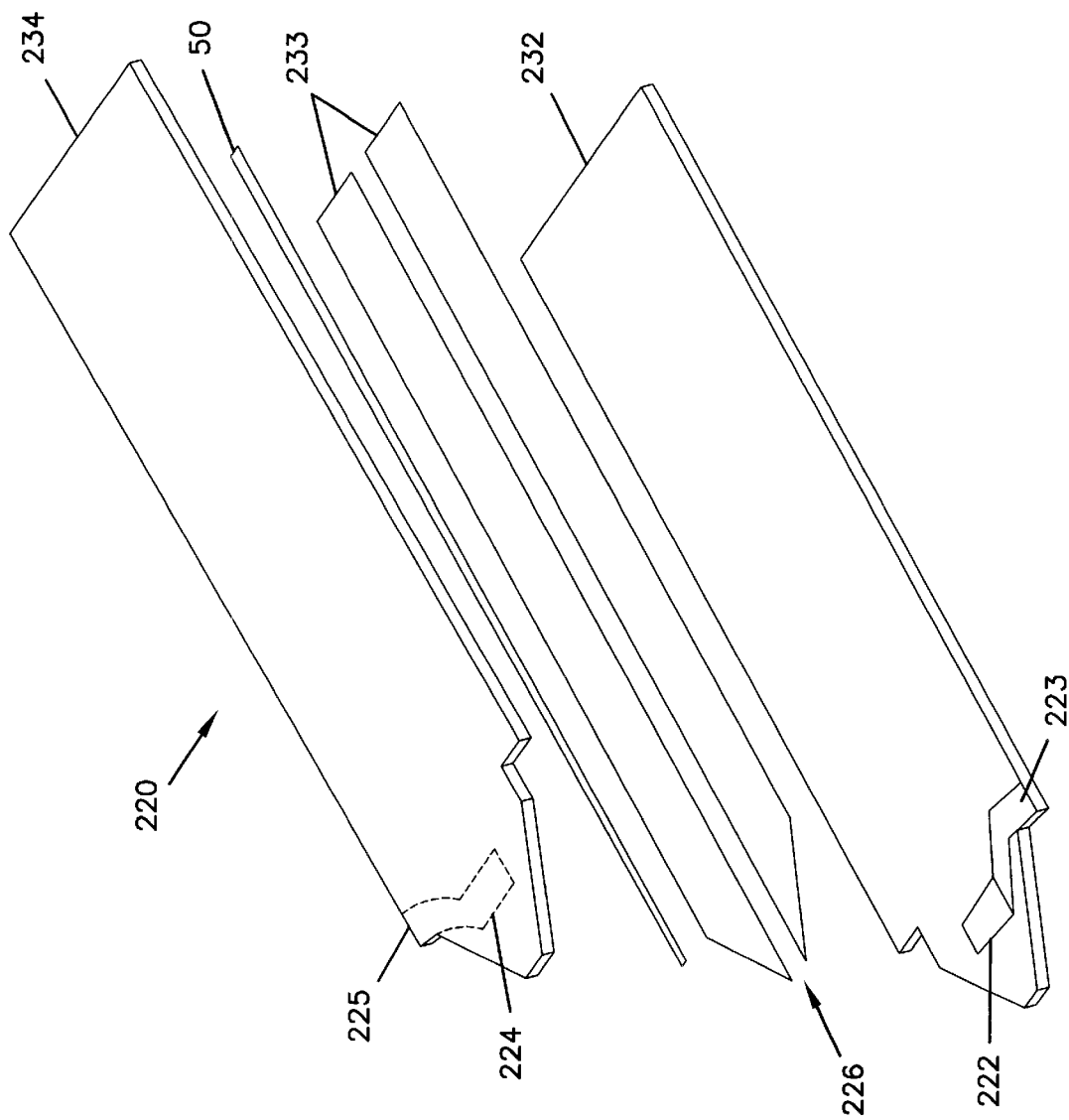
FIG. 3 is a schematic view of a second embodiment of an electrochemical sensor in accordance with the principles of the present invention having a working electrode and a counter electrode facing each other and having an extended sample chamber.

In another embodiment of the invention, shown in FIG. 3, sensor 220 has a working electrode 222 on non-conducting substrate base 232, a counter electrode 224 on non-conducting substrate base 234, and a spacer 233 therebetween. A contact pad 223 extends from working electrode 222, and likewise, a contact pad 225 extends from counter electrode 224. Sample chamber 226 (defined by base 232, 234 and spacer 233) extends the length of sensor 220 and includes much more space than the region proximate electrodes 222, 224. In this embodiment, the measurement zone, corresponding to the region containing the portion of the sample which will be interrogated, is the portion of sample chamber 226 bounded by the working surface of the working electrode 222 and counter electrode 224. In this embodiment, the measurement zone has a volume that is preferably no more than about 1 $\mu$L, more preferably no more than about 0.32 $\mu$L, still more preferably no more than about 0.25 $\mu$L, and most preferably no more than about 0.1 $\mu$L of sample.

In both of the embodiments discussed above, the thickness of the sample chamber and of the measurement zone correspond typically to the thickness of spacer 33, 233 (e.g., the distance between the electrodes in FIGS. 2 and 3, or the distance between the electrodes and the inert base in an embodiment where the electrodes are co-planar). The spacer can be, for example, an adhesive or double-sided adhesive tape or film. Examples of useable adhesives include urethanes, acrylates, acrylics, latexes, rubbers, and other known adhesive materials. Preferably, this thickness is small to promote rapid electrolysis of the analyte, as more of the sample will be in contact with the electrode surface for a given sample volume. In addition, a thin sample chamber helps to reduce errors from diffusion of analyte into the measurement zone from other portions of the sample chamber during the analyte assay, because diffusion time is long relative to the measurement time. Typically, the thickness of the sample chamber is between about 50 and about 200 micrometers.

Sorbent Material

The sample chamber can be empty before the sample is placed in the chamber, or, in some embodiments, the sample chamber can include a sorbent material (shown in FIG. 3 as sorbent 50) to sorb and hold a fluid sample during the measurement process. Suitable sorbent materials include polyester, nylon, cellulose, and cellulose derivatives such as nitrocellulose. The sorbent material facilitates the uptake of small volume samples by a wicking action which can complement or, preferably, replace any capillary action of the sample chamber. In addition to or alternatively, a portion or the entirety of the wall of the sample chamber may be coated by a surfactant, which is intended to lower the surface tension of the fluid sample and improve fluid flow within the sample chamber. An example of a useable surfactant is available under the tradename "Zonyl FSO" from Dupont of Wilmington, Del.

Methods other than the wicking action of a sorbent can be used to transport the sample into the sample chamber or measurement zone. Examples of such methods for transport include the application of pressure on a sample to push it into the sample chamber, the creation of a vacuum by a pump or other vacuum-producing method in the sample chamber to pull the sample into the chamber, capillary action due to interfacial tension of the sample with the walls of a thin sample chamber, as well as the wicking action of a sorbent material.

The entire sensor assembly is held firmly together to ensure that the sample remains in contact with the electrodes and that the sample chamber and measurement zone maintain the same volume. This is an important consideration in the coulometric analysis of a sample, where measurement of a defined sample volume is needed.

Alternative Sensor Designs

FIGS. 4 through 12 illustrate alternative sensor designs, both tip-filling and side-filling. Referring to FIG. 4, a sensor 320 has a working electrode 322, a counter electrode 324, a second counter electrode 344 (which may provide a fill indicator function, as described below), and a sample chamber 326 extending along at least a portion of the length of sensor 320 and optionally including a sorbent 350.

Figure 5A:
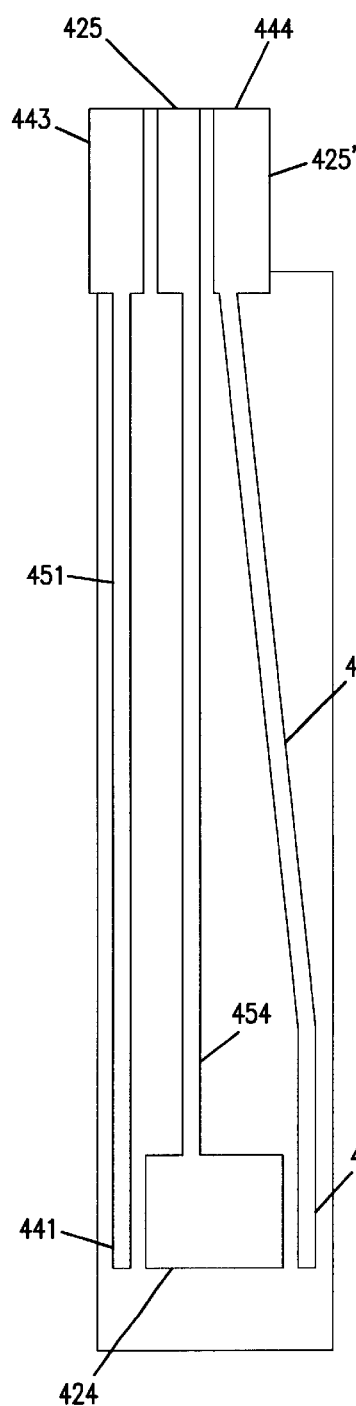
FIG. 5A illustrates a top view of a first substrate with a working electrode for use in a fourth embodiment of a sensor according to the invention.
Figure 5B:
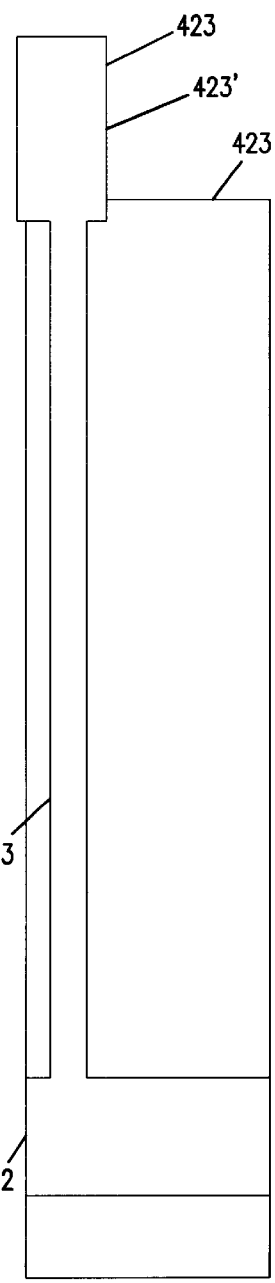
FIG. 5B illustrates a bottom view of a second substrate (inverted with respect to FIG. 5A) with counter electrodes placement over and opposite the substrate of FIG. 5A.
Figure 5C:
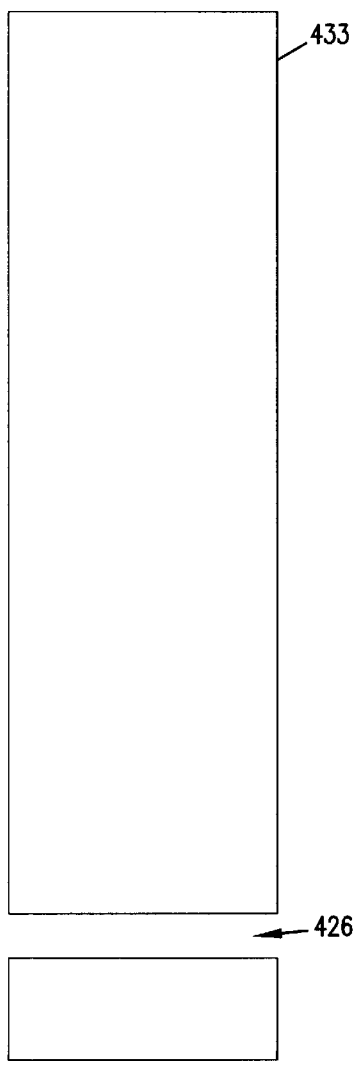
FIG. 5C illustrates a top view of a spacer for placement between the first substrate of FIG. 5A and the second substrate of FIG. 5B.

FIGS. 5A through 5C illustrate three layers that when assembled, provide a preferred embodiment of a sensor. FIG. 5A has a working electrode 422 on substrate 432. Working electrode 422 has a trace 453 extending from sample chamber 426 to tab 423' on which is contact pad 423; contact pad 423 connects the sensor to a meter or other measurement equipment. FIG. 5B, (inverted with respect to FIG. 5A to show the electrode side up), has a counter electrode 424 on substrate 434, and also includes a first indicator electrode 441 and a second indicator electrode 442. Counter electrode 424 has a trace 454, first indicator electrode 441 has trace 451, and second indicator electrode 442 has trace 452, that end at contact pads 425, 443, 444, respectively, on tab 425'. Spacer 433 in FIG. 5C defines sample chamber 426 and provides spacing between the electrodes when the two substrates 432, 434 are positioned opposite and facing one another.

Figure 6A:
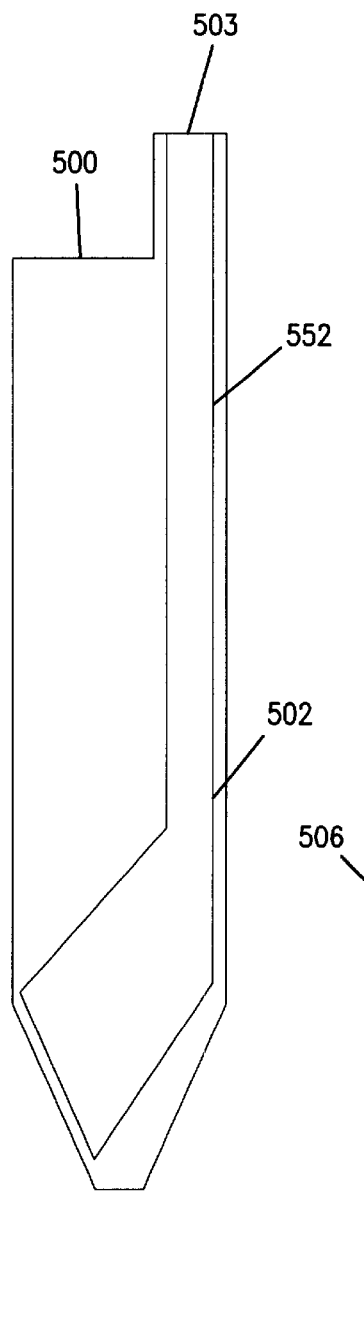
FIG. 6A illustrates a top view of a first film with a working electrode for use in a fifth embodiment of a sensor according to the invention.
Figure 6B:
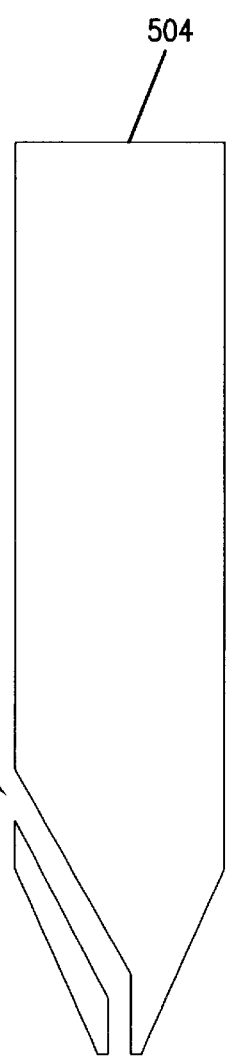
FIG. 6B illustrates a top view of a spacer for placement on the first film of FIG. 6A.
Figure 6C:
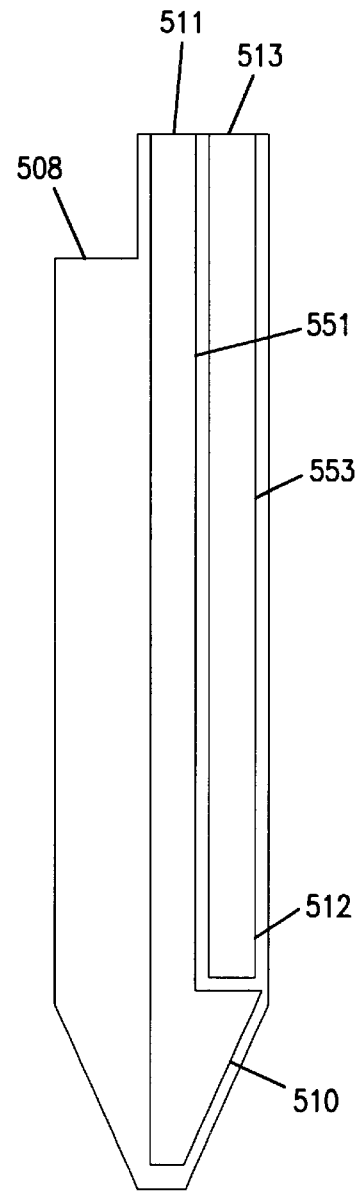
FIG. 6C illustrates a bottom view of a second film (inverted with respect to FIGS. 6A and 6B) with counter electrodes placement over the spacer of FIG. 6B and first film of FIG. 6A.

FIGS. 6A through 6C also illustrate three layers that, when assembled, provide a sensor. In FIG. 6A, a working electrode 502 is formed on first substrate 500. The working electrode 502 includes a contact pad 503 for connection with external electronics; this contact pad 503 is connected to working electrode 502 by trace 552. A spacer 504, shown in FIG. 6B, such as a layer of adhesive or a double-sided tape defines a channel 506 to produce a sample chamber for the sensor. Two counter (or counter/reference) electrodes 510, 512 are formed on a second substrate 508, as shown in FIG. 6C (inverted with respect to FIG. 6A to show the electrode side up). This multiple counter electrode arrangement can provide a fill indicator function, using counter electrode 512, as described below. Each counter electrode 510, 512 has a contact region or pad 511, 513 for connection with external electronics; these contact pads 511, 513 are connected to counter electrodes 510, 512 by traces 551, 553. The second substrate 508 is inverted and placed over the first substrate 500, with the spacer 504 between, so that the working electrode 502 and the two counter electrodes 510, 512 are facing in the region of the channel 506.

In some instances, the counter electrode 510 nearest an entrance 514 (FIG. 6B) of the channel 506 has a surface area within the sample chamber that is at least two times larger than the other counter electrode 512, and may be at least five or ten times larger. The non-leachable or diffusible redox mediator and/or second electron transfer agent can be provided on either the first or second substrates 500, 508 in a region corresponding to the channel 506, as described above.

The working electrode and counter electrodes can be formed to cover the entire channel region (except for a small space between the two counter electrodes). In this embodiment, the sample chamber and measurement zone are effectively the same and have the same volume. In other embodiments, the measurement zone has, for example, 80% or 90% of the volume of the sample chamber. It will be understood that similar sensors could be made using one counter electrode or three or more counter electrodes. It will also be understood that multiple working electrodes may also be provided on the sensor.

FIGS. 7A, 7B and 7C illustrate a side-filling sensor arrangement. FIG. 7A shows a first substrate 520 with a working electrode 522. FIG. 7B illustrates a spacer 524 defining a channel 526. FIG. 7C (inverted with respect to FIGS. 7A and 7B) illustrate a second substrate 528 with three counter (or counter/reference) electrodes 530, 532, 534. This multiple counter electrode arrangement can provide a fill indicator function, as described below. An indentation 536, 538 or recessed or indented portion can be formed at either edge of the opening to channel 526 to facilitate the drawing of fluid into the sensor. This configuration can aid in wicking or capillary filling of the channel (i.e., sample chamber). This configuration can also reduce the likelihood that the user will inadvertently block the channel during collection of the sample, which could occur by pressing the tip of the sensor edgewise against the skin.

FIGS. 8A, 8B, and 8C illustrate another example of a side-filling sensor arrangement. FIG. 8A illustrates a first substrate 540 with a working electrode 542. FIG. 8B illustrates a spacer 544 defining a channel 546. FIG. 8C (inverted with respect to FIGS. 8A and 8B) illustrates a second substrate 548 with three counter (or counter/reference) electrodes 550, 552, 554.

Figure 9A:
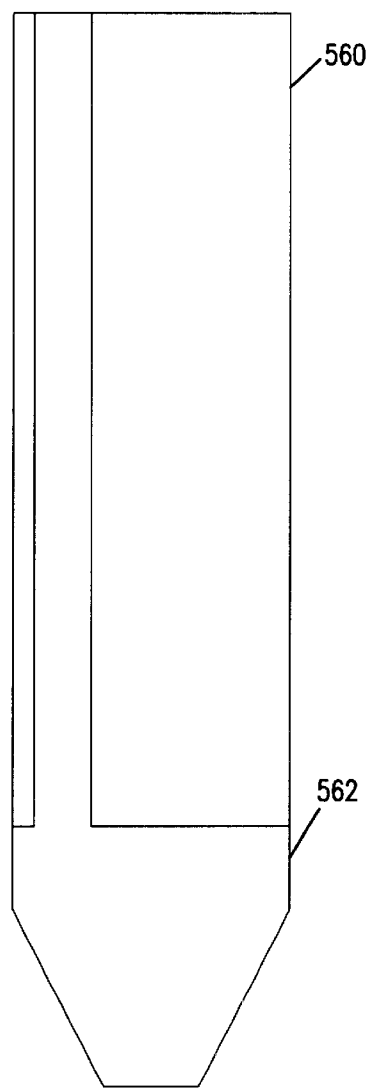
FIG. 9A illustrates a top view of a first film with a working electrode for use in a eighth embodiment of a sensor according to the invention.
Figure 9B:
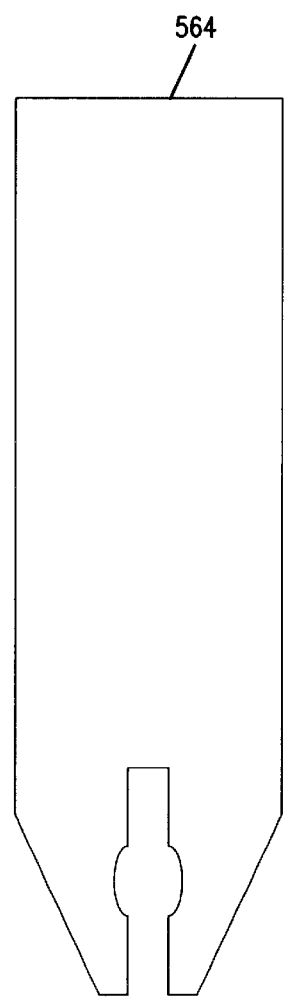
FIG. 9B illustrates a top view of a spacer for placement on the first film of FIG. 9A.
Figure 9C:
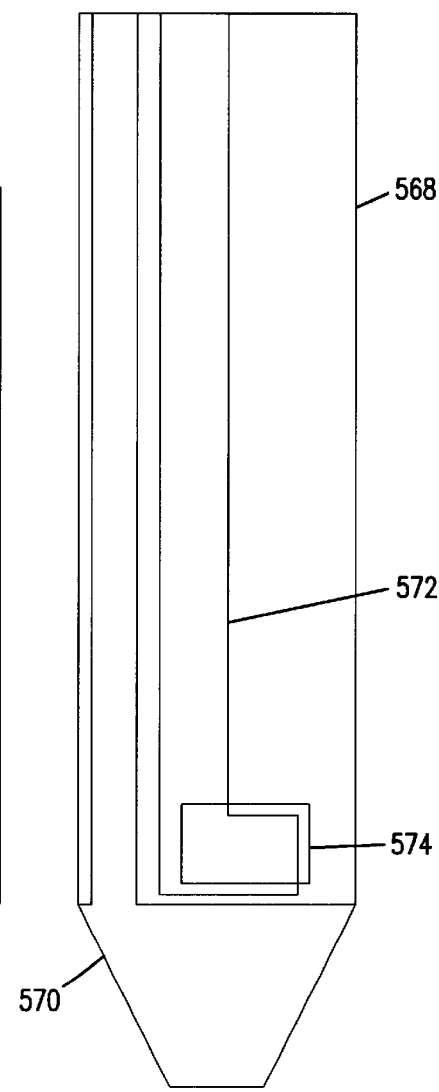
FIG. 9C illustrates a bottom view of a second film (inverted with respect to FIGS. 9A and 9B) with counter electrodes placement over the spacer of FIG. 9B and first film of FIG. 9A.

FIGS. 9A, 9B, and 9C illustrate another example of a tip-filling sensor arrangement. FIG. 9A illustrates a first substrate 560 with a working electrode 562. FIG. 9B illustrates a spacer 564 defining a channel 566. FIG. 9C (inverted with respect to FIGS. 9A and 9B) illustrates a second thin film substrate 568 with two counter (or counter/reference) electrodes 570, 572. This multiple counter electrode arrangement can provide a fill indicator function, as described below. A vent hole 574 (indicated as a shaded region in FIG. 9C) is provided through the second substrate. In the illustrated embodiment, this vent hole 574 is made through only the substrate 568 that carries the counter electrode(s) and, optionally, the spacer 564. In this embodiment, the vent hole can be formed by, for example, die cutting a portion of the substrate. This die cut can remove a portion of at least one counter electrode, but a sufficient amount of the counter electrode should remain for contact with the sample in the channel and for electrical connection to a contact at the other end of the sensor. In another embodiment, the vent hole 574 can be made through all of the layers or through the first substrate and not the second substrate.

Another embodiment is illustrated in FIGS. 10A, 10B, and 10C, with a different shape. This sensor includes a first substrate 579 with at least one working electrode 580, as illustrated in FIG. 10A. The sensor also includes a spacer 581 with a channel 582 formed in the spacer 581, as shown in FIG. 10B. The sensor further includes a second substrate 583 with two counter electrodes 584, 585, as shown in FIG. 10C (inverted with respect to FIGS. 10A and 10B). A venting aperture 586 is cut typically through all of the layers and extends from a side of the sensor. In some embodiments, the venting aperture and the front portion 587 of the sensor are simultaneously cut with a reproducible distance between the venting aperture and the front portion 587 of the sensor to provide a reproducible length for the channel 582 and the working electrode 580. This tip-filling sensor arrangement optionally includes an indentation 588 or recessed or indented portion that can be formed at the filling opening of the channel 582 to facilitate the drawing of fluid into the sensor.

Figure 11C:
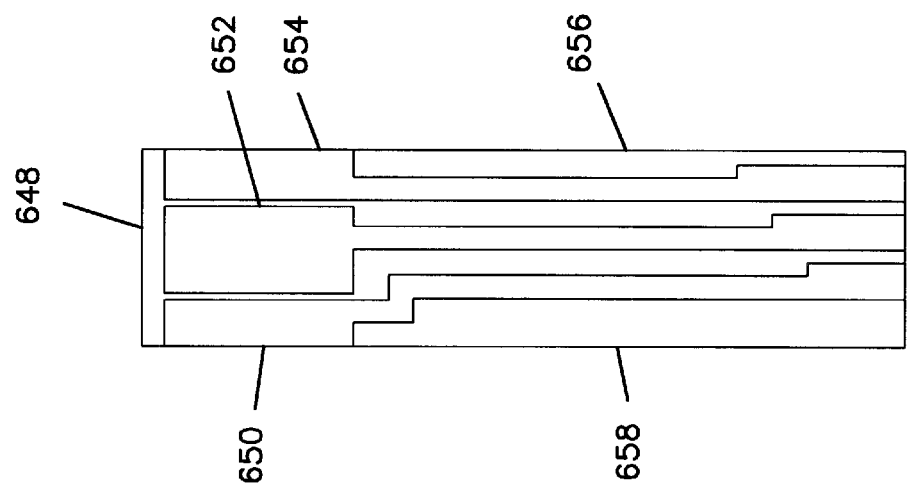
FIG. 11C illustrates a bottom view of a second film (inverted with respect to FIGS. 11A and 11B) with counter electrodes placement over the spacer of FIG. 11B and first film of FIG. 11A.
Figure 11B:
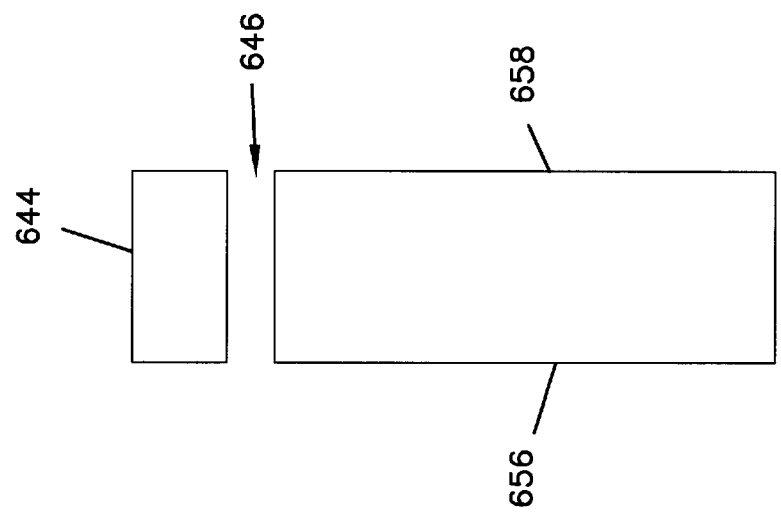
FIG. 11B illustrates a top view of a spacer for placement on the first film of FIG. 11A.
Figure 11A:
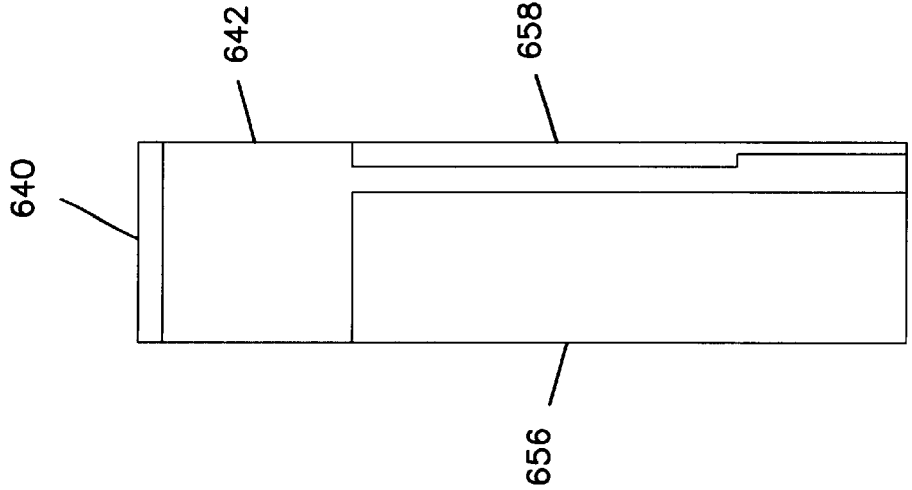
FIG. 11A illustrates a top view of a first film with a working electrode for use in a tenth embodiment of a sensor according to the invention.

FIGS. 11A, 11B, and 11C illustrate another example of a side-filling sensor arrangement. FIG. 11A illustrates a first substrate 640 with a working electrode 642. FIG. 11B illustrates a spacer 644 defining a channel 646. FIG. 11C (inverted with respect to FIGS. 11A and 11B) illustrates a second substrate 648 with three counter (or counter/reference) electrodes 650, 652, 654. This multiple counter electrode arrangement can provide a fill indicator function, as described below. The length of the channel 646 is typically defined by the two parallel cuts along the sides 656, 658 of the sensors.

Figure 13A:
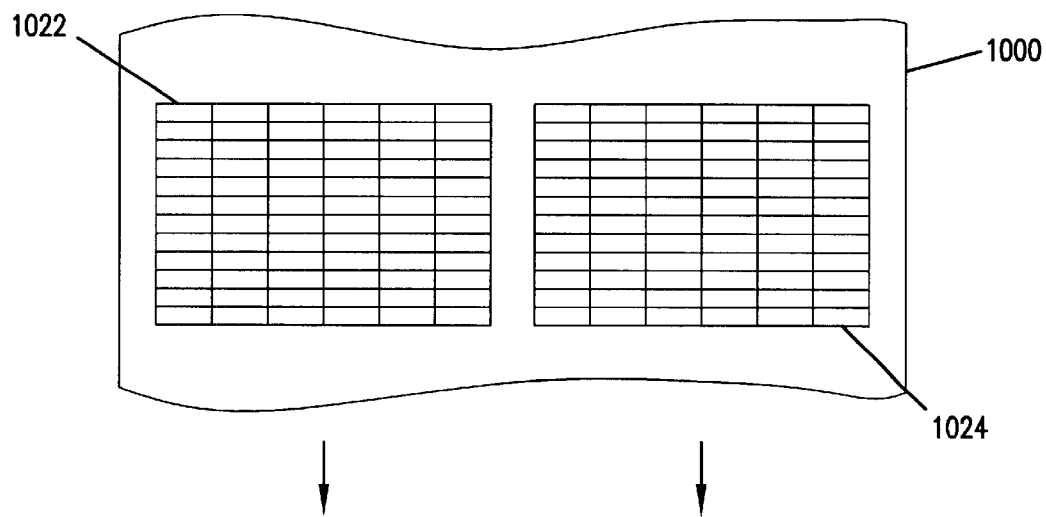
FIG. 13A illustrates a top view of one embodiment of a sheet of sensor components, according to the invention.

Because of the straight sides, these sensors (and also those shown in FIGS. 1, 2 and 5) can be manufactured adjacent to one another, as illustrated in FIG. 13A. Such positioning during manufacture produces less waste material. Another optional processing advantage of the adjacent sensor manufacturing process is that the redox mediator and/or second electron transfer agent can be readily disposed in the channel by striping a continuous stream of these components along a row or column of adjacent sensors. This can result in better efficiency and less waste of expensive reagents such as the redox mediator and/or second electron transfer agent, as compared to other techniques, such as individually placing these components within the individual channels.

FIGS. 12A, 12B, and 12C illustrate another sensor configuration. This sensor includes a first substrate 600 with at least one working electrode 602, as illustrated in FIG. 12A. The sensor also includes a spacer 604 with a channel 606 formed in the spacer 604, as shown in FIG. 12B. The sensor further includes a second substrate 608 with two counter electrodes 610, 612, as shown in FIG. 12C (inverted with respect to FIGS. 12A and 12B). This multiple counter electrode arrangement may provide a fill indicator function, as described below. The sensor can also include, for example, an indicator, such as a slot 614 or an extension 616 from the body of the sensor that indicates to the user which side of the sensor should be placed adjacent to the sample. Surface printing can also or alternatively be applied to the sensor to act as an indicator. Some indication mechanism can be particularly important where the sensor reading is only correct when the sample enters from a particular side.

Multiple Electrode Sensors and Calibration Thereof

Multiple electrode sensors can be used for a variety of reasons. For example, multiple electrodes can be used to test a variety of analytes using a single sample. One embodiment with multiple electrodes has one or more sample chambers, each of which contains one or more working electrodes, with each working electrode defining a different measurement zone. If the redox mediator is non-leachable, one or more of the working electrodes can have the appropriate chemical reagents, for example, an appropriate enzyme, to test a first analyte and one or more of the remaining working electrodes can have the appropriate chemical reagents to test a second analyte, and so on. For example, a multiple electrode sensor might include a working electrode having glucose oxidase disposed thereon to determine glucose concentration and another working electrode can have lactate oxidase disposed thereon to determine lactate concentration.

Multiple electrodes could also be used to improve the precision of the resulting readings. The measurements from each of the working electrodes (all of which are detecting the same analyte) can be averaged or otherwise combined together to obtain a more precise or reliable reading. In some cases, measurements could be rejected if the difference between the value and the average exceeds a threshold limit. This threshold limit could be, for example, determined based on a statistical parameter, such as the standard deviation of the averaged measurements. The average could then be recalculated while omitting the rejected values. In addition to using multiple electrode sensors to increase precision, multiple measurements could be made at each electrode and averaged together to increase precision. This technique could also be used with a single electrode sensor to increase precision.

One example of a multiple electrode sensor that can be used to accurately determine the volume of the measurement zones of the electrode pairs and that is also useful in reducing noise is presented herein. In this example, one of the working electrodes is prepared with a non-leachable redox mediator and a non-leachable second electron transfer agent (e.g., an enzyme). Another working electrode includes nonleachable redox mediator, but no second electron transfer agent on the electrode. An optional third working electrode has no redox mediator and no second electron transfer agent bound to the electrode. A similar configuration can be constructed using diffusible redox mediator and/or diffusible second electron transfer agent although diffusible components are not limited to being disposed on the working electrode. Preferably, the distance between the working electrodes is sufficient that redox mediator and/or enzyme do not substantially diffuse between electrodes within the measurement period (e.g., in the time period from introduction of the same sample into the sample chamber to the end of the measurement).

The sensor error caused by the redox mediator being in a non-uniform oxidation state prior to the introduction of the sample can be measured by concurrently electrolyzing the sample in the measurement zones that are proximate working and counter electrodes. At the first working electrode, the analyte is electrolyzed to provide the sample signal. At the second working electrode, the analyte is not electrolyzed because of the absence of the second electron transfer agent (assuming that a second electron transfer agent is necessary). However, a charge will pass (and a current will flow) due to the electrolysis of the redox mediator that was in a mixed oxidation state (i.e., some redox centers in the reduced state and some in the oxidized state) prior to the introduction of the sample and/or the shuttling of a diffusible redox mediator between the working electrode and the counter electrode. The small charge passed using this second working electrode can be subtracted from the charge passed using the first electrode pair to substantially remove the error due to the oxidation state of the redox mediator and/or to remove the background current caused by a diffusible redox mediator. This procedure also reduces the error associated with other electrolyzed interferents, such as ascorbate, urate, and acetaminophen, as well as errors associated with capacitive charging and faradaic currents.

The thickness of the sample chamber can be determined by measuring the capacitance, preferably in the absence of any fluid, between an electrode and its corresponding counter electrode. The capacitance of an electrode pair depends on the surface area of the electrodes, the interelectrode spacing, and the dielectric constant of the material between the plates. The dielectric constant of air is unity which typically means that the capacitance of this electrode configuration is a few picofarads (or about 100–1000 picofarads if there is fluid between the electrode and counter electrode given that the dielectric constant for most biological fluids is approximately 75). Thus, since the surface area of the electrodes are known, measurement of the capacitance of the electrode pair allows for the determination of the thickness of the measurement zone to within about 1–5%.

Other electrode configurations can also use these techniques (i.e., capacitance measurements and coulometric measurements in the absence of a critical component) to reduce background noise and error due to interferents and imprecise knowledge of the volume of the interrogated sample. Protocols involving one or more working electrode(s) and counter electrode(s) and one or more of the measurements described above can be developed and are within the scope of the invention. For example, only one electrode pair is needed for the capacitance measurements, however, additional electrodes can be used for convenience.

Fill Indicator

When using a sample chamber that is filled with 1 μL or less of fluid, it is often desirable to be able to determine when the sample chamber is filled. FIGS. 6A through 6C illustrate a sensor having a fill indicator structure. In particular, FIG. 6A illustrates a first substrate 500 upon which a working electrode 502 is printed. A spacer 504 (FIG. 6B), such as, for example, a layer of adhesive or a double-sided tape, is formed over the first substrate 500 and working electrode 502 with a channel 506 formed in the layer to provide a sample chamber. A second substrate 508 is printed with two counter electrodes 510, 512, as shown in FIG. 6C (inverted with respect to FIGS. 6A and 6B to show the electrode side up). Preferably, the counter electrode 510 nearest an entrance 514 of the channel 506 has a surface area within the sample chamber that is at least two times larger than the other counter electrode 512, and preferably at least five or ten times larger.

The sensor can be indicated as filled, or substantially filled, by observing a signal between the second counter electrode 512 and the working electrode 502 as the sensor fills with fluid. When fluid reaches the second counter electrode 512, the signal from that counter electrode will change. Suitable signals for observing include, for example, voltage, current, resistance, impedance, or capacitance between the second counter electrode 512 and the working electrode 502. Alternatively, the sensor can be observed after filling to determine if a value of the signal (e.g., voltage, current, resistance, impedance, or capacitance) has been reached indicating that the sample chamber is filled.

In alternative embodiments, the counter electrode or working electrode can be divided into two or more parts and the signals from the respective parts observed to determine whether the sensor has been filled. In one example, the working electrode is in a facing relationship with the counter electrode and the indicator electrode. In another example, the counter electrode, working electrode, and indicator electrode are not in a facing relationship, but are, for example, side-by-side. Typically, the indicator electrode is further downstream from a sample inlet port than the working electrode and counter electrode.

For side-fill sensors, such as those illustrated in FIGS. 5, 7, 8 and 11, an indicator electrode can be disposed on each side of the primary counter electrode. This permits the user to fill the sample chamber from either the left or right side with an indicator electrode disposed further upstream. This three-electrode configuration is not necessary. Side-fill sensors can also have a single indicator electrode and, preferably, some indication as to which side should be placed in contact with the sample fluid.

Alternately or additionally, two indicator electrodes, used in combination with one counter/reference electrode, detect when the sample chamber begins to fill and when the sample chamber has been filled to prevent partial filling of the sample chamber. The two indicator electrodes are optionally held at a different potential than the counter/reference electrode. The start and completion of filling of the sample chamber is indicated by the flow of current between the indicator and counter/reference electrodes.

In other instances, the potential of each of the counter/reference electrodes may be the same. When the potential at all three counter/reference electrodes is the same, for example, 0 volts, then as the measurement zone begins to fill, the fluid allows for electrical current flow between a working electrode and the first counter/reference electrode, causing a current at the first counter/reference electrode due to the reaction of the analyte with the enzyme and the mediator. When the fluid reaches the third counter/reference electrode, another current may be measured similar to the first counter/reference electrode indicating that the measurement zone is full. When the measurement zone is full, the three counter/reference electrodes are optionally shorted together or their signals can be added or otherwise combined.

The indicator electrode can also be used to improve the precision of the analyte measurements. The indicator electrode may operate as a working electrode or as a counter electrode or counter/reference electrode. In the embodiment of FIGS. 6A through 6C, the indicator electrode 512 can act as a second counter or counter/reference electrode with respect to the working electrode 502. Measurements from the indicator electrode/working electrode can be combined (for example, added or averaged) with those from the first counter/reference electrode/working electrode to obtain more accurate measurements. In one embodiment, the indicator electrode operates as a second working electrode with the counter electrode or counter/reference electrode. In another embodiment, the indicator electrode operates as a second working electrode with a second counter electrode or counter/reference electrode. In still another embodiment, the indicator electrode operates as a second counter electrode or counter/reference electrode with a second working electrode.

The sensor or a sensor reader can include a sign (e.g., a visual sign or auditory signal) that is activated in response to the indicator electrode to alert the user that the measurement zone has been filled. The sensor or a sensor reader can be configured to initiate a reading when the indicator electrode indicates that the measurement zone has been filled with or without alerting the user. The reading can be initiated, for example, by applying a potential between the working electrode and the counter electrode and beginning to monitor the signals generated at the working electrode.

General Method for Manufacturing Sensors

Figure 13B:
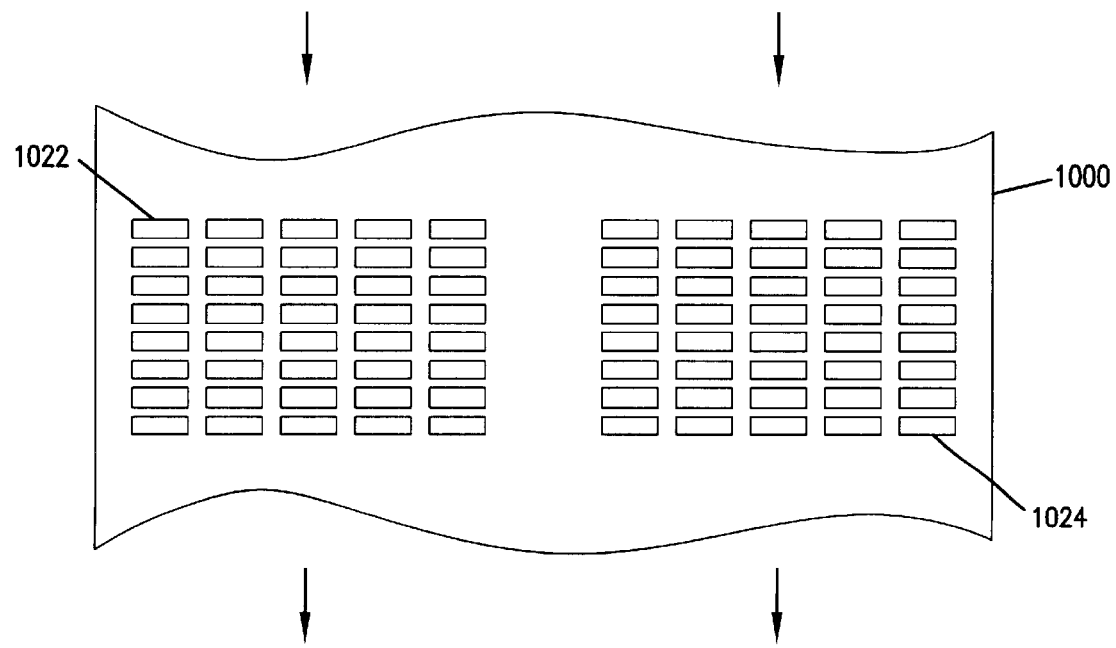
FIG. 13B illustrates a top view of another embodiment of a sheet of sensor components, according to the invention.

Referring now to FIGS. 13A and 13B, one example of a method for making thin film sensors is described with respect to the sensor arrangement displayed in FIGS. 5A through 5C, although this method can be used to make a variety of other sensor arrangements, including those described before. When the three layers of FIGS. 5A through 5C are assembled, a sensor 420 is formed.

In FIGS. 13A and 13B, a substrate 1000, such as a plastic substrate, is moving in the direction indicated by the arrow. The substrate 1000 can be an individual sheet or a continuous roll on a web. Multiple sensors 420 can be formed on a substrate 1000 as sections 1022 that have working electrodes 422 (FIG. 5A) thereon and sections 1024 that have counter electrode 424 and indicator electrodes 441, 442 (FIG. 5B). These working, counter and indicator electrodes are electrically connected to their corresponding traces and contact pads. Typically, working electrode sections 1022 are produced on one half of substrate 1000 and counter electrode sections 1024 are produce on the other half of substrate 1000. In some embodiments, the substrate 1000 can be scored and folded to bring the sections 1022, 1024 together to form the sensor. In some embodiments, as illustrated in FIG. 13A, the individual working electrode sections 1022 can be formed next to or adjacent each other on the substrate 1000, to reduce waste material. Similarly, individual counter electrode sections 1024 can be formed next to or adjacent each other. In other embodiments, the individual working electrode sections 1022 (and, similarly, the counter electrode sections 1024) can be spaced apart, as illustrated in FIG. 13B. The remainder of the process is described for the manufacture of multiple sensors, but can be readily modified to form individual sensors.

Carbon or other electrode material (e.g., metal, such as gold or platinum) is formed on the substrate 1000 to provide a working electrode 422 for each sensor. The carbon or other electrode material can be deposited by a variety of methods including printing a carbon or metal ink, vapor deposition, and other methods. The printing may be done by screen printing, gravure roll printing, transfer printing, and other known printing methods. Trace 453 and contact pad 423 are preferably applied together with working electrode 422, but may be applied in a subsequent step.

Similar to the working electrode 422, the counter electrode(s) 424, 441, 442 (shown in FIG. 5B) are formed on the substrate 1000. The counter electrodes are formed by providing carbon or other conductive electrode material onto the substrate. In one embodiment, the material used for the counter electrode(s) is a Ag/AgCl ink. The material of the counter electrode(s) may be deposited by a variety of methods including printing or vapor deposition. The printing may be done by screen printing, gravure roll printing, transfer printing, and other known printing methods. Traces 454, 451, 452 and contact pads 425, 443, 444 are preferably applied together with counter electrodes 424, 441, 442, but may be applied in a subsequent step.

Preferably, multiple sensors 420 are manufactured simultaneously; that is, the working electrodes, including their traces and contact pads, for a plurality of sensors are produced (e.g., printed) on a polymer sheet or web, and simultaneously or to subsequently, the counter electrodes, and their traces and contact pads, for a plurality of sensors are produced (e.g., printed). The working electrode(s) and counter electrode(s) can be formed on separate substrates that are later positioned opposite one another so that the electrodes face each other. Alternately, to simplify registration of the substrates, the working electrodes can be formed on a first half of a substrate sheet of web and the counter electrodes are formed on a second half of the substrate sheet or web so that the sheet or web can be folded to superimpose the working and counter electrodes in a facing arrangement.

To provide a sample chamber 426, a spacer 433 is formed over at least one of the substrate/working electrode and substrate/counter electrode(s). The spacer 433 is preferably an adhesive spacer, such as a single layer of adhesive or a double-sided adhesive tape (e.g., a polymer carrier film with adhesive disposed on opposing surfaces). Suitable spacer materials include adhesives such as urethanes, acrylates, acrylics, latexes, rubbers and the like.

A channel, which will result in the sample chamber, is provided in the spacer 433, either by cutting out a portion of the adhesive spacer or placing two adhesive pieces in close proximity but having a gap therebetween. The adhesive can be printed or otherwise disposed on the substrate according to a pattern which defines the channel region. The adhesive spacer can be optionally provided with one or more release liners prior to its incorporation into the sensor. The adhesive can be cut (e.g., die-cut or slit) to remove the portion of the adhesive corresponding to the channel prior to disposing the spacer on the substrate.

In one method of the invention, illustrated in FIGS. 14A through 14G, the adhesive includes a first and a second release liner. Prior to applying the adhesive to a first substrate/working electrode or substrate/counter electrode (s), the adhesive is "kiss-cut" through the first release liner and at least a portion of the underlying adhesive, preferably the entire adhesive but not through the second release liner, to form one or more sections, one of which will eventually result in a sample chamber. The first release liner is removed from the adhesive over its length but is retained over the sample chamber section. The exposed adhesive is then applied to the first substrate/working electrode or substrate/counter electrode(s). On removal of the second release liner, the adhesive positioned within the sample chamber sections is also removed, leaving a channel or opening in the adhesive spacer. The second substrate/working electrode or substrate/counter electrode(s) is then applied to the adhesive to form the layered sensor structure.

Figure 14G:
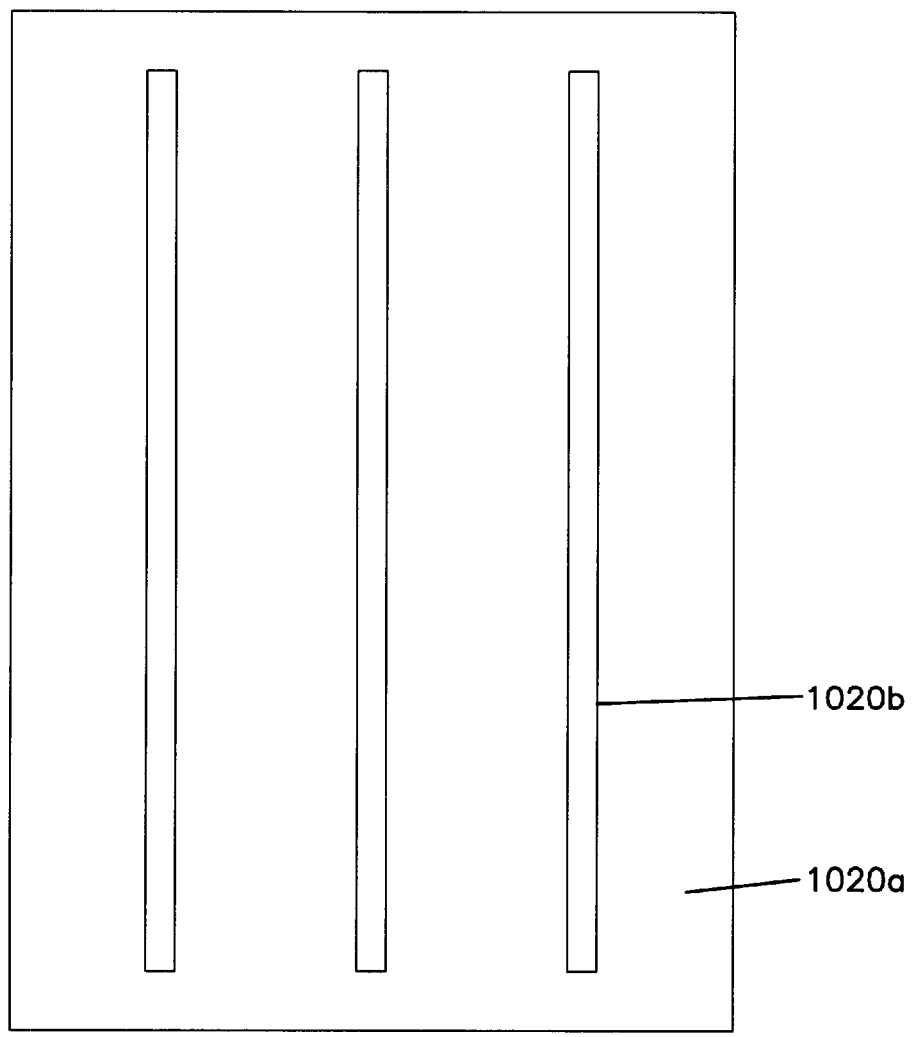
FIG. 14G is a bottom view of FIG. 14B.

FIGS. 14A through 14G describe in detail the processing of an adhesive layer by a "kiss-cut". An adhesive layer that will eventually become spacer 433 is preferably obtained from an adhesive structure including an adhesive layer 1030 between a first release liner 1020 and a second release liner 1040. A blade (e.g., a knife or die blade) cuts through the first release liner 1020 and at least a portion of the adhesive layer 1030, but not through the second release liner 1040, as shown in FIGS. 14B and 14G, to form release liner sections 1020a, 1020b, and adhesive sections 1030a, 1030b. The space occupied by 1030b is the area that will result in the sample chamber of the sensor and can be referred to as "sample chamber region". A cut configuration such as shown in FIG. 14G allows removal of one release liner section 1030a, leaving behind release liner section 1030b. The liner could be cut to provide individual strips extending the entire length of the liner; this would then need removal of each individual liner strip.

The release liner section 1030a is removed to provide the adhesive configuration shown in FIG. 14C. The exposed adhesive is positioned over and securely adhered to the substrate 1050, as illustrated in FIG. 14D. The adhesive sections 1030a without the release liner will adhere to the substrate 1050. As shown in FIG. 14E, the second release liner 1040 is removed, pulling the cut and non-adhered section of adhesive 1030b and the first liner 1020b with it; this results in adhesive areas 1030a providing spacer layer sections 433a, 433b, with sample chamber 426 therebetween, as illustrated in FIG. 14F. The second substrate is then positioned over the adhesive layer and laminated to the first substrate via the spacer 433. The thickness of the spacer 433 typically determines the spacing between the working and counter electrodes, and thus impacts the volume of the sample chamber 426. Preferably, the thickness does not vary more than ±5% over the individual sensor and/or among individual sensors in a batch. Use of the "kiss-cut" method for manufacturing the layered sensor structure preserves the integrity of the sample chamber walls during manufacturing, thereby providing for more reliable and reproducible sample chamber volumes.

The non-leachable or diffusible redox mediator and/or second electron transfer agent are disposed onto the substrate in at least the sample chamber regions. If either or both of these components is non-leachable, that component or components is preferably disposed on the working electrode. If either or both of these components is diffusible, that component or components can be disposed on any surface of the substrate in the channel region. The redox mediator and/or second electrode transfer agent can be disposed independently or together on the substrate prior to or after disposition of the spacer. The redox mediator and/or second electrode transfer agent may be disposed by a variety of methods including, for example, screen printing, ink jet printing, spraying, painting, striping along a row or column of aligned and/or adjacent electrodes, and the like. Other components can be deposited separately or together with the redox mediator and/or second electrode transfer agent; these components can include, for example, surfactants, polymers, polymer films, preservatives, binders, buffers, and cross-linkers.

After disposing the spacer, redox mediator, second electron transfer agent, sensing layers, and the like, the first and second substrates (having the working and counter electrodes thereon) are positioned opposite each other to form the sensor. The faces of the substrate are joined by the adhesive of the spacer. Preferably, after bringing the faces together, individual sensors are cut out from the web of sensors using a variety of methods including, for example, die cutting, slitting, or otherwise cutting away the excess substrate material and separating the individual sensors. In some embodiments, a combination of cutting or slitting methods is used. As another alternative, the individual sensor components can first be cut out of the substrates and then brought together to form the sensor by adhesively joining the two components, such as by using the spacer adhesive.

The sides of the sensor can be straight to allow the sensor to be cut out from the remainder of the substrate and/or from other sensors by slitting the substrate in parallel directions using, for example, a gang arbor blade system. The edges of the sensor can define edges of the sample chamber and/or measurement zone. By accurately controlling the distance between cuts, variability in sample chamber volume can often be reduced. In some instances, these cuts are preferably parallel to each other, as parallel cuts are typically the easiest to reproduce.

Sensor Connection to Electrical Device

Referring generally now to FIGS. 16A and 16B, 17A and 17B, and 18A and 18B, the assembled sensor of FIGS. 5A through 5C (as will be referred to as sensor 1420) is typically coupled to a meter or other electrical device by electrical connector 1500 which is configured to couple with and contact the end of the sensor 1420 at contact pads 423, 425, 443, 444. The sensor meter typically includes a potentiostat or other component to provide a potential and/or current for the electrodes of the sensor. The sensor reader also typically includes a processor (e.g., a microprocessor or hardware) for determining analyte concentration from the sensor signals. The sensor meter also includes a display or a port for coupling a display to the sensor. The display displays the sensor signals and/or results determined from the sensor signals including, for example, analyte concentration, rate of change of analyte concentration, and/or the exceeding of a threshold analyte concentration (indicating, for example, hypo- or hyperglycemia).

One example of a suitable connector is shown in FIGS. 16A and 16B, 17A and 17B, and 18A and 18B. Connector 1500 (which is used to connect a sensor to a meter or other electrical device) is generally a two part structure, having top portion 1510 and bottom portion 1520 (see FIG. 16B). Positioned between and secured by top portion 1510 and bottom portion 1520 are contact leads 1423, 1425, 1443, 1444 that provide electrical connection between the sensor 1420 and a meter. These leads 1423, 1425, 1443, 1444 have proximal ends to physically contact pads 423, 425, 443, 444 (in FIGS. 5A and 5B, respectively) and distal ends to connect to any attached meter. The end of the sensor 1420 which has the contact pads can be slid into or mated with the connector 1500 by placing the sensor 1420 into slide area 1530, which provides a support for and retains sensor 1420. It is typically important that the contact structures of the connector 1500 make electrical contact with the correct pads of the sensor so that the working electrode and counter electrode(s) are correctly coupled to the meter.

Figure 16A:
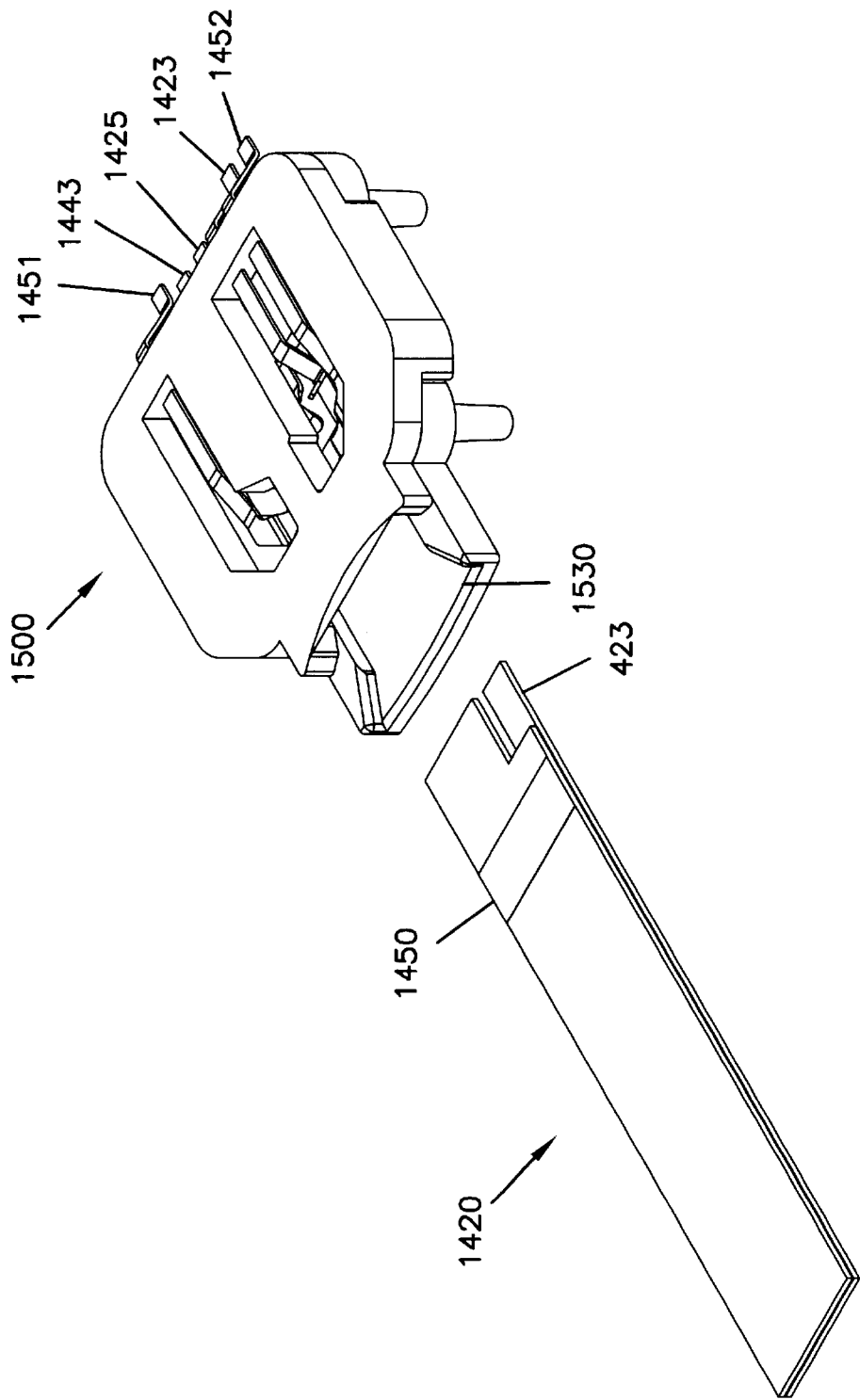
FIG. 16A is a top perspective view of a sensor positioned for insertion within an electrical connector device in accordance with the present invention.
Figure 16B:
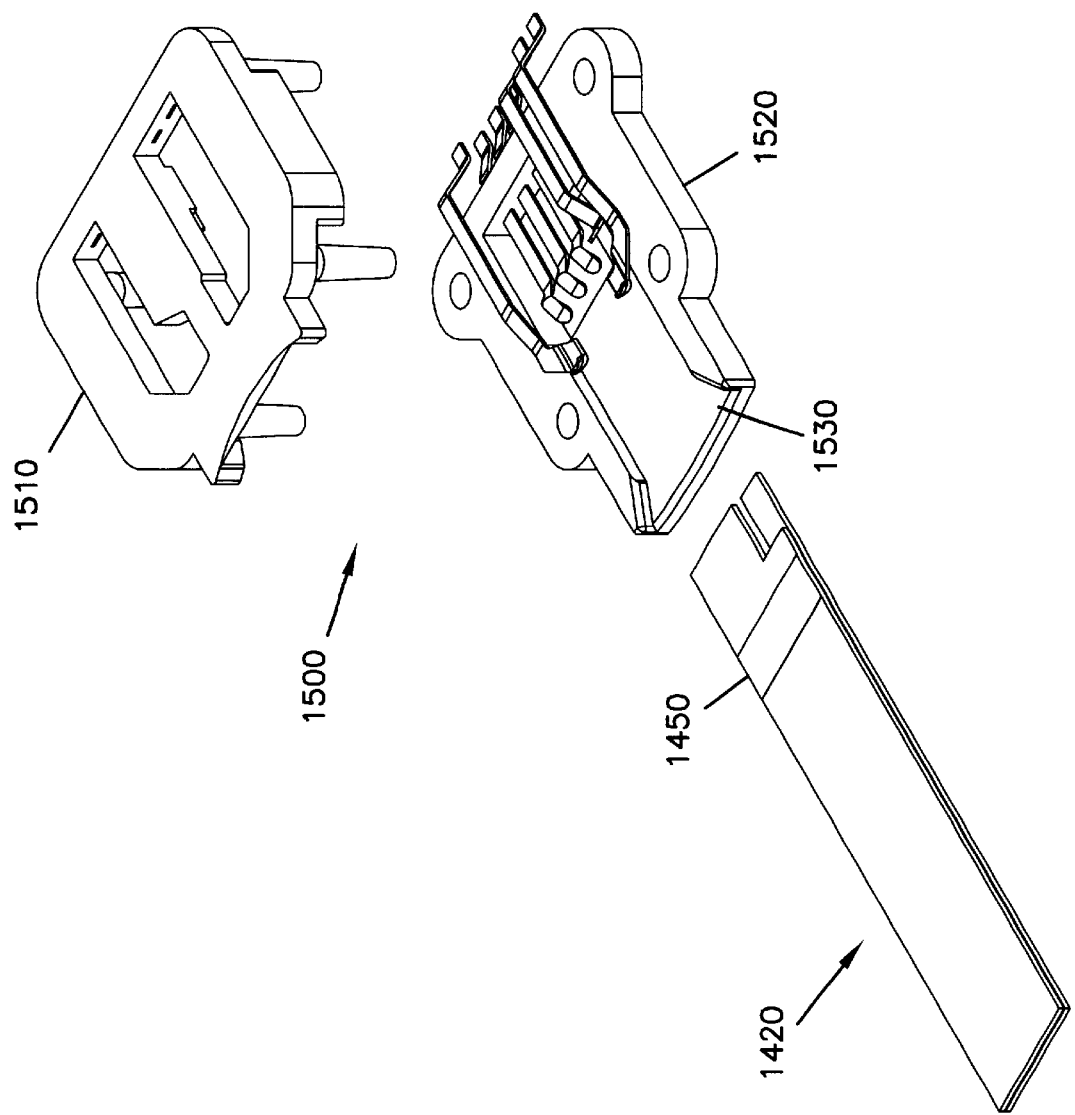
FIG. 16B is an exploded view of the electrical connector device of FIG. 16A.
Figure 17A:
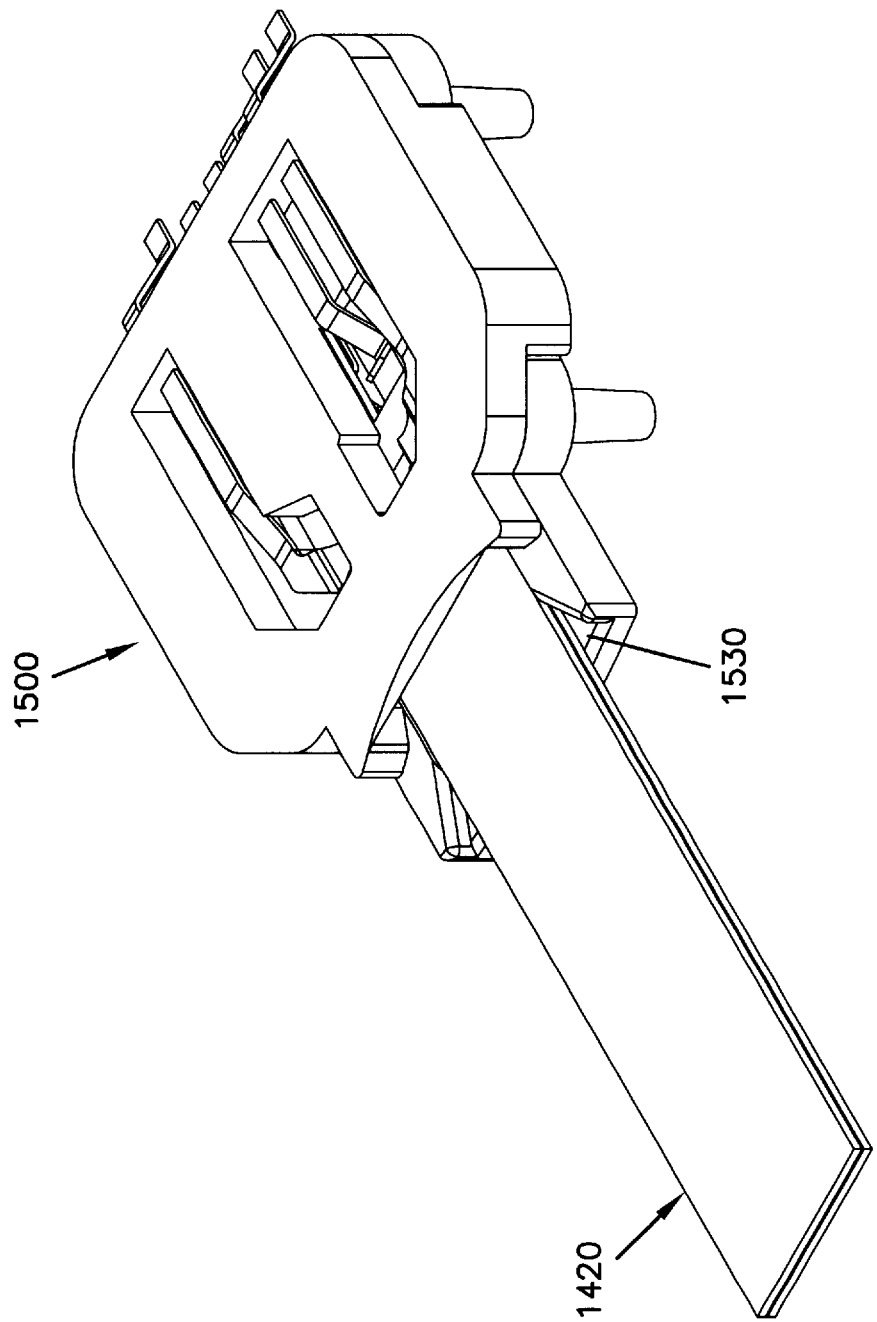
FIG. 17A is a top perspective view of a sensor fully positioned within the electrical connector device of FIG. 16A.
Figure 17B:
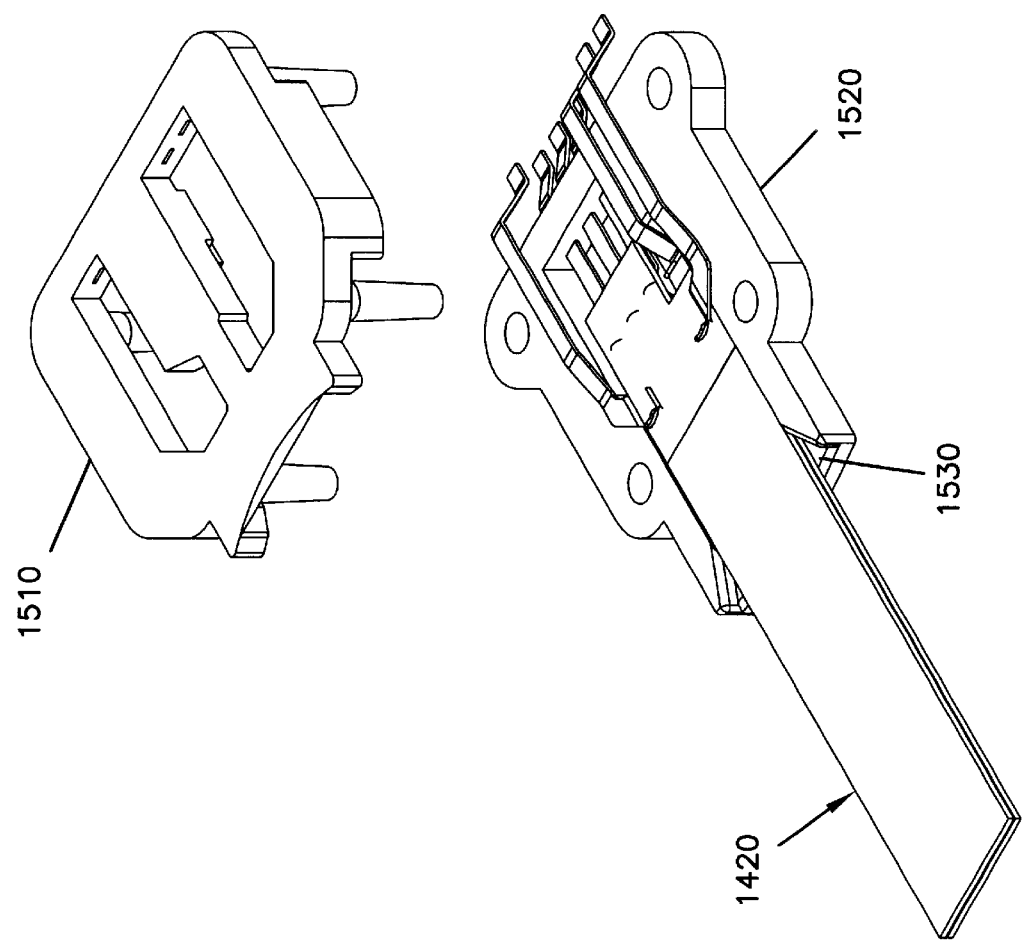
FIG. 17B is an exploded view of the electrical connector device of FIG. 17A.
Figure 18A:
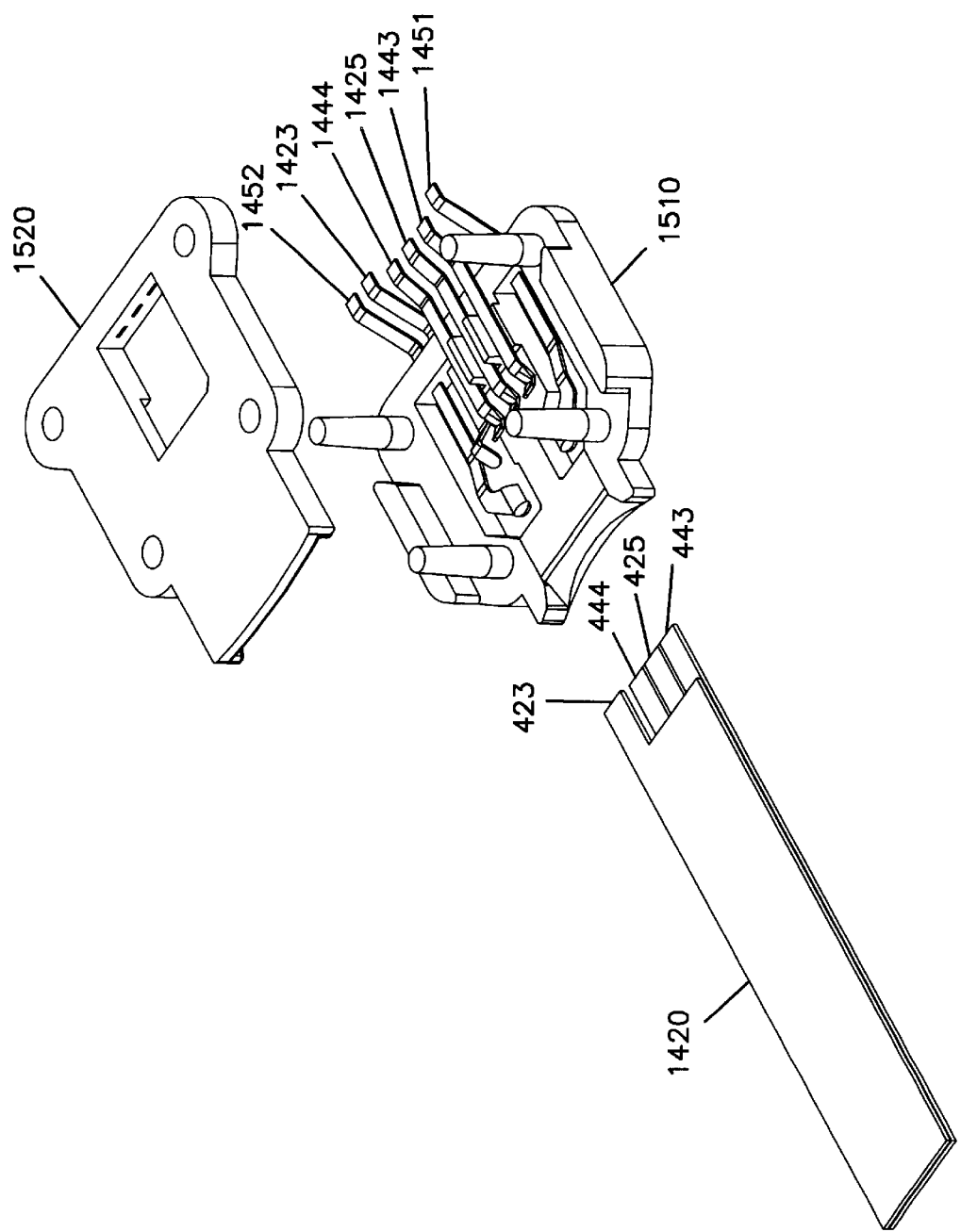
FIG. 18A is a bottom perspective view of the electrical connector device of FIGS. 16A and 16B.
Figure 18B:
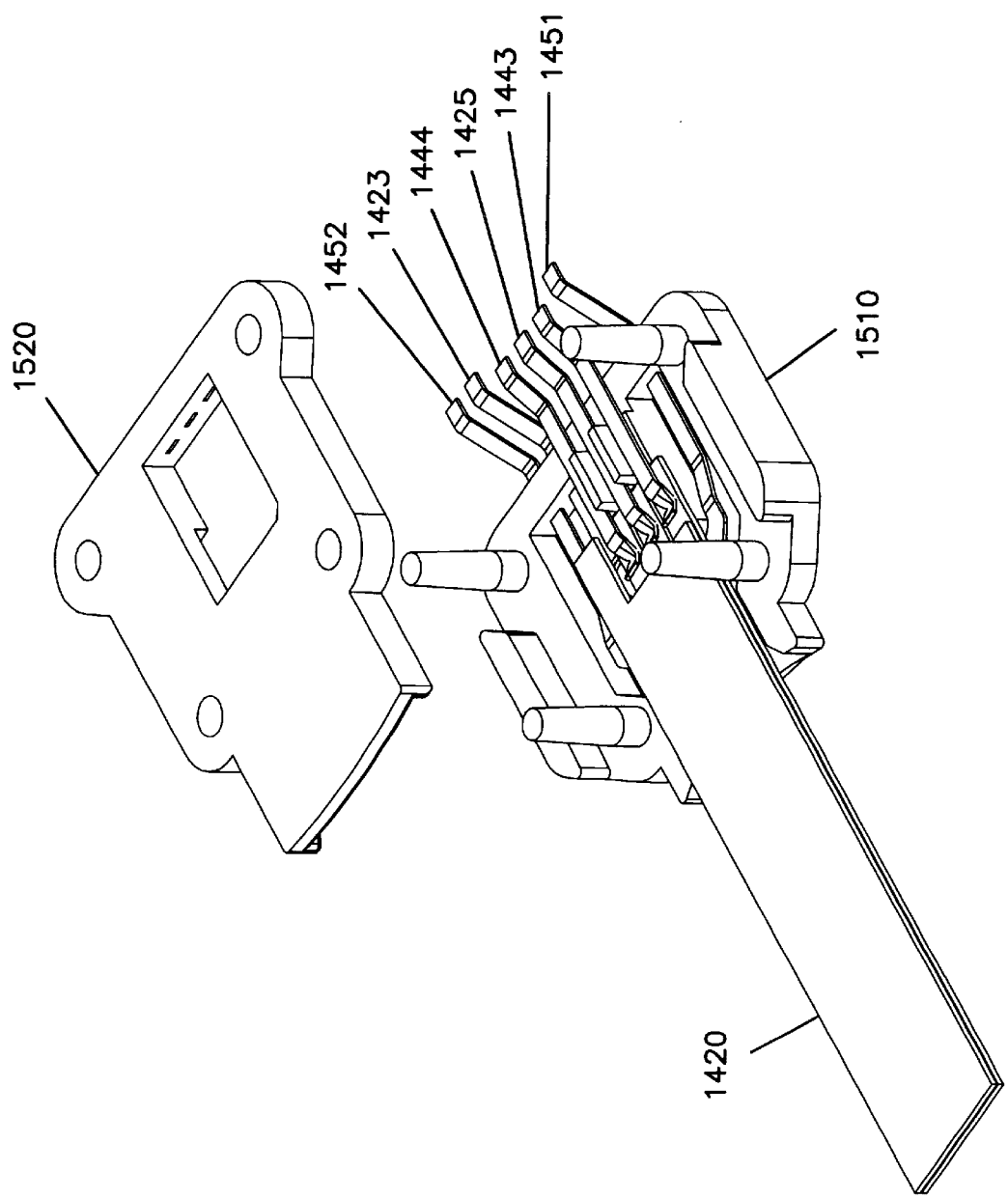
FIG. 18B is a bottom perspective view of the electrical connector device of FIGS. 17A and 17B.
Figure 19A:
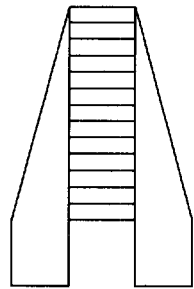
FIGS. 19A through 19L illustrate examples of suitable conductive pathways between contact pads.
Figure 19B:
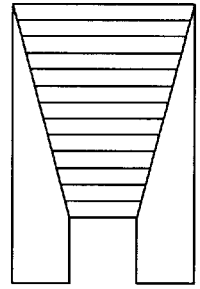
Figure 19C:
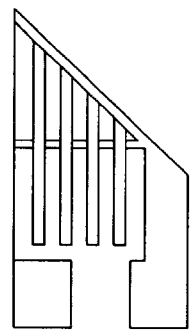
Figure 19D:
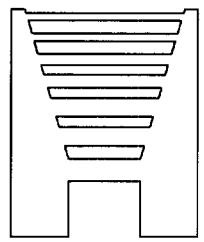
Figure 19E:
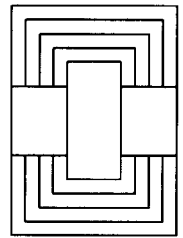
Figure 19F:
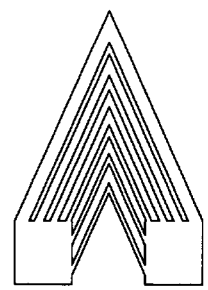
Figure 19G:
Figure 19H:
Figure 19I:
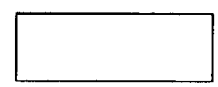
Figure 19J:
Figure 19K:
Figure 19L:

One optional feature is an insertion monitor 1450, that is illustrated in FIGS. 16A and 16B, which are top views of the sensor prior to insertion into connector 1500. This conductive insertion monitor is positioned on the non-conductive base substrate and has a contact pad for electrical contact with a connector. The insertion monitor is configured and arranged to close an electrical circuit between two contact structures 1451 and 1452 when the sensor is properly inserted into the connector. Proper insertion into the connector 1500 means that the sensor strip 1420 is inserted right side up, that the correct end of the strip is inserted into the connector, and that the strip is inserted far enough into the connector that reliable electrical connections are made between the electrodes' contact pads on the strip and the corresponding contact structures of the connector. Preferably, no closed circuit is made unless all electrode pads have properly contacted the contact structures of connector 1500. The insertion monitor may have shapes other than a stripe across the width of the sensor; for example, other designs include an individual dot, a grid pattern, or may include stylistic features, such as words or letters.

Because this insertion monitor 1450 is not at the end with the contact regions for the electrodes, the insertion monitor 1450 does not require additional width space on the sensor. The width of the contact pads 443, 425, 444, 423 is defined as the width on which a lead could be placed that would result in an electrical connection; typically, the contact width is the width of the exposed contact area. In one embodiment, six contact lead structures on the connector (i.e., 1451, 1443, 1425, 1444, 1423, 1452) can contact sensor 1420 in the same width as the four contact pads (i.e., 443, 425, 444, 423). This concept of having contact points on the sensor that occupy more width than the width of the sensor may be used for any number of contact points; this may be used with or without an insertion monitor.

As a particular example, four leads 1443, 1425, 1444, 1423 make contact with contact pads 443, 425, 444, 423. If each lead and/or contact pad is one millimeter wide, a sensor of at least 4 mm wide is needed to make contact. Additional leads, such as those for insertion monitor 1450 (i.e., contact leads 1451, 1452), can make contact by having leads 1451, 1452 extend along the side of leads 1443 and 1423 and then angle in toward the center of the strip 1420 after the point where leads 1443, 1425, 1444, 1423 contact strip 1420. The insertion monitor stripe leads 1451, 1452 cross side edges of sensor 1420 to make contact with the sensor, thus not requiring additional sensor width.

The contact structures are parallel and non-overlapping and they run longitudinally from the distal end to the proximal end. The lead structures 1443, 1425, 1444, 1423 terminate at their proximal end, but lead structures 1451, 1452 continue longitudinally past the proximal end of lead structures 1443, 1425, 1444, 1423. Once past the proximal end, lead structures 1452, 1452 angle in toward the center of the sensor strip.

The insertion monitor can also be used to encode information on a test strip. The encoded information can be, for example, calibration information for that manufacturing lot or for that specific strip. Such calibration information may relate to the sensitivity of the strip or to the y-intercept of its calibration curve. In one embodiment, the insertion monitor comprises two or more contact pads for connection to a meter. The two or more contact pads are connected to each other by a conductive material, such as a conductive ink. The resistance of conductive path between the two or more contact pads is related to the encoded information. As an example of discrete calibration values, resistance values in a given range can correspond to one calibration setting, and resistance values in a different range can correspond to a different calibration setting. As an example of continuous calibration values, the calibration setting may be a continuous function of the resistance. Examples of suitable conductive pathways between contact pads are shown in FIGS. 19A through 19L.

In FIGS. 19A–19F, multiple conductive pathways with different resistances are printed on the strip. The resistance of the pathway is varied by cutting or scoring some or all of the conductive pathways so that they do not carry charge. In FIGS. 19G–19L, the resistance is controlled by the width or length of the conductive path. While it is preferred to provide this encoded information on the insertion monitor, it should be recognized that the insertion monitor function and the encoding of information can also be implemented separately using separate conductive traces on the strip.

Figure 20:
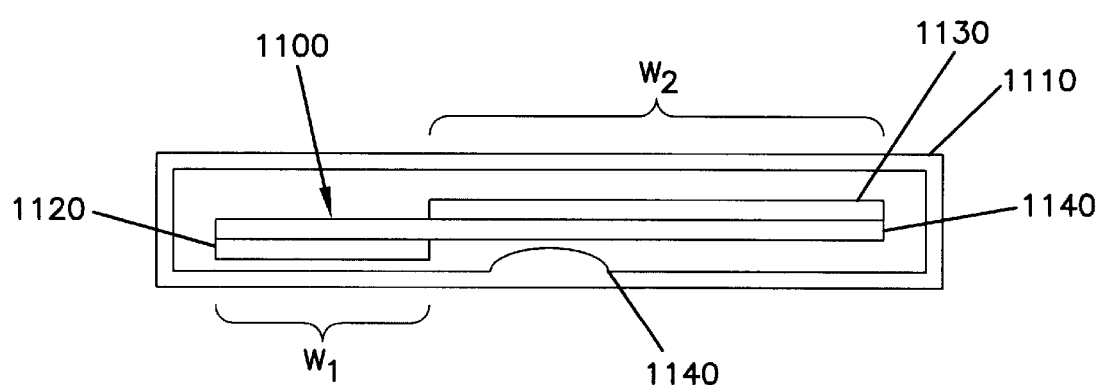
FIG. 20 illustrates a cross-sectional view looking from inside a connector to a sensor of the invention disposed within the connector.

In another embodiment to ensure proper insertion of a sensor into a meter, the meter may include a raised area or bump that prevents or hinders the insertion of the sensor in an improper direction, as shown in FIG. 20. To ensure proper insertion of the sensor 1100 into a connector 1110, the connector 1110 may include a raised area 1140 that prevents or hinders the insertion of the sensor in an improper direction. For example, the width, w2, of the contact region of the second substrate 1130 may be wider than the width, w1, of the contact region of the first substrate 1120. In this instance, the raised area 1140 is positioned to allow sensor 1100 to be slid into the connector so that the first substrate 1120 is next to the surface 1150 from which the raised area 1140 protrudes, but would prevent or hinder having the second substrate 1130 next to the surface 1150 from which the raised area 1140 protrudes. Objects other than a raised area can also be used to guide the user in correct introduction of the sensor into the meter.

Integrated Sample Acquisition and Analyte Measurement Device

An analyte measurement device constructed according to the principles of the present invention typically includes a sensor, as described hereinabove, combined with a sample acquisition apparatus to provide an integrated sampling and measurement device. The sample acquisition apparatus typically includes, for example, a skin piercing member, such as a lancet, that can be injected into a patient's skin to cause blood flow. In a preferred embodiment, the integrated sample acquisition and analyte measurement device comprises a lancing instrument that holds a lancet and measurement strip. The lancing instrument preferably requires active cocking. By requiring the user to cock the device prior to use, the risk of inadvertently triggering the lancet is minimized. Preferably, the lancing instrument will also permit the user to adjust the depth of penetration of the lancet into the skin. Such devices are already commercially available from companies such as Boehringer Mannheim and Palco. This feature allows users to adjust the lancing device for differences in skin thickness, skin durability, and pain sensitivity across different sites on the body and across different users.

Figure 21:
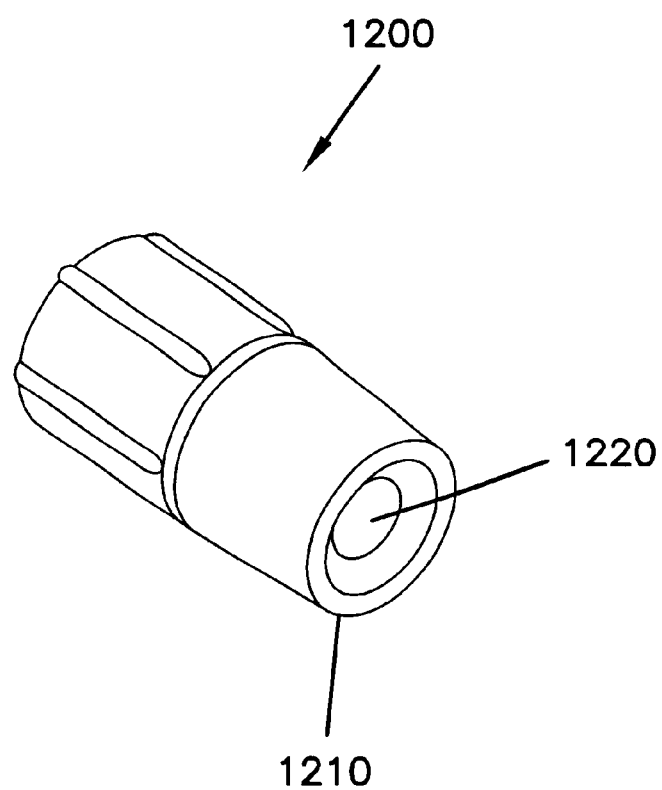
FIG. 21 illustrates a perspective view of a ring for use with a lancet device.

Typically, a larger sample of body fluid such as blood or interstitial fluid is expressed when pressure is applied around a site where a hole has been created the skin. A sample acquisition device having a protruding ring, such as illustrated in FIG. 21, may be used. Ring 1200 circumferentially surrounds the lancing site to create increased pressure and extract a larger sample out of the wound. A lancet would protrude from the center 1220 of ring 1200. Ring 1200 has a surface area 1210 that presses against the skin, thus increasing the tension on the skin and often providing a bump of skin. Skin that is more taught, and even extended, provides a large volume of fluid from the wound. The increased surface area 1210 and tighter skin provided by ring 1200, decreases the amount of pain experienced by the patient during the lancing. Further, the tendency to bruise is typically decreased.

In one embodiment, the lancing instrument and the meter are integrated into a single device. To operate the device the user need only insert a disposable cartridge containing a measurement sensor and lancing device into the integrated device, cock the lancing instrument, press it against the skin to activate it, and read the result of the measurement. Such an integrated lancing instrument and test reader simplifies the testing procedure for the user and minimizes the handling of body fluids.

Operation of the Sensor and Meter

An electrochemical sensor of the invention can be operated with or without applying a potential across the electrodes. In one embodiment, the electrochemical reaction occurs spontaneously and a potential need not be applied between the working and counter electrodes. In another embodiment, a potential, which may or may not remain constant, is applied between the working and counter electrodes. The magnitude of the required potential depends on the redox mediator used. The potential at which the electrode poises itself, or where it is poised by applying an external bias, and where the analyte is electrolyzed, is typically such that the electrochemical reaction is driven to or near completion, but it is, preferably, not oxidizing enough to result in significant electrochemical reaction of interferents, such as urate, ascorbate, and acetaminophen, that can affect the signal measured. For non-leachable redox mediators, the potential is typically between about −350 mV and about +400 mV versus the standard calomel electrode (SCE). Preferably, the potential of the redox mediator is more negative than +100 mV, more preferably the potential is more negative than 0 mV, and most preferably the potential is about −150 mV versus SCE.

When an external potential is applied, it can be applied either before or after the sample has been placed in the sample chamber. If the measurement zone includes only a portion of the sample chamber then the potential is preferably applied after the sample has come to rest in the sample chamber to prevent electrolysis of sample passing through the measurement zone as the sample chamber is filling.

Alternatively, in the case where the measurement zone includes most or all of the sample chamber, the potential can be applied before or during the filling of the sample chamber without affecting the accuracy of the assay. When the potential is applied and the sample is in the measurement zone, an electrical current will flow between the working electrode and the counter electrode. The current is a result, at least in part, of the electrolysis of the analyte in the sample. This electrochemical reaction occurs via the redox mediator and the optional second electron transfer agent. For many biomolecules, B, the process is described by the following reaction equations:

Biochemical B is oxidized to C by redox mediator A in the presence of an appropriate enzyme. Then the redox mediator A is oxidized at the electrode. Electrons are collected by the electrode and the resulting current is measured. The measured current may also include a background current resulting in a measured background charge, due, at least in part, to the shuttling of a diffusible redox mediator between the working electrode and the counter electrode. This background current can be minimized or accounted for, as described in PCT Application PCT/US99/23425, incorporated herein by reference.

A variety of techniques can be used to determine the concentration of an analyte in a sample. These techniques include, for example, coulometry, amperometry, and potentiometry. To determine the concentration of analyte (e.g., glucose) in the sample by coulometry, the charge passing or projected to pass between the working electrode(s) and counter electrode(s) during electrolysis of the analyte is determined. Knowledge of the charge and the volume of the sample chamber permit the calculation of the concentration of the electrolyzed analyte in the sample. This charge can be determined by several methods.

For example, the charge can be measured directly. This can be accomplished using a coulometer and known coulometric techniques. Typically, the charge is measured during the complete or nearly complete electrolysis of the analyte.

As another example, the charge can be determined from measurements of the electrolysis current, $i_t$, over time, t. A series of currents ($i_x$, $i_{x+1}$, $i_{x+2}$, ...) is measured for a series of times ($t_x$, $t_{x+1}$, $t_{x+2}$, ...). The current can then be integrated (e.g., numerically integrated using known numerical methods) to give the charge. In some instances, current can be measured during the entire electrolysis. In other instances, current can be extrapolated after a period of time and the charge determined using a combination of the measured currents and extrapolated currents.

Figure 15A:
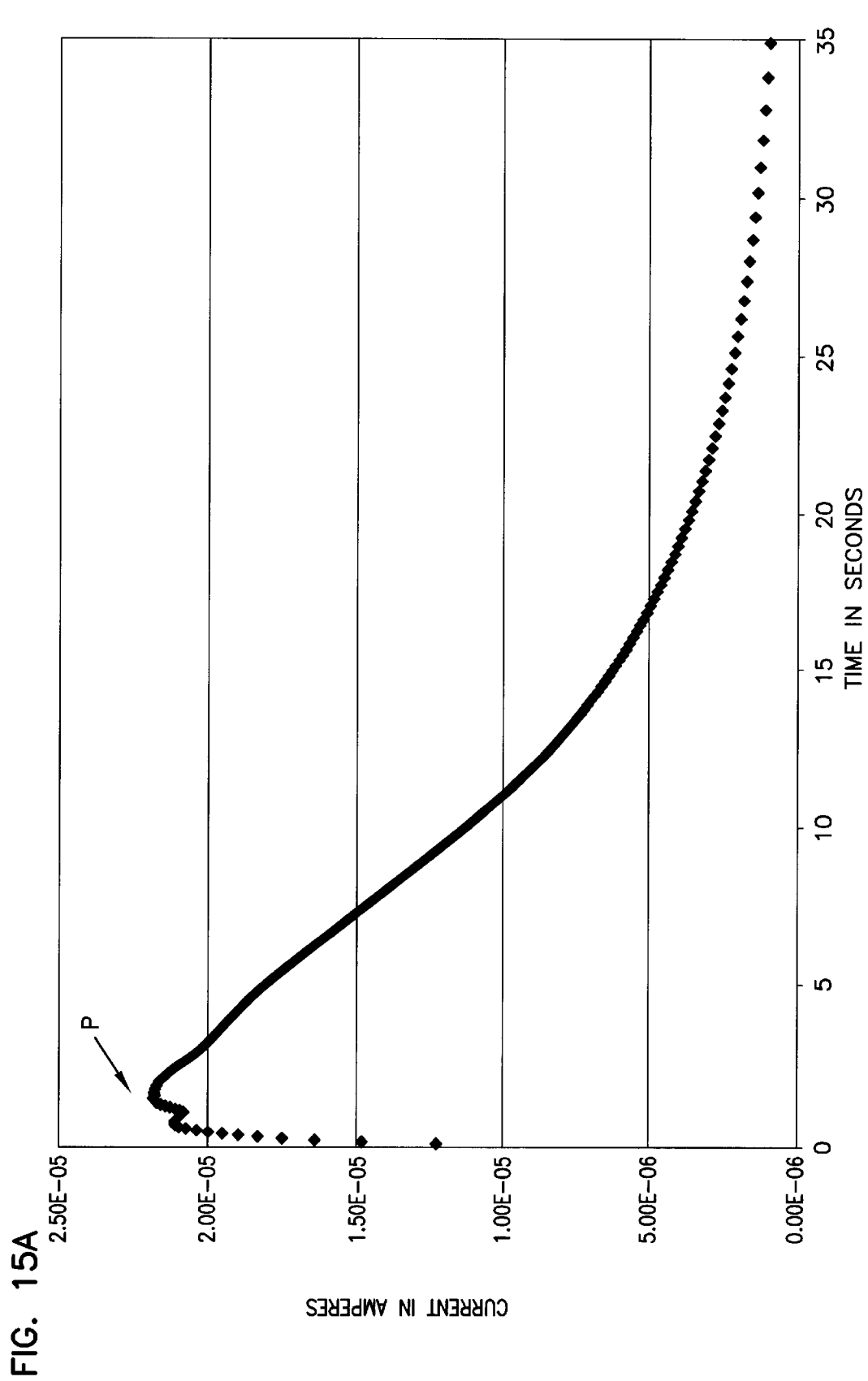
FIG. 15A is a graphical representation of the current over time used to calculate the concentration of an analyte.
Figure 15B:
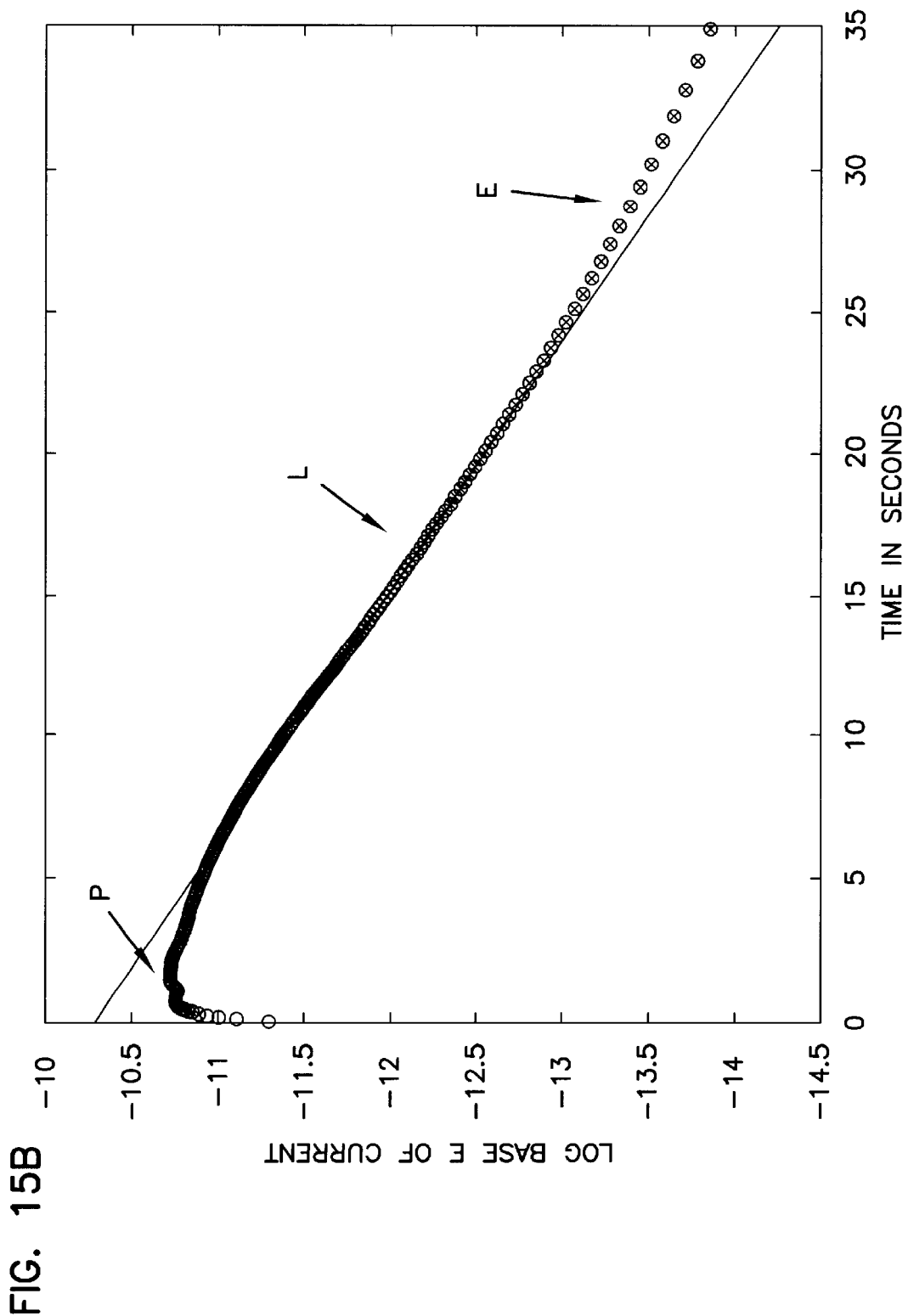
FIG. 15B is a graphical representation of the log of current over time used to calculate the concentration of an analyte.

Extrapolation of current utilizes a projected relationship between current and time during at least a portion of the electrolysis. Typically, when the system is diffusion limited, the natural logarithm of the current is linearly related to the time. This typically occurs after a period of time during which the sensor "equilibrates". FIG. 15A is an example of a graph of current versus time for electrolysis of an analyte, such as glucose, in one of the previously described sensors; FIG. 15B is a graph of the natural logarithm of current versus time for the same data. After the sample completely fills the sample chamber, the current increases to a peak current value, designated as "P" in FIGS. 15A and 15B, during which time the sensor is equilibrating. The peak current typically occurs during a period of time in which the system is kinetically, rather than diffusionally, limited. Typically, the current then begins to decrease, although, in some instances, further increases may occur before the current becomes diffusion limited. Eventually, the current values enter a region, designated as "L" in FIG. 15B, where there is a linear relationship between the natural logarithm of current and time. The remaining current needed to electrolyze a remaining portion of the analyte can then be extrapolated using estimation methods, such as nonlinear or, preferably, linear estimation methods (e.g., linear least squares techniques). The region where extrapolation occurs is designated as "E" in FIG. 15B and the extrapolation is indicated as a solid line.

For this discussion, the current values being referred to are the absolute value of the actual current, thus, the sign of the current measurement is ignored. For example, the peak current is the largest deviation from zero current, whether positive or negative.

During the period when the system is diffusion limited the relationship between the natural logarithm of the current and time is linear. The remaining charge required to completely electrolyze the analyte remaining in the sample can be reliably estimated from the slope of this line. Care must be taken to ensure that the system is in the diffusion limited range before performing the estimation. One method of ensuring that the system is in the diffusion limited regime includes observing the current values until the peak current, $i_{peak}$, ("P") is achieved. Current values continue to be observed until the current drops below a threshold value, $i_{thresh}$, that is typically a fraction of the peak current. For example, the threshold value can be one half, one third, or one quarter of the peak current (e.g., $i_{thresh}=J*i_{peak}$ where j is, for example, 0.5, 0.33, or 0.25). The threshold value is chosen based on the characteristics of the sensor so that one has a high degree of confidence that the system will be diffusion limited at this time.

Many other methods may be used to ensure that the system is in a diffusion limited regime. For example, one could observe the current values after $i_{peak}$ until an inflection point is reached and the second derivative of the natural log of the current turns positive. At this point the system is typically in a diffusion limited regime.

After achieving the threshold value, slope values are determined using natural logarithms of two or more of the measured current values (e.g., $m_x=(\log(i_x)-\log(i_{x-y}))/(t_x-t_{x-y})$ where $m_x$ is the slope at time $t_x$, $i_{x-y}$ is the current at time $t_x$, and $i_{x-y}$ is the current at time $t_{x-y}$ before $t_x$). Although the slope can be determined using natural logarithms of any two current values (e.g., current values measured one directly after the other), preferably the slope is determined using natural logarithms of multiple consecutive current values or current values that are spaced apart by at least about ten (i.e., y=10), and, preferably, at least about thirty (i.e., y=30), current values. This procedure can reduce the effect of random noise in the system. Optionally, the consistency of multiple slope values (e.g., three or five or ten slope values) can be observed for verification. For example, the system can look for ten monotonically decreasing slope values before accepting the slope value for use in the estimation.

The determined slope value is used to extrapolate the charge required to completely electrolyze the analyte remaining in the sample. That is, the current is extrapolated to zero current. Known extrapolation techniques (e.g., linear extrapolation techniques) can be used. The total charge required to electrolyze the analyte is determined by adding the measured charge and extrapolated charge.

Current values (or other measured values) can also be used to monitor the operation of the sensor and meter. For example, ratios of current values can be checked to determine if there has been some failure of the measurement (e.g., the sensor has been pulled out of the measuring device, etc.). The acceptable ratio range will typically depend on the type and components of the sensor, the rate at which measurements are made, and the acceptable noise level. As an example, an acceptable ratio range could be, for example, 2:1 to 1:2 for immediately adjacent measurements.

The discussion above has focused on the extrapolation of charge required to complete electrolysis of an analyte in a sample using the slope of the natural logarithm of current versus time under diffusion limited conditions. Those skilled in the art will recognize that this slope is related to a Effective Diffusion Coefficient, and that other linear or non-linear mathematical functions related to the Effective Diffusion Coefficient can also be used to extrapolate the charge.

The extrapolation of current measurements and the determination of charge passed or projected to pass, as well as the concentration of the analyte, and other functions can be performed by a processor with or without a storage medium, in which the desired procedures are performed by software, hardware, or a combination thereof. According to another embodiment, these same procedures are accomplished using discrete or semi-programmable hardware configured, for example, using a hardware descriptive language, such as Verilog. In yet another embodiment, the procedures are performed using a processor having at least one look-up table arrangement with data stored therein to represent the complete result or partial results of the above equations based on a given set of input data.

Current measurements can be made by a variety of methods. For example, the current measurements can be made by measuring the current directly using any known techniques and devices.

Another method of measuring current includes discharging a known amount of charge into the sample (by electrolysis of the analyte) and measuring the time required for the discharge. Current is then calculated as the quotient of charge and discharge time. As an example, a capacitor can be charged by circuitry in the meter and then coupled to the working or counter electrode(s) to discharge by electrolysis of the analyte. The time to discharge to a threshold level can be measured using, for example, a clock circuit that is part of the processing circuitry of the meter. The use of a clock circuit permits very accurate measurements of time. This can be advantageous over designs that directly measure current or charge and must convert these analog measurements to processible digital representations using the more expensive A/D (analog-to-digital) converters.

The accuracy of the charge and time measurement, which provides the current values, affects the accuracy of the final analyte concentration measurement. Although it is desired to use a high-quality and highly accurate measuring device, the capacitor used to store the charge can be a high-quality, expensive capacitor that has a precisely known capacitance. Alternatively, an accurate charge measurement can be obtained by using a calibrating resistor in parallel with the capacitor. During a calibration period, the capacitor discharges through the resistor and the current through the resistor or the time constant of the discharge can be determined. This can then be used to determine the charge stored in the capacitor. A high-quality, very accurate resistor is typically less expensive than a similarly accurate capacitor, and will provide the same amount of accuracy to the charge measurement.

The charge, Q, no matter how determined, is then used to calculate the concentration of the analyte ($C_A$) by the following equation (when the redox mediator is non-leachable):

$$C_A = Q/nFV \quad (3a)$$

where n is the number of electron equivalents required to electrolyze the analyte, F is Faraday's constant (approximately 96,500 coulombs per equivalent), and V is the volume of sample in the measurement zone. When using a diffusible mediator, the concentration of the analyte can be obtained from the following equation:

$$C_A = (Q_{tot} - Q_{back})/nFV \quad (3b)$$

where $Q_{tot}$ is the total charge transferred during the measurement and $Q_{back}$ is the amount of charge transferred that was not due to the analyte, e.g., charge transferred by the shuttling of the diffusible mediator between the working electrode and the counter electrode. In at least some instances, the sensor is constructed so that the background charge is at most 5 times the size of the charge generated by electrolysis of an amount of analyte. Preferably, the background signal is at most 200%, 100%, 50%, 25%, 10%, or 5% of the charge generated by electrolysis of the analyte.

One example of a method for determining the ratio of background signal to signal generated by electrolysis of the analyte is described as follows. If the shuttling of the redox mediator is not disabled by the applied potential, the charge that results from the shuttling may be represented by the following formula:

$$Q_{back} = (AFD_M C_M/d)(t n_M)$$

where A is the area of the working electrode; F is Faraday's constant (96,500 coulombs/equivalent); $D_M$ is the effective diffusion coefficient of the redox mediator; $C_M$ is the concentration of the redox mediator in the measurement zone; d is the distance separating facing electrodes; t is the amount of time for the measurement; and $n_M$ is the number of electrons gained or lost by the redox mediator.

Additionally, the charge of the analyte, when the analyte is electrooxidized to about 90% completion in the measurement period, may be represented by the following formula:

$$Q_G = Ad(0.90)C_G n_G F$$

where A is the area of the working electrode; d is the distance separating facing electrodes; $C_G$ is the concentration of glucose; n is the number of electrons needed to electrolyze the analyte (e.g., 2 electrons per glucose molecule); and F is Faraday's constant. For glucose, when $C_G$ is 5 mM (or $5 \times 10^{-6}$ moles/cm$^3$), t is 60 seconds, $n_G$ is 2, and $n_M$ is 1, the ratio of charge from the redox mediator to the charge from electrooxidation of the analyte may be represented by the following formula:

$$Q_{Back}/Q_G = (D_M C_M/d^2)(t n_M/(0.9 n_G C_G)) = (D_M C_M/d^2) \times (6.7 \times 10^6)$$

For example, if the ratio of $Q_{Back}/Q_G$ is 5, then $(D_M C_M)/d^2$ is $7.5 \times 10^{-7}$ moles/(cm$^3$ sec). Also for example, if the ratio of $Q_{Back}/Q_G$ is 1, then $(D_M C_M)/d^2$ is $1.5 \times 10^{-7}$ moles/(cm$^3$ sec). Still another example, if the ratio is 0.1, then $(D_M C_M)/d^2$ is $1.5 \times 10^{-8}$ moles/(cm$^3$ sec). Thus, depending on the ratio desired, a sensor may be configured to have the desired ratio by choosing $D_M$, $C_M$, and d accordingly.

The ratio can be affected, for example, by reducing the concentration of the redox mediator (i.e., $C_M$ may be reduced). Alternatively, or additionally, the diffusion of the redox mediator may be reduced. Other sensor configurations are also suitable for controlling the ratio of background signal to signal generated by the analyte and will be described below.

The background charge, $Q_{back}$, can be accounted for in a variety of ways. $Q_{back}$ can be made small, for example, by using only limited amounts of diffusible redox mediator; by providing a membrane over the counter electrode that limits diffusion of the redox mediator to the counter electrode; or by having a relatively small potential difference between the working electrode and the counter electrode. Other examples of sensor configurations and methods suitable for reducing $Q_{back}$ include having a redox mediator reaction rate at the working electrode that is significantly faster than that at the counter electrode; immobilizing the redox mediator on the working electrode; having the redox mediator become immobilized on the counter or counter/reference electrode upon its reaction at the counter or counter/reference electrode; or slowing the diffusion of the redox mediator.

For coulometric measurements, at least 20% of the analyte is electrolyzed, preferably at least 50%, more preferably at least 80%, and even more preferably at least 90% of the analyte is electrolyzed. In one embodiment of the invention, the analyte is completely or nearly completely electrolyzed. The charge can then be calculated from current measurements made during the electrochemical reaction, and the concentration of the analyte is determined using equation (3a) or (3b). The completion of the electrochemical reaction is typically signaled when the current reaches a steady-state value. This indicates that all or nearly all of the analyte has been electrolyzed. For this type of measurement, at least 90% of the analyte is typically electrolyzed, preferably, at least 95% of the analyte is electrolyzed and, more preferably, at least 99% of the analyte is electrolyzed.

For coulometry, it is typically desirable that the analyte be electrolyzed quickly. The speed of the electrochemical reaction depends on several factors, including the potential that is applied between the electrodes and the kinetics of reactions (1) and (2). Other significant factors include the size of the measurement zone. In general, the larger the potential, the larger the current through the cell and therefore, the faster the reaction will typically occur. However, if the potential is too large, other electrochemical reactions may introduce significant error in the measurement. Typically, the potential between the electrodes as well as the specific redox mediator and optional second electron transfer agent are chosen so that the analyte will be almost completely electrolyzed in less than 5 minutes, based on the expected concentration of the analyte in the sample. Preferably, the analyte will be almost completely electrolyzed within about 2 minutes and, more preferably, within about 1 minute.

Although coulometry has the disadvantage of requiring the volume of the measured sample be known, coulometry is a preferred technique for the analysis of the small sample because it has the advantages of, for example, no temperature dependence for the measurement, no enzyme activity dependence for the measurement, no redoxmediator activity dependence for the measurement, and no error in the measurement from depletion of analyte in the sample. As already described above, coulometry is a method for determining the amount of charge passed or projected to pass during complete or nearly complete electrolysis of the analyte. One coulometric technique involves electrolyzing the analyte on a working electrode and measuring the resulting current between the working electrode and a counter electrode at two or more times during the electrolysis. The electrolysis is complete when the current reaches a steady state. The charge used to electrolyze the sample is then calculated by integrating the measured currents over time and accounting for any background signal. Because the charge is directly related to the amount of analyte in the sample there is no temperature dependence of the measurement. In addition, the activity of the enzyme does not affect the value of the measurement, but only the time required to obtain the measurement (i.e., less active enzyme requires a longer time to achieve complete electrolysis of the sample) so that decay of the enzyme over time will not render the analyte concentration determination inaccurate. And finally, the depletion of the analyte in the sample by electrolysis is not a source of error, but rather the objective of the technique. (However, the analyte need not be completely electrolyzed if the electrolysis curve is extrapolated from the partial electrolysis curve based on well-known electrochemical principles.)

It may be desirable in some instances to utilize non-coulometric assays, such as amperometric or potentiometric measurement techniques. "Amperometry" and "chronopotentiometry" refer to taking a potentiometric measurement at one or more points in time. These measurement techniques are useful when the volume of the measured sample is unknown; the volume of the sample in the measurement zone of a small volume sensor (i.e., no more than one microliter) may be difficult to accurately reproduce if the manufacturing tolerances of one or more dimensions of the measurement zone have significant variances. For information regarding using non-coulometric measuring, such as amperometric and potentiometric techniques, see, for example, U.S. application Ser. No. 09/295,962, filed Apr. 21, 1999, now issued as U.S. Pat. No. 6,338,790, and its continuations U.S. Pat. Nos. 6,299,757 and 6,461,496, all incorporated herein by reference in its entirety.

Heating of Sample

The sample can be heated to increase the rate of diffusion, oxidation, or reduction of the analyte. This heating can be accomplished by a variety of techniques including placing the sensor in a heated environment or applying a heating unit to the sensor.

Another technique includes providing a thermal heating element, such as, for example, a wire or an ink that is capable of converting electrical energy into heat energy, on the sensor. This wire or ink can be applied, for example, on the opposite side of a base material, such as a polymer film, from one or more of the working, counter, reference, or counter/reference electrodes, or applied around the periphery of the working, counter, reference, or counter/reference electrodes. In some instances, the sample is heated up to 5 to 20° C. above an initial temperature. In other instances, the temperature of the sample may not be known but a constant amount of power or current is applied to the wire or ink.

General Examples

The invention will be further characterized by the following general examples. These examples are not meant to limit the scope of the invention which has been fully set forth in the foregoing description. Variations within the concepts of the invention are apparent to those skilled in the art.

One method for manufacturing the sensor shown in FIGS. 5A through 5C, having a working electrode, multiple counter/reference electrodes, and a side filled sample chamber, is described below. According to the method described herein, a plurality of sensors are produced and then separated.

A first non-conducting substrate, preferably polyester, is provided. A conductive carbon ink, such as that available from Ercon of Wareham, Mass. under the trade designation "Graphite #G4491", is screen printed onto a first half of the first polymeric substrate in the pattern shown in FIG. 5A and dried, to provide the working electrode 422, trace 453 and contact pad 423. Once the substrate web is cut to the final size, each working electrode 422 will extend across the width of the sensor and have a trace 453 that extends to the far end of the sensor. As an example, a sensor can be made with a width of about 6.1 mm (0.240 inch). Typical sensor widths are about 2 mm to 20 mm, preferably about 4 mm to 10 mm, but wider or narrower sensors can be used as desired.

A sensing layer, as described in U.S. patent application Ser. No. 09/295,962, now U.S. Pat. No. 6,338,790, comprising a diffusible mediator and diffusible glucose dehydrogenase enzyme, is applied to the working electrode in a sample chamber region. The sensing layer can be provided on the electrode prior to or subsequent to providing the sample chamber. On the other half of the polyester substrate, a conductive silver/silver chloride ink, such as that commercially available from Ercon under the trade designation "Silver/Silver Chloride #R414", is screen printed onto a second half of the first polymeric substrate in the pattern shown in FIG. 5B and dried. In the embodiment shown in FIG. 5B, the Ag/AgCl ink provides a first indicator or reference electrode 441, a counter electrode 424, and a second indicator electrode 442. Counter electrode may extend across the entire sensor surface, or may extend only a portion thereof. As an example, the width of a counter electrode is about 1 mm to 20 mm, preferably about 2 to 10 mm. In one sensor configuration, the counter electrode 424 has a width of about 3.71 mm (0.146 inch). The indicator electrodes can have a width, for example, of about 0.1 mm to 5 mm, preferably about 0.25 mm to about 1 mm.

In one sensor configuration, working electrode, such as working electrode 422 shown in FIG. 5A, extends the width of the sensor, which is about 6.1 mm (0.240 inch). A counter electrode, such as counter electrode 424, has a width of about 3.71 mm (0.146 inch). Indicator electrodes, such as indicator electrodes 441, 442 in FIG. 5B, each can have a width of about 0.51 mm (0.020 inch). A spacing of 0.30 mm (0.012 inch) is present between these indicator electrodes and the counter electrode. The indicator electrodes may be each set back from the eventual side edge of the sensor strip, for example, by approximately 0.38 mm (0.015 inch), so that the electrodes 441, 442 are not damaged, for example, smeared, streaked, chipped or the like, by the process of slitting the substrate into individual sensors.

The invention has been described with reference to various specific and preferred embodiments and techniques. However, it will be apparent to one of ordinarily skill in the art that many variations and modifications may be made while remaining within the spirit and scope of the invention.

All publications and patent applications in this specification are indicative of the level of ordinary skill in the art to which this invention pertains. All publications and patent applications are herein incorporated by reference to the same extent as if each individual publication or patent application was specifically and individually incorporated by reference.

We claim:

1. An electrochemical sensor strip for determining a concentration of glucose in blood or interstitial fluid, the sensor comprising:
    a first substrate having a first major surface and a second major surface opposing the first major surface, the first substrate defining a proximal end of the strip, a distal end of the strip and first and second side edges of the strip extending from the proximal end to the distal end;
    a second substrate having a first major surface and a second major surface opposing the first major surface, the first and second substrates being disposed so that the first major surface of the first substrate is in facing relationship with the first major surface of the second substrate;
    spacer material disposed between the first substrate and the second substrate, the spacer material, the first substrate and the second substrate further defining:
        a first aperture along the proximal end and between the substrates,
        a second aperture along the first side edge and between the substrates,
        a channel leading from the first aperture to the second aperture, and
        a sample chamber adjacent the first aperture and along the channel, the sample chamber comprising a measurement zone having a volume of no more than 1 $\mu$L;
    a working electrode disposed on the first major surface of the first substrate;
    a glucose responsive enzyme disposed on the working electrode;
    a counter electrode disposed on the first major surface of one of the first substrate and the second substrate, the working electrode and the counter electrode being positioned relative to the sample chamber to generate a glucose responsive signal when sample containing glucose is disposed in the measurement zone; and
    an insertion monitor disposed on one of the first and the second major surfaces of one of the first substrate and the second substrate, the insertion monitor including a conductive stripe extending across a width of the sensor strip and the insertion monitor providing a path for electrical current between at least two contact leads of a meter.

2. The sensor according to claim 1, wherein the insertion monitor is disposed on the second major surface of the first substrate.

3. The sensor according to claim 1, wherein the counter electrode is disposed on the first major surface of the second substrate.

4. The sensor according to claim 1, wherein the insertion monitor has two or more contact regions for electrical contact with the meter.

5. The sensor of claim 1, wherein the insertion monitor is configured and arranged to provide encoded information about the strip.

6. An electrochemical sensor strip for determining the level of glucose in a sample of blood or interstitial fluid, the sensor strip having a first side edge and a second side edge, the sensor strip comprising:
    a first substrate having a first major surface and a second major surface opposing the first major surface, the first substrate defining a proximal end of the strip, a distal end of the strip and first and second side edges of the strip extending from the proximal end to the distal end;

a second substrate having a first major surface and a second major surface opposing the first major surface, the first and second substrates being disposed so that the first major surface of the first substrate is in facing relationship with the first major surface of the second substrate;

spacer material disposed between the first substrate and the second substrate, the spacer material, the first substrate and the second substrate further defining:
- a first aperture along the proximal end and between the substrates,
- a second aperture along the first side edge and between the substrates,
- a channel leading from the first aperture to the second aperture, and
- a sample chamber adjacent the first aperture, the sample chamber comprising a measurement zone having a volume of no more than 1 µL;

a working electrode on the first major surface of the first substrate;

a glucose responsive enzyme disposed on the working electrode;

a counter electrode on the first major surface of one of the first substrate and the second substrate, the working electrode and the counter electrode being positioned relative to the sample chamber to generate a glucose responsive signal when sample containing glucose is disposed in the measurement zone; and an insertion monitor comprising electrically conductive material forming a stripe extending from the first side edge to the second side edge of the sensor strip on one of the substrate surfaces.

7. The sensor strip of claim 6, comprising two working electrodes.

8. The sensor strip of claim 6, wherein the counter electrode is on the first major surface of the second substrate.

* * * * *